(12) United States Patent
Nielsen et al.

(10) Patent No.: US 10,704,050 B2
(45) Date of Patent: Jul. 7, 2020

(54) ENGINEERING OF ACETYL-COA METABOLISM IN YEAST

(71) Applicant: Biopetrolia AB, Göteborg (SE)

(72) Inventors: Jens Nielsen, Göteborg (SE); Verena Siewers, Göteborg (SE); Anastasia Krivoruchko, Göteborg (SE); Yiming Zhang, Göteborg (SE); Zongjie Dai, Göteborg (SE)

(73) Assignee: BIOPETROLIA AB, Gothenburg (SE)

( * ) Notice: Subject to any disclaimer, the term of this patent is extended or adjusted under 35 U.S.C. 154(b) by 937 days.

(21) Appl. No.: 15/030,132

(22) PCT Filed: Oct. 17, 2014

(86) PCT No.: PCT/SE2014/051228
§ 371 (c)(1),
(2) Date: Apr. 18, 2016

(87) PCT Pub. No.: WO2015/057154
PCT Pub. Date: Apr. 23, 2015

(65) Prior Publication Data
US 2016/0237441 A1     Aug. 18, 2016

Related U.S. Application Data

(60) Provisional application No. 61/893,124, filed on Oct. 18, 2013.

(51) Int. Cl.
| | |
|---|---|
| *C12N 1/16* | (2006.01) |
| *C12N 15/01* | (2006.01) |
| *C12P 7/16* | (2006.01) |
| *C12P 7/64* | (2006.01) |
| *C12N 9/10* | (2006.01) |
| *C12N 15/52* | (2006.01) |
| *C12N 9/02* | (2006.01) |
| *C12N 9/88* | (2006.01) |
| *C12P 5/00* | (2006.01) |
| *C12P 7/00* | (2006.01) |
| *C12N 9/00* | (2006.01) |

(52) U.S. Cl.
CPC ......... *C12N 15/52* (2013.01); *C12N 9/0008* (2013.01); *C12N 9/0051* (2013.01); *C12N 9/1025* (2013.01); *C12N 9/1029* (2013.01); *C12N 9/13* (2013.01); *C12N 9/88* (2013.01); *C12N 9/93* (2013.01); *C12P 5/00* (2013.01); *C12P 7/00* (2013.01); *C12Y 102/04001* (2013.01); *C12Y 102/07001* (2013.01); *C12Y 208/01008* (2013.01); *C12Y 401/01001* (2013.01); *C12Y 603/01* (2013.01)

(58) Field of Classification Search
CPC .................................... C12N 9/10; C12P 7/16
See application file for complete search history.

(56) References Cited

U.S. PATENT DOCUMENTS

| | | | |
|---|---|---|---|
| 8,637,286 B2 | 1/2014 | Burgard et al. | |
| 2010/0062505 A1* | 3/2010 | Gunawardena | C12N 9/0008 435/160 |
| 2013/0066035 A1 | 3/2013 | Burgard et al. | |
| 2016/0177341 A1* | 6/2016 | Chua | C12N 1/16 435/106 |

FOREIGN PATENT DOCUMENTS

| | | |
|---|---|---|
| WO | WO 2009/013159 | 1/2009 |
| WO | WO 2009/111672 | 9/2009 |
| WO | WO 2011/159863 | 12/2011 |
| WO | WO 2012/177726 | 12/2012 |
| WO | WO 2014/057008 | 4/2014 |

OTHER PUBLICATIONS

Flikweert et al., Yeast, 12, 247-257, 1996.*
Chen, Y. et al. "Establishing a platform cell factory through engineering of yeast acetyl-CoA metabolism", Metabolic Engineering, 15 (2013) pp. 48-54.
International Preliminary Report on Patentability corresponding to International Application No. PCT/SE2014/051228; dated Apr. 19, 2016; 11 pages.
International Search Report and Written Opinion corresponding to International Application No. PCT/SE2014/051228, dated Apr. 14, 2015; 18 pages.

* cited by examiner

*Primary Examiner* — Maryam Monshipouri
(74) *Attorney, Agent, or Firm* — Myers Bigel, P.A.

(57) ABSTRACT

The invention relates to engineering of acetyl-CoA metabolism in yeast and in particular to production of acetyl-CoA in a non-ethanol producing yeast lacking endogenous gene(s) encoding pyruvate decarboxylase and comprising a heterologous pathway for synthesis of cytosolic acetyl-CoA.

9 Claims, 11 Drawing Sheets
Specification includes a Sequence Listing.

SEQUENCE LISTING

<160> NUMBER OF SEQ ID NOS: 83

<210> SEQ ID NO 1
<211> LENGTH: 20
<212> TYPE: DNA
<213> ORGANISM: Saccharomyces cerevisiae

<400> SEQUENCE: 1
tacttgctat cgttcaacac                                         20

<210> SEQ ID NO 2
<211> LENGTH: 37
<212> TYPE: DNA
<213> ORGANISM: Saccharomyces cerevisiae

<400> SEQUENCE: 2

-continued cagcgtacga agcttcagtg cgtgaggtta tgagtag                                37

<210> SEQ ID NO 3
<211> LENGTH: 39
<212> TYPE: DNA
<213> ORGANISM: Saccharomyces cerevisiae

<400> SEQUENCE: 3
gtgatatcag atccactagt accaacgcta agcaataag                              39

<210> SEQ ID NO 4
<211> LENGTH: 21
<212> TYPE: DNA
<213> ORGANISM: Saccharomyces cerevisiae

<400> SEQUENCE: 4
ccttggttcc actaattcat c                                                 21

<210> SEQ ID NO 5
<211> LENGTH: 20
<212> TYPE: DNA
<213> ORGANISM: Saccharomyces cerevisiae

<400> SEQUENCE: 5
ttaggcataa tcaccgaaga                                                   20

<210> SEQ ID NO 6
<211> LENGTH: 39
<212> TYPE: DNA
<213> ORGANISM: Saccharomyces cerevisiae

<400> SEQUENCE: 6
cagcgtacga agcttcagga gaggaaagga cttactaca                              39

<210> SEQ ID NO 7
<211> LENGTH: 37
<212> TYPE: DNA
<213> ORGANISM: Saccharomyces cerevisiae

<400> SEQUENCE: 7
gtgatatcag atccactagt tctgtcctgt cttccag                                37

<210> SEQ ID NO 8
<211> LENGTH: 18
<212> TYPE: DNA
<213> ORGANISM: Saccharomyces cerevisiae

<400> SEQUENCE: 8
ggtgctctac tggtgatt                                                     18

<210> SEQ ID NO 9
<211> LENGTH: 20
<212> TYPE: DNA
<213> ORGANISM: Saccharomyces cerevisiae

<400> SEQUENCE: 9
acatcttcca agcatctcat                                                   20

<210> SEQ ID NO 10
<211> LENGTH: 38
<212> TYPE: DNA
<213> ORGANISM: Saccharomyces cerevisiae

```
<400> SEQUENCE: 10
cagcgtacga agcttcagga atcgcaccat atcccttta                    38

<210> SEQ ID NO 11
<211> LENGTH: 38
<212> TYPE: DNA
<213> ORGANISM: Saccharomyces cerevisiae

<400> SEQUENCE: 11
gtgatatcag atccactagc gttatcgccg tgaattac                     38

<210> SEQ ID NO 12
<211> LENGTH: 19
<212> TYPE: DNA
<213> ORGANISM: Saccharomyces cerevisiae

<400> SEQUENCE: 12
ttggttgtag atggtggtg                                          19

<210> SEQ ID NO 13
<211> LENGTH: 18
<212> TYPE: DNA
<213> ORGANISM: Saccharomyces cerevisiae

<400> SEQUENCE: 13
ctgaagcttc gtacgctg                                           18

<210> SEQ ID NO 14
<211> LENGTH: 20
<212> TYPE: DNA
<213> ORGANISM: Saccharomyces cerevisiae

<400> SEQUENCE: 14
tcaccatgag tgacgactga                                         20

<210> SEQ ID NO 15
<211> LENGTH: 19
<212> TYPE: DNA
<213> ORGANISM: Saccharomyces cerevisiae

<400> SEQUENCE: 15
ttccaacatg gatgctgat                                          19

<210> SEQ ID NO 16
<211> LENGTH: 19
<212> TYPE: DNA
<213> ORGANISM: Saccharomyces cerevisiae

<400> SEQUENCE: 16
ctagtggatc tgatatcac                                          19

<210> SEQ ID NO 17
<211> LENGTH: 32
<212> TYPE: DNA
<213> ORGANISM: Saccharomyces cerevisiae

<400> SEQUENCE: 17
gttgttggat cccaggagaa aaacatggct ga                           32

<210> SEQ ID NO 18
<211> LENGTH: 34
<212> TYPE: DNA
<213> ORGANISM: Saccharomyces cerevisiae
```

-continued

<400> SEQUENCE: 18
gttgttctcg agcgtttatc gataagtaac cgct                          34

<210> SEQ ID NO 19
<211> LENGTH: 35
<212> TYPE: DNA
<213> ORGANISM: Saccharomyces cerevisiae

<400> SEQUENCE: 19
gttgttgcgg ccgcgaggtt atttcactca tggct                         35

<210> SEQ ID NO 20
<211> LENGTH: 32
<212> TYPE: DNA
<213> ORGANISM: Saccharomyces cerevisiae

<400> SEQUENCE: 20
gttgttgagc tccatcacat caggcattga ga                            32

<210> SEQ ID NO 21
<211> LENGTH: 50
<212> TYPE: DNA
<213> ORGANISM: Saccharomyces cerevisiae

<400> SEQUENCE: 21
cgcttattta gaagtgtcaa caacgtatct acagctctca ggctaatcta         50

<210> SEQ ID NO 22
<211> LENGTH: 53
<212> TYPE: DNA
<213> ORGANISM: Saccharomyces cerevisiae

<400> SEQUENCE: 22
gaaagcatag caatctaatc taagttttaa ttacaacgca aaacaatgtc aga     53

<210> SEQ ID NO 23
<211> LENGTH: 20
<212> TYPE: DNA
<213> ORGANISM: Saccharomyces cerevisiae

<400> SEQUENCE: 23
gcgttgtaat taaaacttag                                          20

<210> SEQ ID NO 24
<211> LENGTH: 43
<212> TYPE: DNA
<213> ORGANISM: Saccharomyces cerevisiae

<400> SEQUENCE: 24
tccttccttt tcggttagag cggatctatc ttacagcacc agc                43

<210> SEQ ID NO 25
<211> LENGTH: 49
<212> TYPE: DNA
<213> ORGANISM: Saccharomyces cerevisiae

<400> SEQUENCE: 25
cgcttattta gaagtgtcaa caacgtatct acagagctct tacatgact          49

<210> SEQ ID NO 26
<211> LENGTH: 43
<212> TYPE: DNA

<210> SEQ ID NO 26
<211> LENGTH: 43
<212> TYPE: DNA
<213> ORGANISM: Saccharomyces cerevisiae

<400> SEQUENCE: 26 tccttcctttt tcggttagag cggataccta cttcttcttg gct          43

<210> SEQ ID NO 27
<211> LENGTH: 34
<212> TYPE: DNA
<213> ORGANISM: Saccharomyces cerevisiae

<400> SEQUENCE: 27
agcgatacgu atgagtaaac ccattgtgat ggaa                    34

<210> SEQ ID NO 28
<211> LENGTH: 32
<212> TYPE: DNA
<213> ORGANISM: Saccharomyces cerevisiae

<400> SEQUENCE: 28
cacgcgautt acttaacttc catcccttc gc                       32

<210> SEQ ID NO 29
<211> LENGTH: 36
<212> TYPE: DNA
<213> ORGANISM: Saccharomyces cerevisiae

<400> SEQUENCE: 29
atcaacgggu atgtatcagg ataaaattct tgtccg                  36

<210> SEQ ID NO 30
<211> LENGTH: 33
<212> TYPE: DNA
<213> ORGANISM: Saccharomyces cerevisiae

<400> SEQUENCE: 30
cgtgcgautt aagcggtaat atattcgaag tcc                     33

<210> SEQ ID NO 31
<211> LENGTH: 41
<212> TYPE: DNA
<213> ORGANISM: Saccharomyces cerevisiae

<400> SEQUENCE: 31
acgtatcgcu ttgtaattaa aacttagatt agattgctat g            41

<210> SEQ ID NO 32
<211> LENGTH: 45
<212> TYPE: DNA
<213> ORGANISM: Saccharomyces cerevisiae

<400> SEQUENCE: 32
acccgttgau ttgttttata tttgttgtaa aaagtagata attac        45

<210> SEQ ID NO 33
<211> LENGTH: 37
<212> TYPE: DNA
<213> ORGANISM: Saccharomyces cerevisiae

<400> SEQUENCE: 33
agcgatacgu atggcaactt taaaaacaac tgataag                 37

<210> SEQ ID NO 34
<211> LENGTH: 32

```
<212> TYPE: DNA
<213> ORGANISM: Saccharomyces cerevisiae

<400> SEQUENCE: 34
cacgcgautt aatccctaga ggcaaaacct tg                              32

<210> SEQ ID NO 35
<211> LENGTH: 34
<212> TYPE: DNA
<213> ORGANISM: Saccharomyces cerevisiae

<400> SEQUENCE: 35
atcaacgggu atggtagtca tcatcggtgg tggc                            34

<210> SEQ ID NO 36
<211> LENGTH: 35
<212> TYPE: DNA
<213> ORGANISM: Saccharomyces cerevisiae

<400> SEQUENCE: 36
cgtgcgautc aacaatgaat agctttatca taggc                           35

<210> SEQ ID NO 37
<211> LENGTH: 35
<212> TYPE: DNA
<213> ORGANISM: Saccharomyces cerevisiae

<400> SEQUENCE: 37
agcgatacgu atgtcatcaa caaagacgat gaccg                           35

<210> SEQ ID NO 38
<211> LENGTH: 35
<212> TYPE: DNA
<213> ORGANISM: Saccharomyces cerevisiae

<400> SEQUENCE: 38
cacgcgautt attcaattga caagacttct ttgac                           35

<210> SEQ ID NO 39
<211> LENGTH: 40
<212> TYPE: DNA
<213> ORGANISM: Saccharomyces cerevisiae

<400> SEQUENCE: 39
atcaacgggu atgtcagcta aattacttgc tgtaaagaca                      40

<210> SEQ ID NO 40
<211> LENGTH: 33
<212> TYPE: DNA
<213> ORGANISM: Saccharomyces cerevisiae

<400> SEQUENCE: 40
cgtgcgautc aaaatgattc taactcccct acg                             33

<210> SEQ ID NO 41
<211> LENGTH: 33
<212> TYPE: DNA
<213> ORGANISM: Saccharomyces cerevisiae

<400> SEQUENCE: 41
agcgatacgu atgtacgcat cgtacccaga gca                             33

<210> SEQ ID NO 42
```

-continued

```
<211> LENGTH: 32
<212> TYPE: DNA
<213> ORGANISM: Saccharomyces cerevisiae

<400> SEQUENCE: 42
cacgcgautc acaatagcat ttccaaagga tt                                32

<210> SEQ ID NO 43
<211> LENGTH: 36
<212> TYPE: DNA
<213> ORGANISM: Saccharomyces cerevisiae

<400> SEQUENCE: 43
agcgatacgu atgttcaatg tctgtaggcg acaatg                            36

<210> SEQ ID NO 44
<211> LENGTH: 33
<212> TYPE: DNA
<213> ORGANISM: Saccharomyces cerevisiae

<400> SEQUENCE: 44
cacgcgautc acggattctt tttcaaaata ttg                               33

<210> SEQ ID NO 45
<211> LENGTH: 34
<212> TYPE: DNA
<213> ORGANISM: Saccharomyces cerevisiae

<400> SEQUENCE: 45
atcaacgggu atggtgggac agcgaaacct cata                              34

<210> SEQ ID NO 46
<211> LENGTH: 36
<212> TYPE: DNA
<213> ORGANISM: Saccharomyces cerevisiae

<400> SEQUENCE: 46
cgtgcgautt atgtgtaact gtcaatattc tccaaa                            36

<210> SEQ ID NO 47
<211> LENGTH: 41
<212> TYPE: DNA
<213> ORGANISM: Saccharomyces cerevisiae

<400> SEQUENCE: 47
agcgatacgu atgaatgcat tgaatactga ttcagataac g                      41

<210> SEQ ID NO 48
<211> LENGTH: 36
<212> TYPE: DNA
<213> ORGANISM: Saccharomyces cerevisiae

<400> SEQUENCE: 48
cacgcgautt atttcatgtt tcttttcttc aaaacg                            36

<210> SEQ ID NO 49
<211> LENGTH: 36
<212> TYPE: DNA
<213> ORGANISM: Saccharomyces cerevisiae

<400> SEQUENCE: 49
atcaacgggu atgacttccc aacatgagtg gatagc                            36
```

```
<210> SEQ ID NO 50
<211> LENGTH: 33
<212> TYPE: DNA
<213> ORGANISM: Saccharomyces cerevisiae

<400> SEQUENCE: 50
cgtgcgautc agtcatcatg aaccagtgtc ttt                              33

<210> SEQ ID NO 51
<211> LENGTH: 31
<212> TYPE: DNA
<213> ORGANISM: Saccharomyces cerevisiae

<400> SEQUENCE: 51
cgtgcgaugc acacaccata gcttcaaaat g                                31

<210> SEQ ID NO 52
<211> LENGTH: 31
<212> TYPE: DNA
<213> ORGANISM: Saccharomyces cerevisiae

<400> SEQUENCE: 52
agcgatacgu atgtcgaagg gaaaggtttt g                                31

<210> SEQ ID NO 53
<211> LENGTH: 34
<212> TYPE: DNA
<213> ORGANISM: Saccharomyces cerevisiae

<400> SEQUENCE: 53
cacgcgautt atttcttctg tccataagct ctgg                             34

<210> SEQ ID NO 54
<211> LENGTH: 37
<212> TYPE: DNA
<213> ORGANISM: Saccharomyces cerevisiae

<400> SEQUENCE: 54
agcgatacgu atgttaacac ccttaagcta tcctatc                          37

<210> SEQ ID NO 55
<211> LENGTH: 30
<212> TYPE: DNA
<213> ORGANISM: Saccharomyces cerevisiae

<400> SEQUENCE: 55
cacgcgautt acatggtgtc gtggaaggtg                                  30

<210> SEQ ID NO 56
<211> LENGTH: 29
<212> TYPE: DNA
<213> ORGANISM: Saccharomyces cerevisiae

<400> SEQUENCE: 56
atcaacgggu atgttgaagg ctgcgttgc                                   29

<210> SEQ ID NO 57
<211> LENGTH: 27
<212> TYPE: DNA
<213> ORGANISM: Saccharomyces cerevisiae

<400> SEQUENCE: 57
cgtgcgautc actcggcgca gatgacg                                     27
```

<210> SEQ ID NO 58
<211> LENGTH: 42
<212> TYPE: DNA
<213> ORGANISM: Saccharomyces cerevisiae

<400> SEQUENCE: 58
atcgaagcgg ccgcaaaaca atgccaaaga ttgttatttt gc                              42

<210> SEQ ID NO 59
<211> LENGTH: 30
<212> TYPE: DNA
<213> ORGANISM: Saccharomyces cerevisiae

<400> SEQUENCE: 59
atcgtcgagc tcttaatgct cacgcgcatg                                            30

<210> SEQ ID NO 60
<211> LENGTH: 59
<212> TYPE: DNA
<213> ORGANISM: Saccharomyces cerevisiae

<400> SEQUENCE: 60
caacaacgta tctaccaacg gaatgcgtgc gatttaatgc tcacgcgcat ggttgatag            59

<210> SEQ ID NO 61
<211> LENGTH: 60
<212> TYPE: DNA
<213> ORGANISM: Saccharomyces cerevisiae

<400> SEQUENCE: 61
caacaacgta tctaccaacg gaatgcgtgc gattcaggca ttgagaattt cgtcgagatg          60

<210> SEQ ID NO 62
<211> LENGTH: 55
<212> TYPE: DNA
<213> ORGANISM: Saccharomyces cerevisiae

<400> SEQUENCE: 62
cttttcggtt agagcggatg aatgcacgcg ttaccagtaa tgctccgctg tcata               55

<210> SEQ ID NO 63
<211> LENGTH: 2752
<212> TYPE: DNA
<213> ORGANISM: Saccharomyces cerevisiae

<400> SEQUENCE: 63
gaattcgcat agcaatctaa tctaagtttt aattacaagc ggccgcaaaa caatgtcaga          60
aagattccca acgatgtcg atccaataga acaagagac tggttacaag caatagaaag          120
tgtcataaga gaagaaggtg ttgaaagagc acaatatttg atcgatcaat gttagccga           180 agctagaaaa ggtggtgtca atgttgctgc aggtactggt atctctaact acatcaacac          240
aataccagtt gaagaacaac cagaataccc tggtaatttg gaattagaaa gaagaattag          300
atcagcaatc agatggaacg ccattatgac cgttttgaga gcttccaaaa aggatttgga          360
attaggtggt catatggcaa gttttcaatc ttcagccact atatacgatg tatgtttcaa          420 ccacttttc agagcaagaa acgaacaaga tggtggtgac ttagtatact ttcaaggtca          480
tatttctcca ggtgtctatg caagagcctt cttggaaggt agattaacac aagaacaatt          540
ggataacttc agcaagaag tacatggtaa cggtttatcc agttatccac acctaaatt          600 gatgccagaa ttttggcaat tccctactgt ctctatgggt ttaggtccta ggtgcaat          660

```
ctaccaagcc aaattcttga agtatttgga acatagaggt ttgaaggata catctaagca    720
aaccgtttac gcattttgg gtgacggtga aatggacgaa ccagaatcaa aaggtgctat    780
aactatcgca acaagagaaa agttggataa tttggtattc gtcattaatt gcaacttgca    840
aagattagac ggtcctgtta ctggtaacgg taaaattata aacgaattgg aaggtatctt    900
tgaaggtgct ggttggaatg taatcaaggt catgtggggt tctagatggg atgaattgtt    960
aagaaaagac acttctggta aattgatcca attgatgaac gaaacagtcg atggtgacta   1020
tcaaaccttt aaatcaaagg atggtgcata cgttagagaa catttctttg gtaaatatcc   1080 agaaccgcc gctttagtag ctgattggac tgacgaacaa atctgggcat gaatagagg     1140 tggtcatgat ccaagaaaa tatatgcagc cttaaaaag gctcaagaaa ccaagggtaa     1200
agctactgtt atattagcac acacaatcaa aggttacggt atgggtgacg ctgcagaagg   1260
taaaaatatc gcacatcaag tcaaaagat gaacatggat ggtgttagac acatcagaga    1320
cagattcaat gttccagtat ccgatgctga catcgaaaaa ttgccataca tcacatttcc   1380
tgaaggtagt gaagaacata cctacttgca cgcacaaaga caaaaattgc atggttattt   1440
gccatctaga caacctaact ttactgaaaa gttggaatta ccatcattgc aagatttcgg   1500
tgctttgttg gaagaacaat ctaaggaaat ctcaactaca attgcctttg taagagcttt   1560
gaacgtcatg ttgaaaaata agtccattaa ggatagattg gttcctatca ttgccgacga   1620
agctagaact tttggtatgg aaggtttgtt cagacaaatt ggtatataca gtccaaatgg   1680
tcaacaatat acacctcaag atagagaaca agttgcctat tacaaagaag acgaaaaggg   1740
tcaaatattg caagaaggta taaacgaatt aggtgcaggt tgttcctggt tggccgctgc   1800
aacttcttac tcaacaaaca acttaccaat gatcccttc tacatctatt acagtatgtt    1860
cggtttccaa agaattggtg acttgtgctg ggccgctggt gaccaacaag ctagaggttt    1920
cttgataggt ggtacatctg gtagaaccac tttgaatggt gaaggtttac aacatgaaga   1980
tggtcattcc cacattcaaa gtttgaccat tccaaactgt atatcatatg atcctgctta   2040
cgcatatgaa gtcgctgtta taatgcatga cggtttagaa agaatgtacg gtgaaaagca   2100
agaaaacgtt tactactaca tcacaacctt gaatgaaaac tatcacatgc agccatgcc    2160 tgaaggtgct gaagaaggta tcagaaaagg tatctataag ttagaaacaa tcgaaggttc   2220
caagggtaaa gttcaattgt taggttccgg tagtatttta agacatgtta gagaagcagc   2280
cgaaatattg gctaaagatt acggtgttgg ttctgacgtt tattccgtaa ccagtttcac   2340
tgaattagca agagatggtc aagactgcga aagatggaat atgttgcacc cattagaaac   2400
tccaagagtt ccttacattg ctcaagtaat gaacgatgcc cctgctgttg catctactga   2460
ctatatgaaa ttgtttgccg aacaagtcag aacatacgtt ccagctgatg actatagagt   2520
cttaggtacc gatggtttcg gtagatctga ctcaagagaa aatttgagac atcactttga   2580
agttgatgca tcatatgttg tagtcgctgc attgggtgaa ttagccaaga gaggtgaaat   2640
tgataaaaag gttgtagccg acgcaatagc aaagttcaac atagacgctg acaaggtaaa   2700
ccctagatta gcctgagagc tcttaattaa caattcttcg ccagaggaat tc           2752
```

<210> SEQ ID NO 64
<211> LENGTH: 1981
<212> TYPE: DNA
<213> ORGANISM: Saccharomyces cerevisiae

<400> SEQUENCE: 64

```
gaattcgcat agcaatctaa tctaagtttt aattacaagc ggccgcaaaa caatggcaat      60
agaaatcaaa gttccagaca taggtgcaga cgaagtagaa ataacagaaa tcttagtcaa     120
agttggtgac aaggtagaag ctgaacaatc tttgattact gttgaaggtg acaaagcatc     180
catggaagtt ccaagtcctc aagctggtat agtaaaggaa attaaagttt ctgtaggtga     240
caagacccaa actggtgcct aatcatgat  ttttgattca gctgacggtg ctgcagacgc     300
cgctccagca caagccgaag aaaagaaaga agcagcccca gctgcagccc tgctgcagc      360
cgctgcaaaa gatgtcaatg ttcctgatat cggttcagac gaagtagaag tcactgaaat     420
tttggttaaa gtaggtgaca aggtagaagc agaacaatct ttaattacag tcgaaggtga     480
caaagcatct atggaagtcc cagccccttt tgctggtaca gttaaagaaa tcaaggtcaa     540
tgttggtgac aaggtttcta ccggttcatt gattatggtt ttcgaagtag caggtgaagc     600
aggtgccgct gcaccagccg ctaaacaaga agctgcccct gctgcagccc agctcctgc      660
tgcaggtgtt aaggaagtaa acgtcccaga tattggtggt gacgaagttg aagtaaccga     720
agtcatggtc aaggtaggtg acaaggttgc cgctgaacaa tccttaatta ctgtagaagg     780
tgacaaagct agtatggaag ttccagctcc ttttgcaggt gttgtaaaag aattgaaggt     840
caacgttggt gacaaagtta agactggttc cttaataatg atcttcgaag ttgaaggtgc     900
tgccccagct gcagcccctg caaaacaaga agctgcagcc ccagctcctg ctgcgaaggc     960
tgaagcacca gccgctgcac ctgccgctaa agctgagggt aaatctgaat tgccgaaaa   1020
tgatgcttat gttcatgcaa caccattgat tagaagatta gcaagagaat ttggtgttaa   1080
cttggctaaa gtaaagggta ccggtagaaa gggtagaatt ttaagagaag atgtccaagc   1140
atatgttaaa gaagccataa agagagctga agctgcccca gctgctacag gtggtggtat   1200
acctggcatg ttgccatggc ctaaagttga cttttctaag ttcggtgaaa ttgaagaagt   1260
tgaattgggt agaatacaaa agatttctgg tgcaaatttg tcaagaaact gggtcatgat   1320
accacatgtt actcactttg ataaaacaga catcaccgaa ttggaagcct ttagaaaaca   1380
acaaaatgaa gaagccgcta agagaaagtt agatgttaag atcacaccag tcgttttatt   1440
tatgaaggca gttgcagccg ctttggaaca aatgcctaga ttcaactctt cattatctga   1500
agacggtcaa agattgacct tgaagaaata catcaacatc ggtgtagctg tcgatactcc   1560
aaacggtttg gtagtccctg ttttttaaaga cgtcaataag aaaggtatca tcgaattgtc   1620
cagagaatta atgacaatca gtaaaaaggc tagagatggt aaattaactg caggtgaaat   1680
gcaaggtggt tgttttacaa tatccagtat cggtggtttg ggtactacac atttcgcacc   1740
aatagtaaat gcacctgaag tcgccatctt aggtgtttct aaatcagcta tggaaccagt   1800
atggaacggt aaagaatttg tcccaagatt gatgttgcct atttccttaa gtttcgatca   1860
cagagttata gatggtgctg acggtgccag attcatcacc atcatcaaca cactttatc   1920
cgatattaga agattagtca tgtaagagct cttaattaac aattcttcgc cagaggaatt   1980
c                                                                  1981

<210> SEQ ID NO 65
<211> LENGTH: 1512
<212> TYPE: DNA
<213> ORGANISM: Saccharomyces cerevisiae

<400> SEQUENCE: 65
gaattcatta tctacttttt acaacaaata taaacaagg atccaaaaca atgtcaacag       60
aaatcaagac tcaagtcgta gtattaggtg ccggtccagc aggttactcc gcagcattca      120
```

```
gatgtgcaga cttaggtttg gaaacagtaa tagtcgaaag atacaacacc ttgggtggtg        180 tttgttaaa cgtaggttgc atcccatcta aagcattgtt acatgttgcc aaggtaattg         240
aagaagccaa agcattggca gaacacggta tagttttgg tgaacctaag accgatatcg         300
acaagatcag aacttggaag gaaaaggtta ttaatcaatt gactggtggt ttagctggta        360
tggcaaaggg tagaaaagtt aaggttgtaa acggtttggg taaattcaca ggtgcaaata        420
ccttagaagt cgaaggtgaa aacggtaaaa cagttataaa tttcgataac gctattatag        480
ctgcaggttc cagaccaatc caattgccat tcattcctca tgaagatcct agaatttggg        540
atagtacaga cgctttggaa ttaaaggaag taccagaaag attgttagtc atgggtggtg        600
gtatcattgg tttggaaatg ggtaccgttt accacgcttt aggttcccaa attgatgtcg        660
ttgaaatgtt tgaccaagtt atacctgccg ctgataaaga catcgttaag gtttttacta        720
agagaataag taaaaagttc aatttgatgt tagaaaccaa ggtcactgcc gttgaagcta        780
aagaagatgt tatctatgtt acaatggaag gtaaaaaggc cccagctgaa cctcaaagat        840
acgatgctgt cttggttgca atcggtagag ttccaaatgg taaaaatttg gacgctggta        900
aagccggtgt agaagtcgat gacagaggtt ttattagagt agataagcaa ttgagaacta        960
acgtcccaca tattttcgca ataggtgaca tcgttggtca acctatgtta gcccacaaag        1020
gtgtacatga aggtcacgtc gcagccgaag ttattgctgg taaaaagcat tacttcgatc        1080
caaaggttat tccttctata gcttacactg aaccagaagt agcatgggtc ggtttgacag        1140
aaaaagaagc caaagaaaag ggtatttcat atgaaactgc tacatttcct tgggctgcat        1200
ctggtagagc aatcgcctca gattgtgctg acggtatgac caagttaatc ttcgataagg        1260
aatctcatag agttatcggt ggtgcaattg taggtactaa tggtggtgaa ttgttaggtg        1320
aaataggttt ggctatcgaa atgggttgcg atgccgaaga cattgcttta actatacatg        1380
cacacccaac attgcatgaa tcagttggtt tagctgctga agtatttgaa ggtagtataa        1440
ccgatttgcc taaccctaaa gccaagaaga agtaggtcga catggaacag aagttgattt        1500
ccgaaggaat tc                                                            1512
```

<210> SEQ ID NO 66
<211> LENGTH: 1104
<212> TYPE: DNA
<213> ORGANISM: Saccharomyces cerevisiae

<400> SEQUENCE: 66

```
gaattcatta tctacttttt acaacaaata taaaacaagg atccaaaaca atgtccacct          60
tgagattatt gattagtgac tcctatgacc catggttcaa cttagccgtc gaagaatgta        120
tcttcagaca aatgccagct acccaaagag tttattttt gtggagaaat gcagatacag        180
ttgtaattgg tagagcccaa aatccatgga aggaatgtaa cactagaaga atggaagaag        240
acaatgttag attggctaga agatcttcag gtggtggtgc agtattccat gatttgggta        300
acacttgctt tacattcatg gctggtaaac ctgaatatga caagaccatc tctacttcaa        360
tagtattgaa cgccttgaac gctttaggtg tctccgccga agctagtggt agaaatgatt        420
tggtcgttaa gactgttgaa ggtgacagaa agtatccgg tagtgcatat agagaaacca        480
aggatagagg ttttcatcac ggtactttgt tattgaatgc cgatttgtcc agattagcta        540
actacttgaa cccagacaaa aagaaattag ctgcaaaggg tatcacatct gtaagatcaa        600
gagtcacaaa cttgaccgaa ttattgcctg gtataacaca tgaacaagtt tgtgaagcta        660
```

-continued

```
tcaccgaagc attttcgcc cactatggtg aaagagttga agcagaaatc atctctccaa      720
ataagactcc agattttgcct aactttgctg aaacattcgc aagacaatcc agttgggaat    780
ggaatttgg tcaagcacct gccttctcac atttgttgga tgaaagattc acttggggtg     840
gtgtcgaatt gcatttcgac gttgaaaaag gtcacataac tagagcacaa gttttacag    900
attctttgaa cccagcccct ttggaagcat tggcaggtag attgcaaggt tgtttataca    960
gagccgatat gttacaacaa gaatgcgaag cattgttggt tgacttccct gaacaagaaa   1020
aggaattgag agaattgagt gcctggatgg ctggtgctgt aagatagctc gagtaagctt   1080
ggtaccgcgg ctagctaaga attc                                           1104
```

<210> SEQ ID NO 67
<211> LENGTH: 2696
<212> TYPE: DNA
<213> ORGANISM: Saccharomyces cerevisiae

<400> SEQUENCE: 67

```
ataagaatgc ggccgcatgg aacaagacat gcaagacatg caagacttgg acccaatcga     60
aactcaagaa tggttggact ctttggaatc tgttttggac cacgaaggtg aagaaagagc    120
tcactacttg ttgactagaa tgggtgaatt ggctactaga actggtactc aattgccata    180
cgctatcact actccataca gaaacactat cccagttact cacgaagctc acatgccagg   240
tgacttgttc atgaaagaa gaatcagatc tttggttaga tggaacgctt ggctactgt     300
tatgagagct aacaagaagg acccagactt gggtggtcac atctctactt tcgcttcttc   360
tgctactttg tacgacatcg gtttcaacta cttcttccaa gctccaactg ctgaacacgg   420
tggtgacttg atctacttcc aaggtcacgc tgcgccaggt gtatacgcaa gagctttctt   480
ggaaggtaga atctctgaag ctcaattgca acaattcaga caagaagttg acggtgacgg   540
tttgtcttct tacccacacc cacacttgat gccagacttc tggcaattcc caactgtttc   600
tatgggtttg gtccaatcc aagctatcta ccaagctaga ttcatgaagt acttggaaca   660
cagaggtttc atcccagcgg gtaagcagaa ggtgtggtgc ttcatgggcg acggtgaatg   720
tgacgaacca gaatctttgg gtgctatctc tttggctggt agagaaaagt ggacaacttt   780
gatcttcgtt atcaactgta acttgcaaag attggacggt ccagttagag gtaacggtaa   840
gatcatccaa gaactcgagg gtgtgttcag aggggctcaa tggaacgtta caaggttgt   900
ttggggtaga ttctgggacc cattgttcgc taaggaccac gctggtttgt tgcaacaaag   960
aatggacgaa gttgttgacg gtgactacca aaactacaag gctaaggacg tgctttcgt   1020
tagaaagcac ttcttcggtg ctagaccaga attgttggaa ttggttaagg acatgtctga   1080
cgaagacatc tggaagttga acagaggtgg tcacgaccca acaaggtttt acgctgctta   1140
ccaccaagct gttaaccacc aaggtcaacc atctgttatc ttggctaaga ctatcaaggg   1200
ttacggtact ggtgctggtg aagctaagaa catcgctcac aacgttaaga aggttgatgt   1260
agaaagcttg aagttgttcc gtgacaagtt cgacgttcca ttgaaggacg aagaattgga   1320
agacttgcca ttctacagac cagacgaaaa ctctccagaa atgaagtact tgagatctag   1380
aagagaagct ttgggtggtt tcgttccaca aagaagaaga agtctatct ctatcccaac   1440
tccaccattg gactctttga aggctatctt ggacggtact ggtgacagag aaatctctac   1500
tactatggct ttcgttagaa tcttggctca attggttaag gacaaggaat gggttctag   1560
aatcgttcca atcatcccag acgaagctag aactttcggt atggaaggta tgttcagaca   1620
attgggtatc tactcttctg ttggtcaatt gtacgaacca gttgacaagg accaagttat   1680
```

```
gttctacaga gaagacaaga agggtcaaat cttggaagaa ggtatcaacg aagctggtgc    1740
tatgtcttct tggatctctg ctgctactgc ttactctaac cacaaccaac caatgttgcc    1800
attctacgtt ttctactcta tgttcggttt ccaaagaatc ggtgacttgg cttgggctgc    1860
tggtgactcg caagcgagag gcttcttgat cggtggcact gctggtagaa ctactttgaa    1920
cggtgaaggt ttgcaacacg aagacggtca ctctcacatc ttggcttcta ctatcccaaa    1980
ctgtagaact tacgacccaa cttacgctta cgaaatggct gttatcatca gagaaggtat    2040
cagacaaatg actgaagaac aacaaaacgt tttctactac atcactgcta tgaacgaagc    2100
ttacactcaa ccagctatgc cagaaggtgc tgaagctggt atcgttaagg gtatgtactt    2160
gttggaagaa gacaagagag acgctgctca ccacgttcaa ttgttgggtt ctggtactat    2220
cttgagagaa gttagagaag ctgctaagat cttgagagaa gactacaacg ttgctgctga    2280
cgtttggtct gttacttctt tcaacgaatt gagaagaaac ggtttggctg ttgaaagaag    2340
aaacagattg cacccagaac aaaagccaga acaatcttac gttgaacaat gtttgaacgg    2400
tagaaagggt ccagttgttg cttctactga ctacatgaag ttgttcgctg accaaatcag    2460
acaatgggtt ccatctagag aatacaaggt tttgggtact gacggtttcg gtagatctga    2520
cactagaaag aagttgagac acttcttcga agttgacaga tactgggttg ttttggctgc    2580
tctcgaggct ctcgctgaca gaggcgacat cgaagctaag gttgttgctg aagctatcgc    2640
taagttcggt atcgacccag acaagagaaa cccattggac tgttaattaa ttaagg       2696
```

<210> SEQ ID NO 68
<211> LENGTH: 1946
<212> TYPE: DNA
<213> ORGANISM: Saccharomyces cerevisiae

<400> SEQUENCE: 68

```
ataagaatgc ggccgcatgt ctgaaatcat cagagttcca gacatcggtg gtgacggtga      60
agttatcgaa ttgttggtta agactggtga cttgatcgaa gtagagcaag gcttggttgt     120
tttggagtct gctaaggctt ctatggaagt tccatctcca aaggctggtg ttgttaagtc     180
tgtttctgtt aagttgggtg acaagttgaa ggaaggtgac gctatcatcg aattggaacc     240
agctgctggt gctgctgctg ctccagctga agctgctgct gttccagctg ctccaactca     300
agctgttgac gaagctgaag ctccatctcc aggtgcttct gctactccag ctccagctgc     360
tgcttctcaa gaagttagag ttccagacat cggttctgct ggtaaggcta gagttatcga     420
agttttggtt aaggctggtg accaagttca agcggagcag tcgttgatcg tgctagagtc     480
tgacaaggct tctatggaaa tcccatctcc agcttctggt gttgttgaat ctgttgctat     540
ccaattgaac gctgaagttg gtactggtga cttgatcttg actttgagaa ctactggtgc     600
tcaagctcaa ccaactgctc agctgctgc tgctgctgct tctccagctc agctccatt      660 ggctccagct gctgctggtc acaagaagt taaggttcca gacatcggtt ctgctggtaa     720
ggctagagtt atcgaagttt tggttaaggc tggtgaccaa gttcaagcgg agcagtcgtt     780
gatcgtgcta gagtctgaca aggcttctat ggaaatccca tctccagctg ctggtgttgt     840
tgaatctgtt gctgttcaat gaacgctga agttggtact ggtgaccaaa tcttgacttt     900
gagagttgct ggtgctgctc agctgctgc tccagctcca gctgctgctc agctaagcc      960 agctgctgct ccagctgctg ctgctccagc tccagctcca gttggtgctc atctagaaa     1020 cggtgctaag gttcacgctg gtccagctgt tagacaattg gctagagaat cggtgttga     1080
```

-continued

| | |
|---|---|
| attggctgct atcaactcta ctggtccaag aggtagaatc ttgaaggaag acgttcaagc | 1140 |
| ttacgttaag gctatgatgc aaaaggctaa ggaagctcca gctgctggtg ctgcttctgg | 1200 |
| tgctggtatc ccaccaatcc caccagttga cttcgctaag tacggtgaaa tcgaagaagt | 1260 |
| tccaatgact agattgatgc aaatcggtgc tactaacttg cacagatctt ggttgaacgt | 1320 |
| tccacacgtt actcaattcg aatctgctga catcactgaa ttggaagctt tcagagttgc | 1380 |
| tcaaaaggct gttgctgaaa aggctggtgt taagttgact gttttgccat tgttgttgaa | 1440 |
| ggcttgtgct tacttgttga aggaattgcc agacttcaac tcttctttgg ctccatctgg | 1500 |
| tcaagctttg atcagaaaga agtacgttca atcggtttc gctgttgaca ctccagacgg | 1560 |
| tttgttggtt ccagttatca gaaacgttga ccaaaagtct tgttgcaat ggctgctga | 1620 |
| agctgctgaa ttggctgaaa aggctagatc taagaagttg ggtgctgacg ctatgcaagg | 1680 |
| cgcgtgcttc accatctctt ctttgggtca catcggcggc actgcgttca ctccaatcgt | 1740 |
| taacgctcca gaagttgcta tcttgggtgt ttctaaggct tctatgcaac cagtttggga | 1800 |
| cggtaaggct ttccaaccaa gattgatgtt gccattgtct ttgtcttacg accacagagt | 1860 |
| tatcaacggt gctgctgctg ctagattcac taagagattg ggtgacttgt tggctgacat | 1920 |
| cagagctatc ttgttgtaag agctcg | 1946 |

<210> SEQ ID NO 69
<211> LENGTH: 1453
<212> TYPE: DNA
<213> ORGANISM: Saccharomyces cerevisiae

<400> SEQUENCE: 69

| | |
|---|---|
| cgggatccat gtctcaaaag ttcgacgtta tcgttatcgg tgctggtcca ggtggttacg | 60 |
| ttgctgctat caagtctgct caattggggtt tgaagactgc tttgatcgaa agtacaagg | 120 |
| gtaaggaagg taagactgct ttgggtggta cttgtttgaa cgttggttgt atcccatcta | 180 |
| aggctttgtt ggactcttct tacaagttcc acgaagctca cgaatctttc aagttgcacg | 240 |
| gtatctctac tggtgaagtt gctatcgacg ttccaactat gatcgctaga aaggaccaaa | 300 |
| tcgttagaaa cttgactggt ggtgttgctt ctttgatcaa ggctaacggt gttactttgt | 360 |
| tcgaaggtca cggtaagttg ttggctggta agaaggttga agttactgct gctgacggtt | 420 |
| cttctcaagt tttggacact gaaaacgtta tcttggcttc tggttctaag ccagttgaaa | 480 |
| tcccaccagc tccagttgac caagacgtta tcgttgactc tactggtgct ttggacttcc | 540 |
| aaaacgttcc aggtaagttg ggtgttatcg gtgctggtgt tatcggtttg gaattgggtt | 600 |
| ctgtttgggc tagattgggt gctgaagtta ctgttttgga agctatggac aagttcttgc | 660 |
| cagctgttga cgaacaagtt gctaaggaag ctcaaaagat cctcactaag caaggtctca | 720 |
| agatcttgct cggtgctaga gttactggta ctgaagttaa gaacaagcaa gttactgtta | 780 |
| agttcgttga cgctgaaggt gaaaagtctc aagctttcga caagttgatc gttgctgttg | 840 |
| gtagaagacc agttactact gacttgttgg ctgctgactc tggtgttact ttggacgaaa | 900 |
| gaggtttcat ctacgttgac gactactgtg ctacttctgt tccaggtgtt tacgctatcg | 960 |
| gtgacgttgt tagaggtgct atgttggctc acaaggcttc tgaagaaggt gttgttgttg | 1020 |
| ctgaaagaat cgctggtcac aaggctcaaa tgaactacga cttgatccca gctgttatct | 1080 |
| acactcaccc agaaatcgct ggtgttggta agactgaaca agctttgaag gctgaaggtg | 1140 |
| ttgctatcaa cgttggtgtt ttcccattcg ctgcttctgg tagagctatg gctgctaacg | 1200 |
| acactgctgg tttcgttaag gttatcgctg acgctaagac tgacagagtt ttgggtgttc | 1260 |

```
acgttatcgg tccatctgct gctgaattgg ttcaacaagg tgctatcgct atggaattcg   1320
gtacttctgc tgaagacttg ggtatgatgg ttttcgctca cccagctttg tcggaggctc   1380
tccatgaggc tgcgctcgct gtttctggcc acgctatcca cgttgctaac agaaagaagt   1440
aagtcgacgt cgg                                                      1453
```

<210> SEQ ID NO 70
<211> LENGTH: 1139
<212> TYPE: DNA
<213> ORGANISM: Saccharomyces cerevisiae

<400> SEQUENCE: 70

```
cgagctcatg gctaaggcta agaagcaaaa gccaatcgac ttcaaggaat tgatggctaa     60
ggttgacgct gacttcccaa ctttccaaat cttggaccaa gacggtaaga tcgttaacga    120
agacttggtt ccagacttgt ctgacgaaga attggttgaa ttgatgacta gaatggtttg    180
gtctagagtt ttggaccaaa gatctactgc tttgaacaga caaggtagat tgggtttctt    240
cgctccaact gctggtcaag aagcttctca attggcttct caattcgcta tggaaaagga    300
agactacttg ttgccaggtt acagagacgt tccacaattg gttcaacacg gtttgccatt    360
gagagaagct ttcttgtggt ctagaggtca cgttgctggt aactactacg ctgaagactt    420
gaacgctttg ccaccacaaa tcatcatcgg tgctcaatac atccaagctg ctggtgttgc    480
tttgggtttg aagaagagag gtaaggaaaa cgttgttttc acttacactg gtgacggtgg    540
ttcttctcaa ggtgacttct acgaagctat caacttcgct ggtgcttacc aagctaacgg    600
tgttttcatc atccaaaaca cggtttcgc tatctctact ccaagagaaa agcaaactgc    660
tgctaagact ttggctcaaa aggctgttgc tgctggtatc ccaggtatcc aagttgacgg    720
tatggaccca ttggctgttt acgctatcgc taaggaagct agagactggt ctgctgctgg    780
taacggtcca gttctcatag aaactctcac ttacagatac ggtccacaca ctttgtctgg    840
tgacgaccca actagataca gatctaagga aatggacgac gaatgggttc aaaaggaccc    900
attgactaga ttcagaaagt acctcactga caagggcttg tggtctgaag cgaaggaaga    960
agaaatcatc gaaaagacta aggaagaaat caaggttgct atcgctgaag ctgacaaggc   1020
tccaaagcaa aaggtttctg acttcttgaa gaacatgttc gaagttcaac acaaactat   1080 caaggaacaa atcgctttct acgaagctaa ggaatctaag taagcggccg ctaaactat   1139
```

<210> SEQ ID NO 71
<211> LENGTH: 995
<212> TYPE: DNA
<213> ORGANISM: Saccharomyces cerevisiae

<400> SEQUENCE: 71

```
cgggatccat ggctcaaaag actatgatcc aagctatcac tgacgctttg gctttggaat     60
tggaaaagga cgaaaacgtt ttgatcttcg gtgaagacgt tggtaacaac ggtggtgttt    120
tcagagctac tgaaggtttg caagaaaagt tcggtgaaga cagagttttc gacactccat    180
tggctgaatc tggtatcggt ggtttggctt tcggtttggc tttgcaaggt tacagaccag    240
ttccagaaat ccagttcttt ggtttcgtct tcgaagtgtt cgacgaaatc gttggtcaaa    300
tggctagaac tagatacaga atgggtggta ctagaaacat gccaatcact gttagagctc    360
cattcggtgg tggtgttcac actccagaat tgcactctga caacttggaa ggtttgatcg    420
ctcaatctcc aggtgttaga gttgttatcc catctaaccc atacgacgct aagggtttgt    480
```

| | |
|---|---|
| tgatctcttc tatcagatct aacgatccag ttgtatacct ggaacacatg aagttgtaca | 540 |
| gatctttcag agaagaagtt ccagacgaag cttacgaagt tccattggac aaggctgctg | 600 |
| ttactagaga aggtactgac gtttctatca tcacttacgg tgctatggtt agagaagcta | 660 |
| tcaaggctgc tgactctttg gctaaggaca acatctctgc tgaaatcatc gacttgagaa | 720 |
| ctgttgctcc attggacgtt gaaactatca tcaactctgt tgaaaagact ggtagagttg | 780 |
| ttgttgttca agaagctcaa aagcaagctg gtgttggtgc tatggttgtt tctgaaatct | 840 |
| ctgagcgtgc tgtgctatct ttggaagctc aatcggtag agtttctgct ccagacacta | 900 |
| tcttcccatt cggtcaagct gaaaacatct ggttgccaaa cgctaaggac atcgaagcta | 960 |
| aggctagaga aatcgttgaa ttctaactcg agcgg | 995 |

<210> SEQ ID NO 72
<211> LENGTH: 1643
<212> TYPE: DNA
<213> ORGANISM: Saccharomyces cerevisiae

<400> SEQUENCE: 72

| | |
|---|---|
| cgagctcatg gcttaccaat tcaagttgcc agacatcggt gaaggtatcg ctgaaggtga | 60 |
| aatcgttaag tggttcgtta agccaggtga cactatcaac gaagacgaca ctttgttgga | 120 |
| agttcaaaac gacaagtctg ttgaagaaat cccatctcca gttactggta ctgttaagaa | 180 |
| catcgttgtt ccagaaggta ctgttgctaa cgtaggcgag tgctaatcg aaatcgacgc | 240 |
| tccaggtcac gaagacaacg acgctgctcc agctgctcca gctcaagaac aaactccagc | 300 |
| tcaaccagct gctgttccaa ctactgaagc tgctggtggt tcttccaat tcaagttgcc | 360 |
| agacatcggt gaaggtatcg ctgaaggtga aatcgttaag tggttcgtta aggctggtga | 420 |
| cactatcaac gaagacgact ctttgttgga agttcaaaac gacaagtctg ttgaagaaat | 480 |
| cccatctcca gttactggta ctgttaagaa catcgttgtt ccagaaggta ctgttgctaa | 540 |
| cgtaggcgca gtcctcgttg aaatcgacgc tccaggtcac aactctgctg ctccatctgt | 600 |
| tgctgctcca gctactgacg ctccaaaggc tgaagcttct gctccagctg cttctactgg | 660 |
| tgttgttgct gctgctgacc aaacaagag agttttggct atgccatctg ttagacaata | 720 |
| cgctagagaa aaggacgttg acatcactca agttactgct actggtaagg gtggtagagt | 780 |
| tatcaaggct gacatcgacg cttttcgtttc tggtggttct caagctgctc cagctactga | 840 |
| agctgctgct actgaagctg ctccaaaggc tgaagctgct gctccaaagg ctgctccaaa | 900 |
| ggctttcact tctgacttgg gtgaaatgga aactagagaa aagatgactc caactagaaa | 960 |
| ggctatcgct aaggctatgg ttaactctaa gcacactgct ccacacgtta ctttgcacga | 1020 |
| tgaagttgaa gtaagcaagt tgtgggacca cagaaagaag ttcaaggacg ttgctgctgc | 1080 |
| taacggtact aagttgactt tcttgccata cgttgttaag gctttgactt ctactgttca | 1140 |
| aaagttccca atcttgaacg cttctatcga cgacgctgct caagaaatcg tttacaagaa | 1200 |
| ctacttcaac atcggtatcg ctactgacac tgaccacggt ttgtacgttc aaacgttaa | 1260 |
| gaacgctaac actaagtcta tgttcgctat cgctgacgaa atcaacgaaa aggctgcttt | 1320 |
| ggctatcgaa ggtaagttga ctgctcaaga catgagagac ggtactatca ctatctctaa | 1380 |
| catcggttct gttggtggtg gttggttcac tccagttatc aactacccag aagttgctat | 1440 |
| cttgggtgtt ggtactatcg ctcaagaacc agttgttaac gctgacggtg aaatcgttgt | 1500 |
| tggtagaatg atgaagttgt cgctcagctt cgaccacaga atagttgacg gtgctactgc | 1560 |
| tcaaaaggct atgaacaaca tcaagagatt gttggctgac ccagaattgt tgttgatgga | 1620 | aggttaagcg gccgctaaac tat                                              1643

<210> SEQ ID NO 73
<211> LENGTH: 1426
<212> TYPE: DNA
<213> ORGANISM: Saccharomyces cerevisiae

<400> SEQUENCE: 73
cgggatccat ggttgttggt gacttcgcta tcgaattgga cactgttgtt atcggtgctg      60
gtccaggtgg ttacgttgct gctatcagag ctgctgaaat gggtcaaaag gttgctatca     120
tcgaaagaga atacatcggc ggcgtttgcc tcaacgttgg ttgtatccca tctaaggctt     180
tgatcgctgc tggtcaccac taccaagaag ctcaagactc ttctactttc ggtgttactg     240
ctaagggtgt tgaattggac ttcgctaaga ctcaagactg gaaggacaac actgttgtta     300
agtctttgac tggtggtgtt ggtatgttgt tgaagaagca caaggttgaa atcatcgagg     360
gcgaagcgtt cttcgttgac gagaacactt tgagagttat ccacccagac tctgctcaaa     420
cttactcttt caacaacgct atcgttgcta ctggttctag accaatcgaa atcccaggtt     480
tcaagttcgg tggtagagtt ttggactcga ctggtggtct caacttgaag gaggttccaa     540
agaagttcgt tatcatcggt ggtggtgtta tcggtgctga attgggtggt gcttacgcta     600
acttgggttc tgaagttact atcttggaag gttctccatc tatcttgcca acttacgaaa     660
aggacatggt taaggttgtt actgaccact tcaagaagaa gaacgttact atcgttactt     720
ctgctatggc taaggaagct gttgacaacg gtgactctgt tactgttaag tacgaagtta     780
acggtaagga agaatctgtt gaagctgact acgttatggt tactgttggt agaagaccaa     840
acactgacga cttgggtttg gaacaagctg gtgttgaaat cggtgaaaga ggtttgatcc     900
cagttgacaa ccaaggtaga actaacgtta agaacatctt cgctatcggt gacatcgttc     960
caggtgctgc tttggctcac aaggcttctt acgaagctaa gatcgctgct gaagctatct    1020
ctggtaagaa ggttgctgtt gactacaagg ctatgccagc tgttgctttc actgacccag    1080
aattggcttc tgttggtatg actgttgctg aagctaagga agctggtatc gaagctaagg    1140
gttacaagtt cccattcgct ggtaacgtta gagctatctc tttggacaag actgaaggtt    1200
tcatgagatt ggttactact gttgaagaca acgttatcat cggtgctcaa atcgctggtg    1260
ttggtgcttc tgacatgatc tctgaattgg ctttggctat cgaatctggt atgaacgcgg    1320
aagacatcgc tctcactatc cacccacacc catctttggg tgaaatcact atggacactg    1380
ctgaattggc tttgggtttg ccaatccaca tctaagtcga cgtcgg                   1426

<210> SEQ ID NO 74
<211> LENGTH: 254
<212> TYPE: DNA
<213> ORGANISM: Saccharomyces cerevisiae

<400> SEQUENCE: 74
cgggatccat gagcactatc gaagaacgcg ttaagaaaat tatcggcgaa cagctgggcg      60
ttaagcagga agaagttacc aacaatgctt ctttcgttga agacctgggc gcggattctc     120
ttgacaccgt tgagctggta atggctctgg aagaagagtt tgatactgag attccggacg     180
aagaagctga gaaaatcacc accgttcagg ctgccattga ttacatcaac ggccaccagg     240
cgtaactcga gcgg                                                       254

<210> SEQ ID NO 75

<211> LENGTH: 1628
<212> TYPE: DNA
<213> ORGANISM: Saccharomyces cerevisiae

<400> SEQUENCE: 75

| | | | | | |
|---|---|---|---|---|---|
| ataagaatgc | ggccgcatga | accagtatgt | aaatgatcca | tccaattatc | agttactaat | 60 |
| taaaaacttg | ctgttttccc | cagttgcttt | caacccagag | caagaaatcg | tctacgctaa | 120 |
| ccaccgccgt | catagctaca | aaacgtttca | tgatcgtgta | agacagtttg | ccaacgcgct | 180 |
| taccaaaatg | ggcgtgaaaa | aaggcgatac | ggttgctgtg | atggattacg | actcccaccg | 240 |
| ttaccttgag | tgttactttg | ctatcccaat | gattggtgcc | aagctgcaca | tgattaacgt | 300 |
| tcgtttgtct | ccagaacaga | tcctttacac | cattgatcat | gccgaagatg | acatcattct | 360 |
| tattcatgaa | gagtttctac | caatcttaga | ccagatcaaa | ggacgcattg | atacggtcac | 420 |
| tcgctacgtt | gtgttacgtg | atgatgaaga | gtgtgagtat | gaacgccttc | ttgaacagga | 480 |
| aagcacggaa | tacaatttcc | cagatttcga | tgaaaacacg | gtggcgacaa | ctttctacac | 540 |
| cacgggtact | acaggatttc | caaaaggcgt | tttcttcacg | catcgtcaac | ttgttcttca | 600 |
| tactatgggt | atattaagca | caatcggtac | caacgcttca | caaggtcgat | tgcatcaagg | 660 |
| tgacatctac | atgccgatta | cgccgatgtt | tcatgtccat | gcttggggc | ttccatatat | 720 |
| ggcaaccatg | cttggtgtta | agcaagtcta | cccgggtaag | tatgttccag | atgttttgct | 780 |
| taacctgatt | gagcaagaga | aggtgacgtt | ctcacactgt | gtgccgacta | ttttgcatct | 840 |
| acttctgagc | tctccaaagt | cgaaggcgat | ggactttct | gggtggaaag | tcgtcattgg | 900 |
| tggtgctgcg | ctaccaaaag | cattatgtaa | atcagctcta | aacgtgata | tcgacgtatt | 960 |
| tgctggttac | ggcatgagtg | agactggacc | tattctttct | atcgtccaat | tgacgcctga | 1020 |
| gcaattagag | ttagatgtcg | accaacaagc | ggaatatcgc | tcgaagacag | gtaagaaagt | 1080 |
| tgcgcttgta | gaagcgtata | ttgtggatga | ggatatgaac | aaactgcctc | atgatggcga | 1140 |
| aaccgctggt | gaaattgttg | ttcgtgcacc | ttggttaaca | cctaactact | acaaagacaa | 1200 |
| caaaaactct | aaagcactat | ggcgtggcgg | ttacctgcac | acaggtgatg | tggcgcatat | 1260 |
| tgatgacgaa | ggctttatca | agatcactga | ccgcgtaaaa | gatatgatta | agatatctgg | 1320 |
| tgagtgggta | agctctttag | agcttgaaga | cattctccac | cagcatcaga | gtgtttccga | 1380 |
| agttgcggtg | attggtatgc | cgcacaacaa | gtggggtgaa | gtgccgttag | ctttggtgac | 1440 |
| attgaaagaa | gacgctcaag | tcacagaaaa | ggaactgtta | ggttttgcga | aagacttcat | 1500 |
| caataaaggg | attcttgcta | gagaagcatt | actacttaaa | gtgaagatag | tggacgagat | 1560 |
| tgctaagacc | agcgttggta | aagtggataa | gaaagaactg | cgtaaacttc | atctgtaatt | 1620 |
| aattaagg | | | | | | 1628 |

<210> SEQ ID NO 76
<211> LENGTH: 3699
<212> TYPE: DNA
<213> ORGANISM: Saccharomyces cerevisiae

<400> SEQUENCE: 76

| | | | | | |
|---|---|---|---|---|---|
| atgggtaaaa | agatgatgac | cactgatggt | aacaccgcaa | ctgctcacgt | cgcttatgct | 60 |
| atgtctgaag | tcgccgctat | ctatcctatt | accccatctt | caactatggg | tgaagaagca | 120 |
| gatgactggg | ctgcacaagg | tagaaagaat | attttttggtc | aaaccttgac | tataagagaa | 180 |
| atgcaatcag | aagctggtgc | cgctggtgct | gttcatggtg | cattagcagc | cggtgctttg | 240 |
| actacaaccct | tcactgcatc | ccaaggtttg | ttgttgatga | tcccaaacat | gtacaaaatt | 300 |

```
agtggtgaat tattgcctgg tgtatttcac gttaccgcta gagcaatcgc tgcacatgca      360
ttgtctattt tcggtgacca ccaagacata tatgccgcta gacaaacagg ttttgcaatg      420
ttagcctcca gttctgtaca agaagctcat gatatggctt tagttgcaca cttggcagcc      480
attgaatcta acgttccttt tatgcatttc tttgatggtt tcagaacatc acacgaaata      540
caaaagattg aagtcttaga ttacgccgac atggcttcct tagtaaatca aaaagccttg      600
gctgagttta gagcaaagag tatgaatcca gaacatcctc acgttagagg tactgctcaa      660
aacccagata tatactttca aggtagagaa gctgcaaatc cttattactt gaaagtacca      720
ggtatcgttg ccgaatacat gcaaaaggta gcttctttaa caggtagatc atacaagttg      780
tttgattatg ttggtgcacc tgacgccgaa agagtaattg tttcaatggg ttcatcctgt      840
gaaactatcg aagaagttat taatcatttg gccgctaagg gtgaaaagat cggtttaatt      900
aaagtaagat tgtacagacc attcgtttct gaagcatttt tcgcagcctt gcctgcatca      960
gccaaagtca ttactgtatt agatagaaca aaggaaccag gtgctccagg tgacccatta     1020
tatttggacg tatgctctgc ttttgttgaa agaggtgaag caatgccaaa aattttggcc     1080
ggtagatacg gtttgggttc taaagaattt tctcctgcaa tggttaagtc tgtctatgat     1140
aatatgtcag gtgctaaaaa gaaccatttt acagttggta tagaagatga cgtcacaggt     1200
acttctttgc cagttgataa tgctttcgca gacactacac ctaaaggtac tattcaatgt     1260
caattttggg gtttaggtgc agatggtaca gttggtgcca ataagcaagc tataaagatt     1320
ataggtgaca acactgactt gtttgctcaa ggttacttct cttatgattc caaaaagagt     1380
ggtggtatca ccatttctca tttgagattc ggtgaaaagc caatccaatc aacttactta     1440
gtaaacagag cagattacgt tgcctgtcac aaccctgctt acgtcggtat ctatgatatt     1500
ttggaaggta tcaaggacgg tggtacattc gtttttaaatt ctccttggtc ttctttggaa     1560
gatatggaca acatttgcc ttcaggtata aagagaacca tcgctaataa gaaattgaag      1620
ttctacaaca tcgatgctgt caagatcgca acagacgtag gtttaggtgg tagaattaac     1680
atgatcatgc aaaccgcatt tttcaaattg gccggtgtct tgccattcga aaaggcagtt     1740
gatttgttga aaaagtctat acacaaagcc tacggtaaaa agggtgaaaa gattgttaag     1800
atgaataccg atgccgttga tcaagctgta acttccttac aagagtttaa atatcctgat     1860
agttggaagg acgccccagc tgaaaccaag gctgaaccta tgactaatga ttttttcaag     1920
aacgttgtca agccaatatt gactcaacaa ggtgacaaat tgcctgtttc tgcttttgaa     1980
gcagacggta gattcccatt gggtacatca caattcgaaa agagaggtgt tgcaatcaac     2040
gtccctcaat gggttccaga aaattgtatt caatgcaacc aatgtgcttt tgtttgtcct     2100
cattctgcta ttttaccagt tttggcaaaa gaagaagaat tagtcggtgc accagccaat     2160
ttcacagcct tggaagctaa gggtaaagaa ttaaagggtt acaagtttag aatacaaatc     2220 aatacccttgg attgcatggg ttgtggtaac tgcgctgaca tttgcccacc taaagaaaag     2280
gcattagtaa tgcaaccatt ggatactcaa agagacgctc aagttcctaa tttggaatac     2340
gctgcaagaa taccagttaa atctgaagtc ttacctagag attccttgaa gggtagtcaa     2400
ttccaagaac cattgatgga atttttctggt gcttgttcag gttgcggtga aactccttat     2460
gtcagagtaa ttacacaatt gttcggtgaa agaatgttca tcgctaatgc aactggttgt     2520
tcatccattt ggggtgcctc tgctccttca atgccataca aaacaaatag attgggtcaa     2580
ggtccagctt ggggtaactc cttatttgaa gatgccgctg aatatggttt tggtatgaac     2640
```

```
atgtctatgt tcgccagaag aacacatttg gctgatttgg cagccaaggc tttggaatcc    2700
gatgcaagtg gtgacgttaa agaagcatta caaggttggt tggccggtaa aaatgatcca    2760
atcaaatcta aggaatacgg tgacaaattg aaaaagttat tggctggtca aaaggatggt    2820
ttattgggtc aaattgctgc aatgtctgat ttgtacacta aaaagtcagt ttggatcttc    2880
ggtggtgacg gttgggcata cgacatcggt tatggtggtt tagatcatgt tttggcttct    2940
ggtgaagatg ttaatgtctt cgtaatggac actgaagttt attcaaacac cggtggtcaa    3000
agttctaaag ctactccaac aggtgcagtt gccaaatttg ctgctgctgg taaaagaaca    3060
ggtaaaaagg atttggcaag aatggttatg acttatggtt acgtttatgt cgctactgtt    3120
tctatgggtt acagtaagca acaattcttg aaggttttga aggaagctga atctttccca    3180
ggtccatctt tggttattgc ttatgcaacc tgtatcaacc aaggtttaag aaagggtatg    3240
ggtaaatccc aagatgtcat gaatactgct gtaaaaagtg gttactggcc tttgttcaga    3300
tatgatccaa gattagccgc tcaaggtaaa aacccatttc aattagattc caaggcacct    3360
gacggtagtg tcgaagaatt tttgatggcc caaaatagat tcgctgtatt agatagatca    3420
tttccagaag acgctaaaag attgagagca caagttgccc atgaattgga tgtcagattc    3480
aaagaattag aacacatggc agccactaat attttgaat ccttcgcccc tgctggtggt    3540
aaagccgatg gtagtgttga ctttggtgaa ggtgctgaat tttgtacaag agatgacacc    3600
cctatgatgg caagaccaga ttcaggtgaa gcctgcgacc aaaacagagc aggtacatca    3660
gaacaacaag gtgacttatc aagagaacc aagaaatga                            3699

<210> SEQ ID NO 77
<211> LENGTH: 2162
<212> TYPE: DNA
<213> ORGANISM: Saccharomyces cerevisiae

<400> SEQUENCE: 77
cgggatccat gtctagaata ataatgttga tccctactgg tacttccgtc ggtttgacct     60
ccgtatcctt gggtgtaata agagcaatgg aaagaaaggg tgttagatta tcagtctta    120 aaccaatcgc tcaacctaga gcaggtggtg acgccccaga ccaaactaca accattgtta    180
gagctaattc tacattacca gctgcagaac ctttgaagat gtctcatgtt gaatcattgt    240
tgtcttcaaa ccaaaaggat gttttgatgg aagaaatcat cgctaactac catgcaaaca    300
ctaaagacgc tgaagttgtc ttagtagaag gtttggttcc tacaagaaag caccaattcg    360
cacaatcttt gaactacgaa atagcaaaaa ccttgaacgc cgaaatagta ttcgttatgt    420
cacaaggtac agatacccca gaacaattga acgaaagaat cgaattgact agatccagtt    480
tcggtggtgc aaagaatact aacataacag gtgttattat taataagttg aacgctccag    540
ttgatgaaca aggtagaact agacctgact tgtctgaaat attcgatgac tcttcaaagg    600
ctcaagttat taagatcgat ccagcaaagt tacaagaatc cagtccatta cctgtcttgg    660
gtgctgtacc ttggtctttc gatttgattg ccacaagagc tatagacatg gctagacatt    720
tgaatgcaac cataatcaac gaaggtgaca taagacaag acacgtcaaa tccgtaacct    780
tttgtgctag aagtatccca catatgttgg aacacttcag agccggttct tgttagtta    840 catcagctga tagacctgac gtcttagtag ccgcttgttt ggcagccatg aatggtgttg    900
aaattggtgc attgttattg actggtggtt atgaaatgga tgccagaata tctaagttat    960
gcgaaagagc atttgccacc ggtttgccag ttttcatggt caatactaac acatggcaaa   1020 cttcttttgtc attgcaatct tttaatttgg aagttcctgt cgatgaccat gaaagaatcg   1080
```

```
aaaaggttca agaatacgtc gccaattacg taaacgctga atggattgaa tccttaaccg    1140
caacttctga aagatcaaga agattgagtc cacctgcttt cagataccaa ttgacagaat    1200
tggcaagaaa ggccggtaaa agagtagttt taccagaagg tgacgaacct agaacagtta    1260
aagctgcagc catctgtgca gaaagaggta ttgccacctg cgttttgttg ggtaacccag    1320
atgaaattaa cagagttgct gcatcacaag gtgtcgaatt gggtgcaggt atcgaaattg    1380
ttgatcctga agtcgtaaga gaatcttacg ttgctagatt agtcgaattg agaaaatcaa    1440
agggtatgac tgaaccagtt gcaagagaac aattggaaga taacgttgtc ttgggtacat    1500
taatgttgga acaagatgaa gtagacggtt tagtttctgg tgctgtccac actacagcaa    1560
acaccataag accaccttta caattgatca aaactgctcc aggttcttca ttggtatcca    1620
gtgttttctt tatgttgttg cctgaacaag tatacgttta cggtgactgc gcaattaatc    1680
cagaccctac agccgaacaa ttggctgaaa tagcaatcca atccgctgat agtgctatcg    1740
catttggtat tgaaccaaga gttgcaatgt tatcctatag tacaggtacc tccggtgctg    1800
gtagtgatgt cgaaaaagtt agagaagcca ctagattggc tcaagaaaag agaccagatt    1860
tgatgattga cggtccttg caatacgatg ccgctgtaat ggccgacgtt gctaaatcca    1920
aggctccaaa tagtcctgta gcaggtagag ccactgtttt tatttttccca gatttgaaca    1980 ctggtaacac cacttataag gccgttcaaa gatctgctga cttaatttca ataggtccaa    2040
tgttgcaggg tatgagaaaa cctgttaacg atttgtccag aggtgctttg gtcgatgaca    2100
tagtatacac catcgctttg actgcaattc aagcctctca acaacaacaa taagctagct    2160
ag                                                                  2162

<210> SEQ ID NO 78
<211> LENGTH: 2162
<212> TYPE: DNA
<213> ORGANISM: Saccharomyces cerevisiae

<400> SEQUENCE: 78
cgggatccat gtctagaata ataatgttga tccctactgg tacttccgtc ggtttgacct      60
ccgtatcctt gggtgtaata agagcaatgg aaagaaaggg tgttagatta tcagtctttt     120
aaccaatcgc tcaacctaga gcaggtggtg acgccccaga ccaaactaca accattgtta     180
gagctaattc tacattacca gctgcagaac ctttgaagat gtctcatgtt gaatcattgt     240
tgtcttcaaa ccaaaaggat gttttgatgg aagaaatcat cgctaactac catgcaaaca     300
ctaaagacgc tgaagttgtc ttagtagaag gtttggttcc tacaagaaag caccaattcg     360
cacaatcttt gaactacgaa atagcaaaaa ccttgaacgc cgaaatagta ttcgttatgt     420
cacaaggtac agatacccca gaacaattga acgaaagaat cgaattgact agatccagtt     480
tcggtggtgc aaagaatact aacataacag gtgttattat taataagttg aacgctccag     540
ttgatgaaca aggtagaact agacctgact tgtctgaaat attcgatgac tcttcaaagg     600
ctcaagttat taagatcgat ccagcaaagt tacaagaatc cagtccatta cctgtcttgg     660
gtgctgtacc ttggtctttc gatttgattg ccacaagagc tatagacatg gctagacatt     720
tgaatgcaac cataatcaac gaaggtgaca taaagacaag acacgtcaaa tccgtaacct     780
tttgtgctag aagtatccca catatgttgg aacacttcag agccggatct ttgttagtta     840
catcagctga tagacctgac gtcttagtag ccgcttgttt ggcagccatg aatggtgttg     900
aaattggtgc attgttattg actggtggtt atgaaatgga tgccagaata tctaagttat     960
```

```
gcgaaagagc atttgccacc ggtttgccag ttttcatggt caatactaac acatggcaaa    1020
cttctttgtc attgcaatct tttaatttgg aagttcctgt cgatgaccat gaaagaatcg    1080
aaaaggttca agaatacgtc gccaattacg taaacgctga atggattgaa tccttaaccg    1140
caacttctga aagatcaaga agattgagtc cacctgcttt cagataccaa ttgacagaat    1200
tggcaagaaa ggccggtaaa agagtagttt taccagaagg tgacgaacct agaacagtta    1260
aagctgcagc catctgtgca gaaagaggta ttgccacctg cgttttgttg ggtaacccag    1320
atgaaattaa cagagttgct gcatcacaag gtgtcgaatt gggtgcaggt atcgaaattg    1380
ttgatcctga agtcgtaaga gaatcttacg ttgctagatt agtcgaattg agaaaatcaa    1440
agggtatgac tgaaccagtt gcaagagaac aattggaaga taacgttgtc ttgggtacat    1500
taatgttgga acaagatgaa gtagacggtt tagtttctgg tgctgtccac actacagcaa    1560
acaccataag accacctta caattgatca aaactgctcc aggttcttca ttggtatcca    1620
gtgttttctt tatgttgttg cctgaacaag tatacgttta cggtgactgc gcaattaatc    1680
cagaccctac agccgaacaa ttggctgaaa tagcaatcca atccgctgat agtgctatcg    1740
catttggtat tgaaccaaga gttgcaatgt tatcctatag tacaggtacc tccggtgctg    1800
gtagtgatgt cgaaaaagtt agagaagcca ctagattggc tcaagaaaag agaccagatt    1860
tgatgattga cggtcctttg caatacgatg ccgctgtaat ggccgacgtt gctaaatcca    1920
aggctccaaa tagtcctgta gcaggtagag ccactgtttt tattttccca gatttgaaca    1980
ctggtaacac cacttataag gccgttcaaa gatctgctga cttaatttca ataggtccaa    2040
tgttgcaggg tatgagaaaa cctgttaacg atttgtccag aggtgctttg gtcgatgaca    2100
tagtatacac catcgctttg actgcaattc aagcctctca acaacaacaa taagctagct    2160
ag                                                                  2162

<210> SEQ ID NO 79
<211> LENGTH: 1805
<212> TYPE: DNA
<213> ORGANISM: Saccharomyces cerevisiae

<400> SEQUENCE: 79
ataagaatgc ggccgcatgt ccgacaacaa gatcaacatt ggtttggcag ttatgaaaat      60
attggaatcc tggggtgctg acactatcta cggtatccct tcaggtactt tgtcttcatt     120
aatggatgct atgggtgaag aagaaaacaa cgtaaagttc ttgcaagtta agcatgaaga     180
agtcggtgca atggctgcag ttatgcaatc caaattcggt ggtaatttgg gtgtaacagt     240
tggttccggt ggtccaggtg ctagtcactt gattaacggt ttatacgatg ccgctatgga     300
caatattcca gttgtcgcta tattgggttc aagacctcaa agagaattga acatggatgc     360
attccaagaa ttgaaccaaa acccaatgta cgatcatatt gccgtataca atagaagagt     420
tgcctatgct gaacaattgc ctaaattagt tgatgaagca gccagaatgg caatcgccaa     480
gagaggtgtc gccgtattag aagtccctgg tgacttcgct aaggtagaaa ttgataacga     540
ccaatggtac tccagtgcta attccttgag aaaatatgca ccaatagccc ctgctgcaca     600
agatatcgac gccgctgtag aattgttgaa caacagtaag agacctgtta tctacgcagg     660
tattggtact atgggtcacg gtccagccgt ccaagaatta gctagaaaaa tcaaggcacc     720
tgtaattact acaggtaaaa atttcgaaac attcgaatgg gattttgaag cattgacagg     780
ttcaacctat agagttggtt ggaaaccagc caacgaaact attttggaag cagatacagt     840
cttattcgcc ggttctaatt ttcctttctc agaagttgaa ggtactttta gaaacgtcga     900
```

```
taacttcatc caaatagata tagacccagc tatgttaggt aaaagacatc acgctgatgt    960
tgcaattttg ggtgacgccg gtttggctat cgatgaaatc ttgaataagg ttgatgctgt   1020
cgaagaatct gcatggtgga cagccaattt gaagaacatt gcaaactgga gagaatacat   1080
caacatgttg gaaaccaagg aagagggtga cttgcaattc taccaagttt acaacgctat   1140
aaataaccat gctgatgaag acgcaatcta ttctatagat gttggtaact ctacccaaac   1200
ttcaattaga catttgcaca tgaccccaaa gaatatgtgg agaacctcac ctttatttgc   1260
cactatgggt atcgctattc caggtggttt gggtgctaaa acacttatc ctgacagaca    1320 agtttggaat attataggtg acggtgcatt ctctatgaca tacccagacg tagttaccaa   1380
cgttagatat aatatgcctg ttatcaacgt cgtattttca aacacagaat acgctttcat   1440
taaaaataag tatgaagata ccaataagaa cttgtttggt gtcgacttca ctgatgtaga   1500
ctacgctaaa atagctgaag cacaaggtgc aaagggtttt accgtttcta gaatcgaaga   1560
tatggacaga gttatggccg aagctgtcgc agccaataag gctggtcata ctgttgtcat   1620
agactgtaag atcacacaag atagaccaat tcctgttgaa acattgaagt tggactccaa   1680
gttgtacagt gaagatgaaa ttaaagctta caaggaaaga tacgaagctg caaatttggt   1740 tcctttaga gaatacttgg aagcagaagg tttagaatct aaatatatta agtaattaat    1800
taagg                                                              1805

<210> SEQ ID NO 80
<211> LENGTH: 1802
<212> TYPE: DNA
<213> ORGANISM: Saccharomyces cerevisiae

<400> SEQUENCE: 80
ataagaatgc ggccgcatga cacaaggtaa aatcactgcc tccgccgcaa tgttgaatgt     60
attaaagacc tggggtgttg acacaatcta cggtattcca agtggtacat tgtcttcatt    120
aatggatgca ttggccgaag ataaggacat aagattttta caagtaagac atgaagaaac    180
cggtgccttg gctgcagtta tgcaggctaa gttcggtggt agtattggtg tagcagttgg    240
ttctggtggt ccaggtgcca ctcatttgat taatggtgta tatgatgccg ctatggacaa    300
tacaccattt ttggctatat tgggttcaag acctgttaac gaattgaaca tggatgcatt    360
ccaagaattg aaccaaaacc caatgtacaa cggtatagct gtatacaaca agagagttgc    420
ttatgcagaa caattgccta agtcatcga tgaagcttgt agagcagcca tttccaaaaa    480
gggtccagca gttgtcgaaa tacctgttaa ctttggtttc caagaaatcg atgaaaactc    540
atactacggt tccggtagtt acgaaagatc ctttatcgcc ccagctttga atgaagttga    600
aatcgacaag gcagtcgaaa ttttaaataa cgccgaaaga ccagttatat atgctggttt    660
cggtggtgtc aaagcaggtg aagtaattac agaattgtct agaaagatta agcccccaat    720
aatcactaca ggtaaaaatt tcgaagcttt cgaatggaac tacgaaggtt taaccggttc    780
agcttataga gttggttgga aacctgccaa tgaagtagtt tttgaagctg atactgtctt    840
gttcttaggt tccaactttg cattcgccga agtatacgaa gcttttaaga acacagaaaa    900
attcatacaa gttgatatcg acccatataa attgggtaaa agacatgcat ggatgccag    960 tatattaggt gacgctggtc aagctgcaaa ggcaatctta gataaagtta tccagtcga    1020 atctacacct tggtggagag ctaacgttaa aaataaccaa aactggagag actacatgaa   1080
taagttggaa ggtaaaactg agggtgaatt gcaattgtac caagtttaca acgctattaa   1140
```

```
caaacacgcc gatcaagacg ctatctattc tttggatgtc ggttcaacca ctcaaacatc    1200
caccagacat ttgcacatga cacctaaaaa tatgtggaga acttcacctt tgtttgcaac    1260
aatgggtata gccttaccag gtggtatcgc cgctaaaaag gatacccctg acagacaagt    1320
ttggaacatt atgggtgacg gtgcttttaa tatgtgctac ccagatgtaa tcactaacgt    1380
tcaatacgac ttgccagtta ttaatttggt attttctaac gctgaatacg ttttattaa     1440 aaataagtac gaagatacaa ataagcattt gttcggtgtt gatttcacca acgcagacta    1500
cggtaaaatt gctgaagcac aaggtgccgt tggttttact gtcgatagaa tcgaagatat    1560
tgacgcagtc gtagccgaag ctgttaagtt gaataagggt ggtaaaaccg ttgtcattga    1620
tgctagaata actcaacata gaccattgcc tgtcgaagta ttggaattag acccaaagtt    1680
acacagtgaa gaagctatta aagcttttaa agaaaagtac gaagcagaag aattggttcc    1740
ttttagattg ttcttagaag aagaaggttt acaatctaga gctattaaat aattaattaa    1800
gg                                                                   1802

<210> SEQ ID NO 81
<211> LENGTH: 1838
<212> TYPE: DNA
<213> ORGANISM: Saccharomyces cerevisiae

<400> SEQUENCE: 81
ataagaatgc ggccgcatgg taatgaaaca aacaaagcaa acaaacatct tagcaggtgc      60
cgccgttatc aaggtattgg aagcatgggg tgtagaccac ttatatggta ttccaggtgg     120
ttccatcaat agtattatgg atgccttgtc cgctgaaaga gacagaatac attacatcca     180
agtcagacac gaagaagtag gtgcaatggc tgcagccgct gatgccaagt tgactggtaa     240
aataggtgtt tgtttcggtt cagctggtcc aggtggtaca catttgatga atggtttata     300
tgatgcaaga gaagaccacg ttcctgtctt ggctttaatt ggtcaattcg gtactactgg     360
tatgaacatg gatactttcc aagaaatgaa cgaaaaccca atctatgcag atgttgccga     420
ctacaatgta acagctgtta acgcagccac cttgcctcat gtcatcgatg aagcaattag     480
aagagcctac gctcaccaag gtgtcgctgt tgtccaaatt ccagtagatt gccttggca      540 acaaatacca gcagaagact ggtatgcatc tgccaattca taccaaaccc ctttgttacc     600
agaacctgat gtccaagctg taactagatt gacccaaact ttgttagctg cagaaagacc     660
attaatctat tacggtatcg gtgctagaaa agctggtaaa gaattggaac aattgtccaa     720
gacattgaag atcccattga tgagtaccta tcctgttaag ggtattgtcg ccgatagata     780
tccagcttac ttgggttctg ctaatagagt tgcacaaaaa cctgccaacg aagctttggc     840
acaagccgat gtagttttgt tcgttggtaa caactaccca ttcgcagaag tttcaaaggc     900
cttcaagaac actagatact ttttgcaaat agatatcgac cctgcaaagt tgggtaaaag     960
acataagact gatatagctg tcttggctga cgcacaaaag acattggccg ctatattagc    1020
tcaagtatcc gaaagagaaa gtaccacatg gtggcaagcc aacttagcta atgttaagaa    1080
ctggagagca tatttggcct ccttagaaga taaacaagaa ggtccattgc aagcctacca    1140
agtattgaga gctgttaata agatcgctga acctgatgca atctatagta tagatgttgg    1200
tgacatcaat ttgaacgcta acagacattt gaagttgaca ccatctaaca gacacatcac    1260
ttcaaactta ttcgcaacaa tgggtgttgg tattccaggt gctatagcag ccaagttgaa    1320
ctaccctgaa agacaagttt ttaacttagc tggtgacggt ggtgcatcta tgaccatgca    1380
agacttggct actcaagtac aataccattt gcctgttata aatgtcgtat tcacaaactg    1440
```

```
ccaatacggt tttatcaagg atgaacaaga agacaccaac caaaacgatt tcataggtgt    1500
tgaattcaat gatatcgact tctctaagat cgctgacggt gttcatatgc aagcattcag    1560
agtcaacaag atcgaacaat tgccagatgt ttttgaacaa gccaaagcta ttgcacaaca    1620
cgaacctgtt ttgatcgatg ctgtcattac cggtgacaga ccattacctg cagaaaaatt    1680
gagattagat tctgccatgt cttcagctgc agacattgaa gcctttaagc aaagatatga    1740
agctcaagat ttgcaaccat tgtcaacata cttaaagcaa ttcggtttgg atgacttaca    1800
acatcaaatt ggtcaaggtg ttttttaatt aattaagg                            1838
```

<210> SEQ ID NO 82
<211> LENGTH: 3306
<212> TYPE: DNA
<213> ORGANISM: Saccharomyces cerevisiae

<400> SEQUENCE: 82

```
atgtccgcaa aagccatttc cgaacaaact ggtaaagaat tattatacaa gttcatctgc      60
acaacctcag ccatacaaaa cagattcaag tatgcaagag ttactccaga tacagactgg     120
gccagattgt tacaagatca tccttggttg ttatcacaaa acttggttgt caagcctgac     180
caattgatta aaagacgtgg taaattgggt ttagtaggtg ttaatttgac attagatggt     240
gttaagtcct ggttgaagcc aagattaggt caagaagcaa ccgtcggtaa agccactggt     300
ttcttgaaaa atttcttgat cgaaccattc gtacctcatt ctcaagctga gaattttac     360 gtttgtatat acgcaactag agaaggtgac tatgtcttgt ttcatcacga aggtggtgtt     420
gatgtaggtg acgtagacgc caaagctcaa aagttgttag ttggtgtcga tgaaaaattg     480
aacccagaag acattaaaaa gcatttgttg gttcacgccc ctgaagataa aaaggaaata     540
ttggcttctt ttatctcagg tttgtttaat ttctacgaag atttgtactt cacttacttg     600
gaaattaacc cattggtagt tacaaaggat ggtgtatacg ttttggactt agctgcaaag     660
gtcgatgcaa cagccgacta catttgtaaa gtaaagtggg gtgacataga atttccacct     720
ccattcggta gagaagcata tccagaagaa gcctacattg ctgatttgga cgccaaatcc     780
ggtgctagtt tgaagttaac cttgttgaac cctaaaggta gaatctggac tatggttgca     840
ggtggtggtg cctcagtcgt atattccgat actatttgcg acttgggtgg tgttaacgaa     900
ttagctaact acggtgaata cagtggtgca ccatctgaac aacaaaccta tgattacgct     960
aagactatct tgagtttaat gacaagagaa aagcatcctg atggtaaaat tttgatcatc    1020
ggtggttcta tcgctaactt cacaaacgtc gccgctacct tcaaaggtat agtaagagca    1080
atcagagatt accaaggtcc attgaaggaa cacgaagtaa ccatttttgt tagaagaggt    1140
ggtcctaact accaagaagg tttaagagtc atgggtgaag taggtaaaac tacaggtatc    1200
ccaattcatg tatttggtac tgaaactcac atgactgcta ttgttggtat ggcattaggt    1260
catagaccaa tacctaatca acctccaact gctgctcaca cagctaatttt cttgttaaac    1320 gcatctggtt caacatccac cccagcccca tcaagaacag ctagtttctc tgaatcaaga    1380
gctgatgaag ttgctccagc taagaaagca aaaccagcca tgcctcaaga ctctgttcca    1440
tcacctagat ccttgcaagg taaaagtacc actttgtttt caagacatac aaaggcaatt    1500
gtttggggta tgcaaaccag agccgtccaa ggcatgttgg atttcgacta tgtttgttca    1560
agagatgaac catccgttgc tgcaatggtc tatccttttta ctggtgacca taacaaaag    1620 ttctactggg gtcacaagga aatattaatc ccagtttttta aaaacatggc cgatgctatg    1680
```

```
agaaagcatc ctgaagttga tgtattgatt aacttcgcaa gtttaagatc agcctatgat   1740
tcaactatgg aaactatgaa ctacgctcaa atcagaacta ttgctatcat tgcagaaggt   1800
atcccagaag cattgacaag aaaattaatt aaaaaggcag atcaaaaggg tgtaaccata   1860
atcggtccag caactgttgg tggtatcaaa cctggttgtt ttaagattgg taatacaggt   1920
ggcatgttgg ataacatatt ggcttcaaaa ttgtatagac caggttccgt cgcatacgta   1980
tccagaagtg gtggtatgag taacgaatta acaacataa tttcaagaac aaccgatggt   2040
gtatatgaag gtgttgctat tggtggtgac agatacccag gttctacttt tatggatcat   2100
gttttgagat atcaagacac ccctggtgtc aaaatgatcg ttgtcttagg tgaaataggt   2160
ggtacagaag aatacaaaat ttgtagaggt attaaggaag gtagattgac caaaccaatt   2220
gtttgttggt gcataggtac atgtgctacc atgttttctt cagaagttca attcggtcac   2280
gcaggtgcct gcgctaatca agcatctgaa acagcagttg ccaaaaacca agcattgaag   2340
gaagcaggtg ttttttgtccc tagatcattc gatgaattgg gtgaaatcat tcaatccgtc   2400
tatgaagact tagtagccaa tggtgtaatt gttccagctc aagaagttcc tccacctact   2460
gtccctatgg attactcttg ggctagagaa ttgggtttaa tcagaaaacc agcttctttt   2520
atgacttcca tttgtgatga agaggtcaa gaattgatct atgctggtat gcctatcaca   2580
gaagttttca aggaagaaat gggtataggt ggtgtcttgg gtttgttgtg gttccaaaag   2640
agattgccaa agtactcatg tcaattcatt gaaatgtgct aatggtcac cgctgatcat   2700 ggtcctgccg tatccggtgc tcacaacact ataatctgcg ctagagcagg taaagatttg   2760
gtttcttctt tgacttcagg tttgttaaca attggtgaca gatttggtgg tgctttggac   2820
gccgctgcaa agatgtttag taaggcattc gattctggta taatcccaat ggaatttgtt   2880
aataagatga aaaaggaggg taaattaatc atgggtatcg gtcatcgtgt taagtctata   2940
aataaccctg atatgagagt acaaatcttg aaggactatg ttagacaaca cttccagca   3000 acacctttgt tagattacgc cttagaagtt gaaaagatta ctacatctaa gaaaccaaat   3060
ttgatcttga acgttgatgg tttgatcggt gttgcttttg ttgatatgtt aagaaactgt   3120
ggtagtttca ctagagaaga agccgatgaa tatattgaca tcggtgcttt gaacggtatc   3180
ttcgttttgg gtagatcaat gggttttatt ggtcattact tggatcaaaa gagattaaag   3240
caaggtttgt atagacaccc ttgggatgat atttcctacg ttttgcctga acacatgagt   3300
atgtaa                                                              3306
```

<210> SEQ ID NO 83
<211> LENGTH: 3306
<212> TYPE: DNA
<213> ORGANISM: Saccharomyces cerevisiae

<400> SEQUENCE: 83

```
atgtccgcta aagctatttc cgaacaaact ggtaaagaat tattatacaa gtacatttgc     60
accacctcag ccatacaaaa cagattcaag tatgcaagag ttacaccaga taccgactgg    120
gcccatttgt tacaagatca cccttggttg ttatctcaat cattggttgt caaacctgac    180
caattgatta aaagacgtgg taaattgggt ttagtcggtg taaacttgag tttagatggt    240
gttaagtctt ggttgaagcc aagattaggt catgaagcta cagttggtaa agcaaagggt    300
ttcttgaaaa atttcttgat cgaaccattc gtacctcact cacaagctga gaattttac    360 gtttgtatct atgcaactag agaaggtgac tatgtcttgt ttcatcacga aggtggtgtt    420
gacgtcggtg acgttgacgc caaagctcaa aagttgttag taggtgttga tgaaaagtta    480
```

```
aacacagaag acatcaagag acatttgttg gtacacgccc cagaagataa aaaggaagtt    540
ttggcttcct ttataagtgg tttgtttaat ttctacgaag atttgtactt cacctacttg    600
gaaattaacc ctttagtagt tactaaggat ggtgtctata tattggactt agctgcaaaa    660
gtagatgcaa ctgccgacta catctgtaag gttaagtggg gtgacattga atttccacct    720
ccattcggta gagaagcata tccagaagaa gcctacattg ctgatttgga cgcaaaatct    780
ggtgcctcat tgaagttaac attgttgaac cctaagggga gaatatggac tatggttgct    840
ggtggtggtg caagtgtcgt atattctgat acaatctgcg acttgggtgg tgttaacgaa    900
ttagctaact acggtgaata ctcaggtgca ccatccgaac aacaaactta tgattacgct    960
aagaccatct tgagtttaat gactagagaa aagcatcctg aaggtaaaat tttgatcatc   1020
ggtggttcta tagcaaactt cactaacgtt gccgctacat tcaagggtat agtcagagct   1080
atcagagatt atcaaggtcc attgaaggaa cacgaagtta caatattcgt cagaagaggt   1140
ggtcctaact accaagaagg tttaagagta atgggtgaag ttggtaaaac tacaggtatc   1200
ccaattcatg tatttggtac tgaaacacac atgactgcca tcgttggtat ggctttaggt   1260
catagaccaa ttcctaatca acctccaaca gcagcccaca ccgccaattt cttgttaaac   1320
gcttccggta gtacctctac tccagcacca tcaagaactg cctcattctc cgaaagtaga   1380
gctgatgaag ttgctccagc taagaaagca aaaccagcca tgcctcaaga ctccgttcca   1440
agtcctagat cattgcaagg taaatcagca acattatttt ccagacatac caaagccatt   1500
gtatggggta tgcaaacaag agctgttcaa ggcatgttgg atttcgacta tgtttgtagt   1560
agagatgaac catctgtcgc tgcaatggta tatccttttta ccggtgacca taaacaaaag   1620
ttctactggg gtcacaagga aatattaatc ccagttttta aaaacatggc cgatgctatg   1680
aaaaagcatc ctgaagttga tgtattgatt aacttcgctt cattaagatc cgcttatgat   1740
tctactatgg aaacaatgaa ctacgcacaa attagaacca tagctatcat tgcagaaggt   1800
ataccagaag cattgactag aaagttaatc aaaaaggccg atcaaaaagg tgtcactata   1860
atcggtccag ctacagtagg tggtataaaa cctggttgtt ttaagatcgg taatactggt   1920
ggcatgttgg ataacatatt ggcatcaaaa ttgtatagac caggttccgt agcttacgtt   1980
tcaagaagcg gtggtatgag taacgaattg aacaacataa tttcaagaac cactgatggt   2040
gtttatgaag gtgtcgctat tggtggtgac agatacccag ttctacttt tatggatcat   2100 gttttgagat atcaagacac acctggtgtc aaaatgatcg ttgtcttagg tgaaataggt   2160
ggtactgaag aatacaaaat ttgcagaggt ataaggaag gtagattgac aaaaccagta   2220
gtttgttggt gcattggtac ttgtgcaact atgttttctt cagaagttca attcggtcat   2280
gcaggtgcct gcgctaatca agcatctgaa acagcagttg ccaaaaacca agccttaaag   2340
gaagctggtg tttttgtccc tagatcattc gatgaattgg gtgaaatcat tcaatccgta   2400
tatgaagact tagttgccaa gggtgctatt gtcccagctc aagaagtacc tccacctact   2460
gttcctatgg attactcatg ggcaagagaa ttgggtttga tcagaaagcc agctagtttt   2520
atgacctcta tctgtgatga aagaggtcaa gaattgatct atgctggtat gcctatcact   2580
gaagtcttca aggaagaaat gggtatcggt ggtgtattgg gtttgttgtg gttccaaaga   2640
agattaccaa agtactcatg tcaattcata gaaatgtgct taatggttac agctgatcat   2700
ggtccagctg tttctggtgc ccacaacacc ataatctgcg ctagagcagg taaagatttg   2760
gtttcttctt tgacctctgg tttgttaact attggtgaca gatttggtgg tgcattggac   2820
```

-continued

```
gccgctgcaa aaatgttttc aaaggctttc gattccggta taatcccaat ggaatttgtt    2880
aataagatga aaaaggaggg taaattaatc atgggtatcg gtcatcgtgt taagtcaatt    2940
aataaccctg atatgagagt ccaaatattg aaggacttcg taaagcaaca cttcccagca    3000
acacctttgt tagattacgc cttagaagtt gaaaagatta caacctctaa aaagccaaat    3060
ttgatcttga acgttgatgg ttttataggt gtcgctttcg tagacatgtt aagaaactgt    3120
ggttctttta ctagagaaga agccgatgaa tatgttgaca ttggtgcttt gaatggtata    3180
tttgtcttag gtagatcaat gggtttatt ggtcattact tggatcaaaa gagattaaag    3240
caaggtttgt atagacaccc ttgggacgat atttcctacg ttttgcctga acacatgagt    3300
atgtaa                                                               3306
```

ENGINEERING OF ACETYL-COA METABOLISM IN YEAST

STATEMENT OF PRIORITY

This application is a 35 U.S.C. § 371 national phase application of International Application Serial No. PCT/SE2014/051228, filed Oct. 17, 2014, which claims the benefit, under 35 U.S.C. § 119 (a) of U.S. Application Ser. No. 61/893,124, filed Oct. 18, 2013, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 9737-42_ST25.txt, 65,936 bytes in size, generated Apr. 14, 2016 and filed via EFS-Web, is provided in lieu of a paper copy. This Sequence Listing is hereby incorporated herein by reference into the specification for its disclosures.

FIELD OF THE INVENTION

The present invention relates to the development of metabolic engineering of microorganisms. More specifically this invention relates to a non-ethanol producing yeast strain, for instance of the yeast *Saccharomyces cerevisiae*, that can produce cytosolic acetyl-Coenzyme A (CoA), such as by converting glucose to acetyl-CoA in the cytosol.

BACKGROUND OF THE INVENTION

With the requirements for development of sustainable solutions for provision of fuels, chemicals and materials, there is much focus on biotechnology, as this may serve as one of the pillars underlying a modern, sustainable society. Biotechnology has been used for generations in the production of fermented beverages and food products, and in the last 60 years for the production of antibiotics, food ingredients and feed additives. In recent years, several new processes for production of chemicals that can be used for polymer production have been introduced, and the production of bioethanol for fuel use has increased rapidly. Currently, there is extensive research on the development of novel cell factories for the production of chemicals and novel fuels, and it is expected that this will lead to implementation of several new biotech processes in the coming years.

The core of this development is the design and construction of cell factories that can ensure efficient conversion of the raw material to the product of interest. Traditionally, microorganisms that naturally produce a desired molecule were identified and then improved through classical strain engineering based on mutagenesis and screening. This has been a very effective approach and has resulted in low-cost production processes for many different chemicals, e.g. penicillin, citric acid and lysine. With the introduction of genetic engineering and methods for detailed analysis of cellular metabolism it became possible to use a more directed approach to improve cell factories, generally referred to as metabolic engineering. Today metabolic engineering has evolved into a research field that encompasses detailed metabolic analysis with the objective to identify targets for metabolic engineering and the implementation of metabolic engineering strategies for improvement and/or design of novel cell factories. In recent years, synthetic biology has emerged as another research field that originally aimed at reconstruction of small, artificial biological systems, e.g. assembling a new biological regulon or oscillators that can be used to regulate gene expression in response to a specific input. But synthetic biology also includes the synthesis of DNA and complete chromosomes as illustrated in a recent work on reconstruction of a complete bacterial chromosome.

SUMMARY OF THE INVENTION

A primary object of the present invention is to generate a yeast platform cell factory with increased cytosolic acetyl-CoA (AcCoA) supply, by introduction of steps for the direct conversion of pyruvate to AcCoA. The yeast platform cell factory of the present invention can efficiently convert pyruvate to acetyl-CoA and this feature is combined with elimination of pyruvate decarboxylase activity, resulting in an efficient cytosolic acetyl-CoA producer that cannot produce ethanol. This will result in high cytosolic levels of the important precursor acetyl-CoA.

Acetyl-CoA metabolism is highly compartmentalized in eukaryotic cells as this metabolite is used for metabolism in the cytosol, mitochondria, peroxisomes and the nucleus. Acetyl-CoA serves as a key precursor metabolite for the production of important cellular constituents such as fatty acids, sterols, and amino acids as well as it is used for acetylation of proteins. Besides these important functions it is also precursor metabolite for many other biomolecules, such as polyketides, isoprenoids, 3-hydroxypropionic acid, 1-butanol and polyhydroxyalkanoids, which encompass many industrially relevant chemicals. The yeast *Saccharomyces cerevisiae* is a very important cell factory as it is already widely used for production of biofuels, chemicals and pharmaceuticals, and there is therefore much interest in developing platform strains of this yeast that can be used for production of a whole range of different products. It is however a problem that such a platform cell factory for efficient production of cytosolic acetyl-CoA is not as efficient as needed for good industrial application. Our invention is a multiple gene modification approach of the yeast generating higher yield of acetyl-CoA, by combining pathways for direct conversion from pyruvate to acetyl-CoA together with elimination of ethanol production.

An aspect of the embodiments relates to a yeast lacking any endogenous gene encoding pyruvate decarboxylase or comprising disrupted gene or genes encoding pyruvate decarboxylase. The yeast also comprises at least one heterologous pathway for synthesis of cytosolic acetyl-Coenzyme A (CoA). The at least one heterologous pathway comprises at least one heterologous gene encoding a respective enzyme involved in synthesis of acetyl-CoA, with the proviso that the at least one heterologous gene is not a heterologous gene encoding a pyruvate formate lyase.

Another aspect of the embodiments relates to a method of producing acetyl-CoA comprising culturing a yeast according to above in culture conditions suitable for production of cytosolic acetyl-CoA from the yeast.

A further aspect of the embodiments relates to use of a yeast according to above for the production of cytosolic acetyl-CoA.

Yet another aspect of the embodiments relates to a method of producing a yeast suitable for the production of cytosolic acetyl-CoA. The method comprises deleting or disrupting any endogenous gene encoding pyruvate decarboxylase in the yeast. The method also comprises introducing, into the yeast, at least one heterologous pathway for synthesis of cytosolic acetyl-CoA. The at least one heterologous pathway comprises at least one heterologous gene encoding a respective enzyme involved in synthesis of acetyl-CoA, with the proviso that the at least one heterologous gene is not a heterologous gene encoding a pyruvate formate lyase.

DETAILED DESCRIPTION OF THE INVENTION

Figure 1:
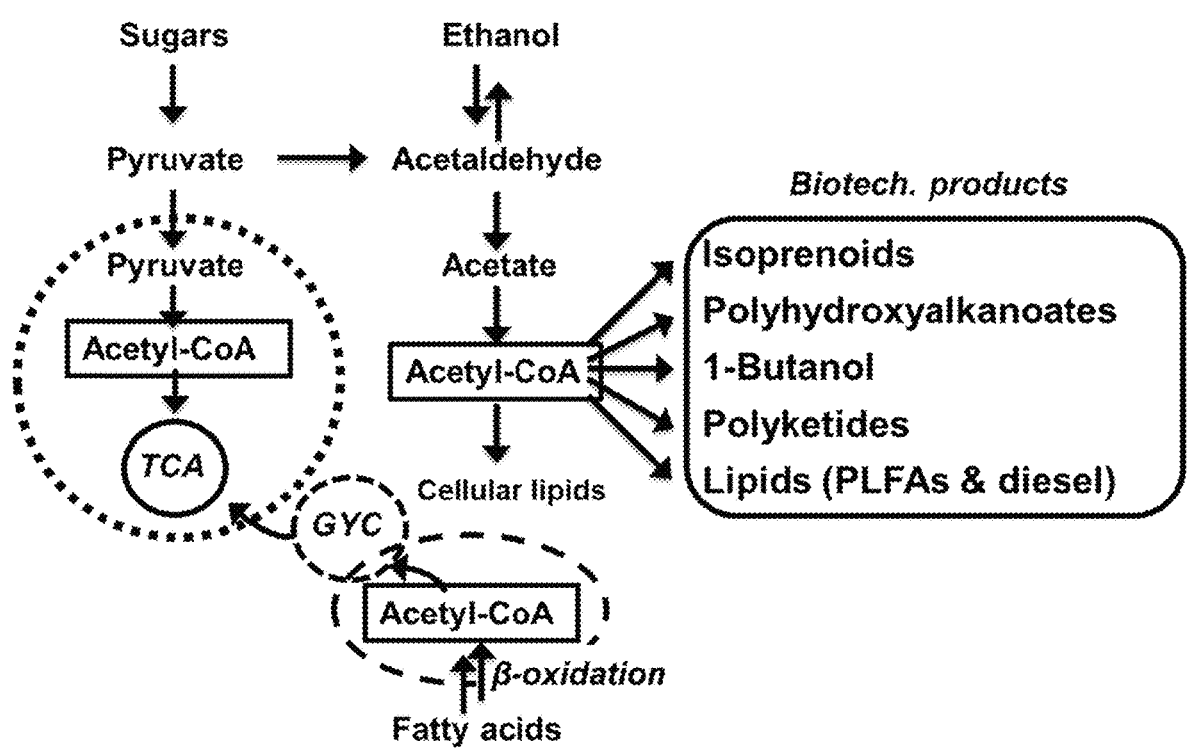
FIG. 1 provides a simplified overview of acetyl-CoA metabolism in *S. cerevisiae*. Acetyl-CoA is key metabolite in three different compartments: the cytosol (marked as ~ ~ ~), the mitochondria (marked as • • •), and the peroxisomes (marked as - - -). There is no direct transport of the acetyl-CoA between the three compartments, and the biosynthesis of acetyl-CoA in the three compartments involves different metabolic pathways. In the mitochondria, acetyl-CoA is formed from pyruvate by the pyruvate dehydrogenase complex. In the cytosol, acetyl-CoA is formed from acetate by acetyl-CoA synthase. In the peroxisomes, acetyl-CoA can be formed from both acetate (also by acetyl-CoA synthase, not shown) and from fatty acids by beta-oxidation. In the mitochondria, the primary fate of acetyl-CoA is oxidation via the tricarboxylic acid (TCA) cycle. Acetyl-CoA in the peroxisomes can via the glyoxylate cycle (GYC) be converted to $C_4$ organic acids (malic and succinic acid) that can be transferred to the mitochondria for oxidation via malic enzyme and the TCA cycle. The primary fate of acetyl-CoA in the cytosol is to serve as precursor for cellular lipids (fatty acids and ergosterol). Many industrially interesting biotechnological products are derived from acetyl-CoA and the biosynthesis of most of these occurs in the cytosol. A platform yeast cell factory for all these products should therefore redirect carbon towards the acetyl-CoA in the cytosol.
Figure 2:
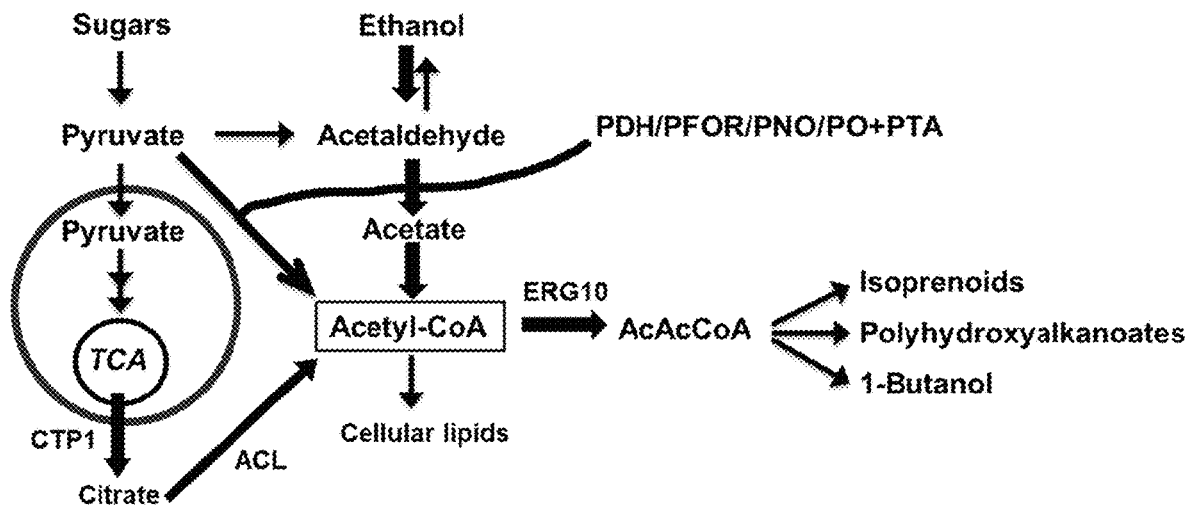
FIG. 2 provides an overview of the strategy that can be used in the invention. The normal route for conversion of pyruvate to acetaldehyde and further into acetyl-CoA in the cytosol is blocked through deletion of the three structural genes encoding pyruvate decarboxylase activity in yeast (PDC1, PDC5 and PDC6). This strain is auxotrophic for $C_2$ carbon sources such as acetate or ethanol, and it has been shown that this requirement is solely to fulfill the need for acetyl-CoA in the cytosol (required for production of cellular lipids). By removing pyruvate decarboxylase activity the yeast cells also cannot produce ethanol from sugars, such as glucose. To re-install a cytosolic route for production of acetyl-CoA several different strategies can be used: 1) expression of cytosolic pyruvate dehydrogenase (PDH); 2) expression of pyruvate ferrodoxin oxidoreductase (PFOR); 3) expression of pyruvate oxidase (PO) and phosphate acetyltransferase (PTA); and 4) expression of ATP-citrate lyase (ACL). The strains with the novel pathways for production of cytosolic acetyl-CoA can e.g. be used for production of fatty acids, 3-hydroxypropionic acid, isoprenoids, polyhydroxyalkanoates and 1-butanol.

The invention herein relies, unless otherwise indicated, on the use of conventional techniques of biochemistry, molecular biology, microbiology, cell biology, genomics and recombinant technology.

To facilitate understanding of the invention, a number of terms are defined below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein the term "recombinant" when used means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

As used herein, the term "overproducing" is used in reference to the production of acetyl-CoA in a host cell and indicates that the host cell is producing more acetyl-CoA by virtue of the introduction of recombinant/heterologous nucleic acid sequences encoding polypeptides that alter the host cell's normal metabolic pathways or as a result of other modifications (e.g., altering the expression of one or more endogenous polynucleotides) as compared with, for example, the host cell that is not modified/transformed with the recombinant polynucleotides as described herein.

As used herein, the terms "protein" and "polypeptide" refer to compounds comprising amino acids joined via peptide bonds and are used interchangeably.

The terms "increase," "increasing," "increased," "enhance," "enhanced," "enhancing," and "enhancement" (and grammatical variations thereof), as used herein, describe an elevation in, for example, the production of acetyl-CoA in a microorganism (e.g., a yeast). This increase can be observed by comparing said increase in a microorganism transformed with, for example, recombinant polynucleotides encoding a cytosolic pyruvate dehydrogenase (PDH) complex and one or more recombinant polynucleotide sequences encoding polypeptides responsible for synthesis and attachment of the lipoyl group to the microorganism not transformed with recombinant polynucleotides. Thus, as used herein, the terms "increase," "increasing," "increased," "enhance," "enhanced," "enhancing," and "enhancement" (and grammatical variations thereof), and similar terms indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

As used herein, the terms "reduce," "reduced," "reducing," "reduction," "diminish," "suppress," and "decrease" (and grammatical variations thereof), describe, for example, a decrease in the pyruvate decarboxylase activity in a microorganism (e.g., a yeast having deletions in the polynucleotides PDC1, PDC5 and PDC6) as compared to a control (e.g., a yeast not having said deletions in the polynucleotides PDC1, PDC5 and PDC6). Thus, as used herein, the terms "reduce," "reduces," "reduced," "reduction," "diminish," "suppress," and "decrease" and similar terms mean a decrease of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

The term "overexpress," "overexpresses" or "overexpression" as used herein refers to higher levels of activity of a gene (e.g. transcription of the gene); higher levels of translation of mRNA into protein; and/or higher levels of production of a gene product (e.g., polypeptide) than would be in the cell in its native (or control (e.g., not transformed with the particular heterologous or recombinant polypeptides being overexpressed)) state. These terms can also refer to an increase in the number of copies of a gene and/or an increase in the amount of mRNA and/or gene product in the cell. Overexpression can result in levels that are 25%, 50%, 100%, 200%, 500%, 1000%, 2000% or higher in the cell, as compared to control levels.

A "heterologous" or a "recombinant" nucleotide sequence is a nucleotide sequence not naturally associated with a host cell into which it is introduced, including non-naturally occurring multiple copies of a naturally occurring nucleotide sequence. A heterologous gene may optionally be codon optimized for expression in yeast according to techniques well known in the art and as further described herein. A heterologous gene also encompasses, in some embodiments, an endogenous gene controlled by a heterologous promoter and/or control elements to achieve an expression of the gene that is different from, typically higher, i.e. so-called overexpression, than normal or baseline expression of the gene in a yeast comprising the endogenous gene under control of wild type (endogenous) promoter and control elements.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "disrupted gene" as defined herein involves any mutation or modification to a gene resulting in a partial or fully non-functional gene and gene product. Such a mutation or modification includes, but is not limited to, a missense mutation, a nonsense mutation, a deletion, a substitution, an insertion, and the like. Furthermore, a disruption of a gene can be achieved also, or alternatively, by mutation or modification of control elements controlling the transcription of the gene, such as mutation or modification in a promoter and/or enhancement elements. In such a case, such a mutation or modification results in partially or fully loss of transcription of the gene, i.e. a lower or reduced transcription as compared to native and non-modified control elements. As a result a reduced, if any, amount of the gene product will be available following transcription and translation.

The objective of gene disruption is to reduce the available amount of the gene product, including fully preventing any production of the gene product, or to express a gene product that lacks or having lower enzymatic activity as compared to the native or wild type gene product.

"Introducing" in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term "transformation" as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear genome. Stable transformation as used herein can also refer to a nucleic acid molecule that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a yeast). Stable transformation of a cell can be detected by, for example, a Northern blot hybridization assay of RNA of the cell with nucleic acid sequences which specifically hybridize with a nucleotide sequence of a nucleic acid molecule introduced into a yeast or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

In some embodiments, *Saccharomyces cerevisiae* can be a host for carrying out the invention, as it is a popular host in basic and applied research apart from being a good ethanol producer, a precursor of esters and specifically of fatty acid ethyl esters. In addition, other yeast cells useful with the present invention include, but are not limited to, other *Saccharomyces* species, *Hansenula polymorpha*, *Kluyveromyces* species, *Pichia* species, *Candida* species, *Trichoderma* species, *Yarrowia lipolytica*, etc.

In industry, there is much interest in applying a limited number of platform cell factories for production of a wide range of fuels and chemicals as this allows for flexible use of production facilities, which are very capital intensive. One of these platform cell factories is the yeast *Saccharomyces cerevisiae*, which is widely used for the production of beer, bread, wine, bioethanol, nutraceuticals, chemicals and pharmaceuticals. These platform cell factories can efficiently convert raw materials, today typically glucose/fructose derived from starch or sucrose, but in the future also pentoses derived from lignocellulose, into so-called precursor metabolites can then be further converted into a product of interest. One of these precursor metabolites is acetyl-CoA, that is used as precursor for the production of a wide range of industrially very interesting products (see FIG. 1). Several of these products are produced by pathways that drain acetyl-CoA from the cytosol and in connection with reconstruction of synthetic pathways it is generally desirable to position these pathways in this compartment as this will minimize issues related to product secretion. As illustrated in FIG. 1, acetyl-CoA is, however, produced and used in several different cellular compartments, i.e. the cytosol, mitochondria and the peroxisomes, and in *S. cerevisiae* it cannot be transported directly between the different compartments (*S. cerevisiae* holds all the components of the carnitine transport system, but it cannot synthesize carnitine and in industrial fermentations it would be too expensive to add this component to the medium). In yeast, acetyl-CoA in the cytosol is produced from acetate that is derived from acetaldehyde, that is formed by de-carboxylation of pyruvate. Acetaldehyde can also be converted to ethanol by alcohol dehydrogenase, and during growth on glucose the majority of the glycolytic flux is directed towards ethanol due to the so-called Crabtree effect in yeast. Besides the main alcohol dehydrogenase (Adh1p) there are several alcohol dehydrogenases in *S. cerevisiae* that can catalyze the conversion of acetaldehyde to ethanol, and it is therefore inherently difficult to eliminate ethanol production in yeast. The only strategy that has worked so far is removing pyruvate decarboxylase activity through deletion of all three genes that encode for this activity, but this results in a strain that will require supplementation of acetate to the medium in order to meet the requirement for acetyl-CoA in the cytosol (needed for biosynthesis of fatty acids and ergosterol). Obviously, such a strain would be problematic to serve as a platform cell factory for acetyl-CoA derived products.

In the invention herein the normal route for conversion of pyruvate to acetyl-CoA through acetaldehyde in the cytosol is blocked through deletion of the three structural genes encoding pyruvate decarboxylase activity in yeast (PDC1, PDC5 and PDC6). This strain is auxotrophic for $C_2$ carbon sources such as acetate or ethanol, and it has been shown that this requirement is solely to fulfill the need for acetyl-CoA in the cytosol (required for production of cellular lipids). By removing pyruvate decarboxylase activity, the yeast cells can also not produce ethanol from glucose.

However, in the invention herein we have generated a yeast platform cell factory that can efficiently convert pyruvate to acetyl-CoA and combine this feature with elimination of pyruvate de-carboxylase activity, thereby establishing an efficient cytosolic acetyl-CoA producer that overproduces acetyl-CoA and at the same time cannot produce ethanol.

It is difficult to introduce direct pathways from pyruvate to acetyl-CoA efficiently into non-ethanol producing strains. However, the inventors of the present invention have identified several possible routes for this introduction that enable efficient introduction of a route from pyruvate to acetyl-CoA in a non-ethanol producing yeast strain. Strategies for reconstructing a synthetic pathway from pyruvate to acetyl-CoA, leading to a cell factory for overproducing acetyl-CoA, are described below:

1) Pyruvate Oxidase (PO) and Phosphate Acetyltransferase (PTA)

PO (EC 1.2.3.3) is a tetrameric flavoenzyme, each subunit contains one tightly and noncovalently bound FAD, thiamin diphosphate (TPP), and $Mg^{2+}$ for anchoring the diphosphate moiety of TPP. In the presence of phosphate and oxygen, PO catalyzes the conversion of pyruvate to acetyl-phosphate, hydrogen peroxide and carbon dioxide. The acetyl-phosphate produced in this reaction is then converted to acetyl-CoA by PTA. There are two classes of PTA enzyme, class I enzymes are about 350 residues in length, class II enzymes are about double this size. Class I enzymes share end-to-end homology with the C-terminal domain of class II enzymes. PO has been found in many species, PO genes from several organisms may be used, including *Lactobacillus plantarum, Streptococcus pneumoniae, Aerococcus viridans*. In some embodiments, the PTA enzyme can be a class I enzyme from *E. coli*, and/or is a class II enzyme from *Salmonella enterica*. Mutants of them can also be created for better catalysis efficiency. Hydrogen peroxide is produced in the conversion of PO. Due to its stress to cells, a catalase from yeast (or another organism) can be expressed or overexpressed to convert any hydrogen peroxide produced by PO to oxygen and water.

Accordingly, in a further embodiment, the invention provides a method of producing a microorganism (e.g., yeast) having increased production of cytosolic acetyl-CoA, comprising introducing into a microorganism (e.g., a yeast) (a) a deletion of the endogenous polynucleotides encoding pyruvate decarboxylase (PDC) (e.g., a deletion of PDC1, PDC5 and PDC6); (b) a polynucleotide encoding a polypeptide having the enzyme activity of pyruvate oxidase (PO) (e.g., PO from *Lactobacillus plantarum, Streptococcus pneumoniae*, and/or *Aerococcus viridians*), preferably *Aerococcus viridians*; and (c) a polynucleotide encoding a polypeptide having the enzyme activity of phosphate acetyltransferase (PTA) (e.g., from *E. coli, Salmonella enterica* subsp. *enterica* serovar *Typhimurium* LT2 and/or *Methanosarcina thermophile*), thereby producing a stably transformed microorganism having increased cytosolic acetyl-CoA production. In a further embodiment, the microorganism can additionally comprise a polynucleotide encoding a polypeptide having the enzyme activity of a catalase. In some embodiments, catalase can be from the microorganism being modified to have increased production of cytosolic acetyl-CoA (e.g., endogenous) (e.g., yeast catalase). In representative embodiments, the catalase can be overexpressed.

In an additional embodiment, the invention further provides a yeast having reduced pyruvate decarboxylase activity and increased acetyl-CoA production, comprising (a) a deletion of the endogenous polynucleotides encoding pyruvate decarboxylase (PDC) (e.g., a deletion of PDC1, PDC5 and PDC6); (b) a polynucleotide encoding a polypeptide having the enzyme activity of pyruvate oxidase (PO) (e.g., PO from *Lactobacillus plantarum, Streptococcus pneumoniae*, and/or *Aerococcus viridians*), preferably *Aerococcus viridians*; and (c) a polynucleotide encoding a polypeptide having the enzyme activity of phosphate acetyltransferase (PTA) (e.g., from *E. coli, Salmonella enterica* subsp. *enterica* serovar *Typhimurium* LT2 and/or *Methanosarcina thermophile*). In a further embodiment, the modified yeast can additionally comprise a polynucleotide encoding a polypeptide having the enzyme activity of a catalase. In some embodiments, catalase can be from yeast. In representative embodiments, the catalase can be overexpressed.

Figure 3:
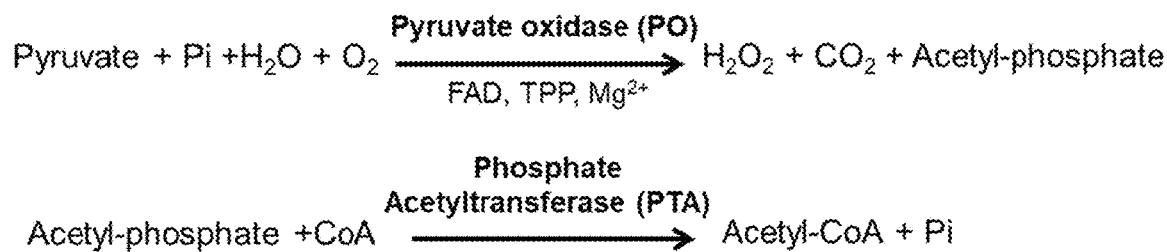
FIG. 3 shows the PO/PTA pathway.
Figure 4:
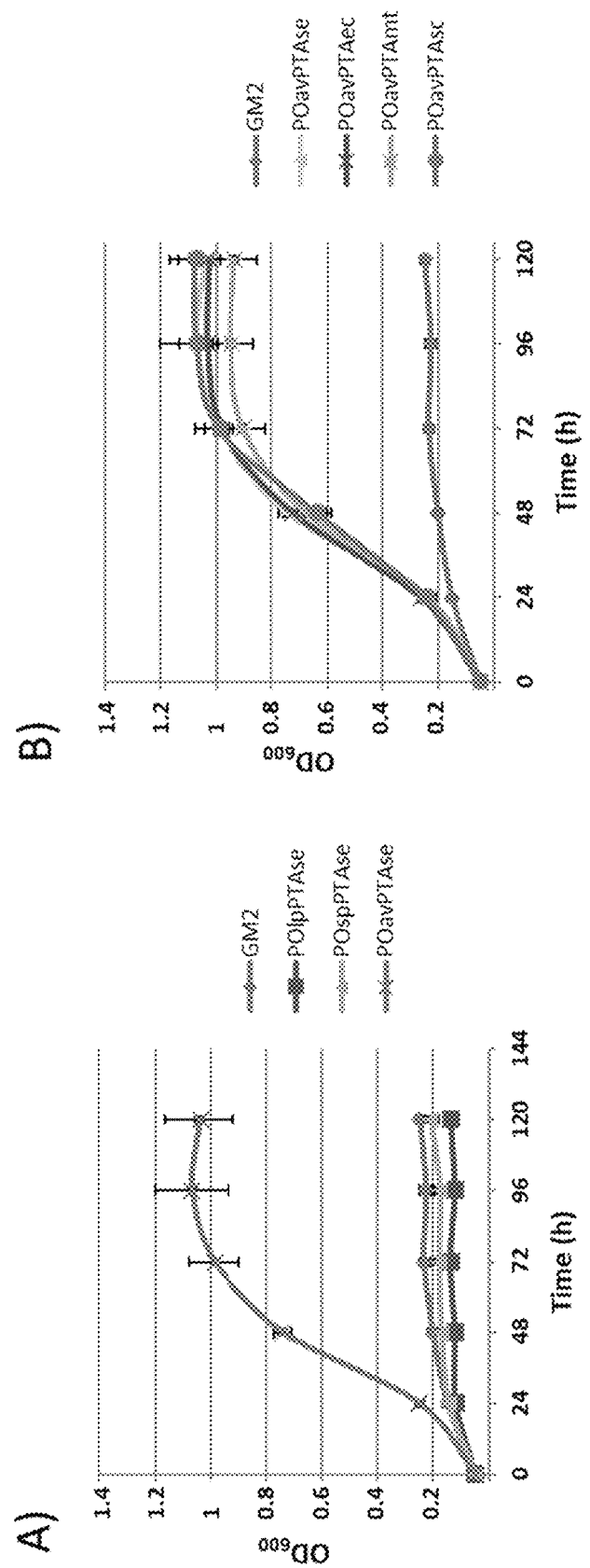
FIG. 4 shows that expression of the PO/PTA pathway leads to production of acetyl-CoA in the cytosol, as assessed via growth in glucose medium. A) Selection of optimal PO. PDC-strains were transformed with either an empty plasmid (GM2), or plasmids containing PTA from *Salmonella enterica* (PTAse) and PO from either *Lactobacillus plantarum* (POlp), *Streptococcus pneumonia* ($PO_{SP}$) or *Aerococcus viridians* (POav). B) Selection of optimal PTA. PDC-strains were transformed with either an empty plasmid (GM2), or plasmids containing PO from *Aerococcus viridians* (POav) and PTA from either *Salmonella enterica* subsp. *enterica* serovar *Typhimurium* LT2 (isoform 1 is PTAse, isoform 2 is PTAsc), *Escherichia coli* (PTAec) or *Methanosarcina thermophile* (PTAmt). All strains were grown on SD-ura medium with glucose. Improved growth of the strains on glucose was used as an indicator of pathway functionality.

The ability of the PO/PTA pathway (see FIG. 3) to supplement the acetyl-CoA requirement of PDC-negative strains was tested and the resulting data is shown in FIG. 4. Plasmids containing different combinations of PO and PTA from different sources were transformed into a PDC-negative strain and assessed for growth on SD-ura medium containing glucose. It was shown that strains containing PO from *Aerococcus viridians* (POav) and PTA from any of the sources examined grew significantly better than the control harbouring the empty plasmid (GM2), suggesting the PO/PTA pathway to be functional.

2) Pyruvate Ferredoxin Oxidoreductase (PFOR)

Figure 5:
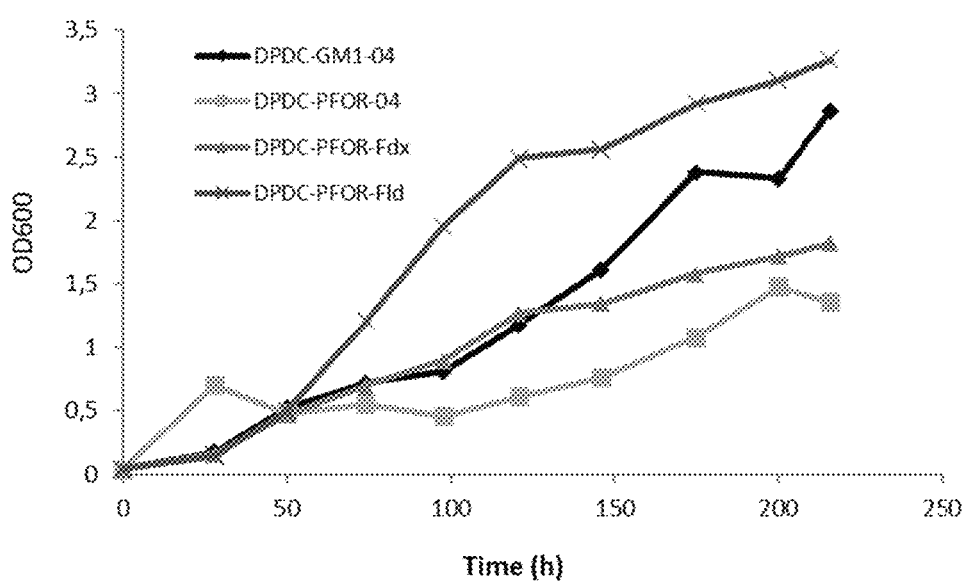
FIG. 5 shows co-expression of PFOR with either an empty HIS plasmid (GM1-04) or a plasmid containing ferredoxin and ferredoxin reductase (Fdx) or flavodoxin and ferredoxin reductase (Fld). Growth on 2% glucose in YPD media is used as an indicator of pathway functionality.

Expressing a bacterial pyruvate ferredoxin oxidoreductase (PFOR). Bacterial PFORs are usually homodimers and contain one to three iron-sulfur clusters. Like PDH, PFOR catalyzes the oxidative decarboxylation of pyruvate to acetyl-CoA using TPP as a cofactor. In contrast to PDH, the electron acceptor is ferredoxin. By co-expression of ferredoxin and ferredoxin reductase from *E. coli*, the electrons can be further transferred to $NADP^+$ resulting in the formation of NADPH. This reaction is reversible, involves the formation of a radical, and the enzyme is sensitive to oxygen. An exception is PFOR isolated from *Desulfovibrio africanus*, which shows an unusual high stability towards oxygen in vitro and is therefore considered as a good candidate for expression in yeast. The genes were originally cloned into plasmids under constitutively active promoters (pTEF1 or pPGK1) as described in example 2. In addition to testing fdx with fpr, the use of flavodoxin (fldA) instead of fdx was also tested. Testing of the function of PFOR together with fldA and fpr in a Δpdc1Δpdc5Δpdc6 mutant showed it to grow better on glucose compared to the deletion mutant transformed with an empty plasmid (FIG. 5).

In some aspects of the invention a method of producing a microorganism having increased production of cytosolic acetyl-CoA is provided, the method comprising introducing into a microorganism (e.g., a yeast): (a) a deletion of the endogenous polynucleotides encoding pyruvate decarboxylase (PDC) (e.g., a deletion of PDC1, PDC5 and PDC6); (b) a polynucleotide encoding a polypeptide having the enzyme activity of pyruvate ferredoxin oxidoreductase (PFOR) (e.g., pfor from *Desulfovibrio africanus*); and/or (c) one or more recombinant polynucleotides encoding a ferredoxin or a flavodoxin polypeptide and a ferredoxin reductase polypeptide (e.g., fdx and fpr from *E. coli* or fldA and fpr from *E. coli*), preferably a flavodoxin polypeptide and a ferredoxin reductase polypeptide, thereby producing a stably transformed microorganism having increased cytosolic acetyl-CoA production.

In still another aspect, the invention provides a yeast having reduced pyruvate decarboxylase activity and increased acetyl-CoA production, comprising (a) a deletion of the endogenous polynucleotides encoding pyruvate decarboxylase (PDC) (e.g., a deletion of PDC1, PDC5 and PDC6); (b) a polynucleotide encoding a polypeptide having the enzyme activity of pyruvate ferredoxin oxidoreductase (PFOR) (e.g., pfor from *Desulfovibrio africanus*); and/or (c) one or more recombinant polynucleotides encoding a ferredoxin or a flavodoxin polypeptide and a ferredoxin reductase polypeptide (e.g., fdx and fpr from *E. coli* or fldA and fpr from *E. coli*), preferably a flavodoxin polypeptide and a ferredoxin reductase polypeptide.

3) ATP-Citrate Lyase (ACL)

ATP-citrate lyase catalyses the conversion of citrate (derived from the mitochondria and transported to the cytosol) to oxaloacetate and acetyl-CoA. *S. cerevisiae* does not naturally contain this enzyme. Therefore, ATP-citrate lyase of a different organism, e.g. *Rhodosporidium toruloides*, mouse or human have to be heterologously expressed. To increase the production of citrate in the mitochondria, the pyruvate dehydrogenase subunit mutant Pda1 (S313A) with a mutated phosphorylation site (Oliveira et al, 2012, Molecular Systems Biology 8, 623) can be overexpressed together with the pyruvate transporters Mpc1, Mpc2 and CIT1. In order to recycle the oxaloacetate produced by ATP-citrate lyase in the cytosol, *S. cerevisiae* malate dehydrogenase Mdh3 without its peroxisomal targeting signal and NADP+-dependent malic enzyme, e.g. from *R. toruloides* can also be expressed.

Figure 6:
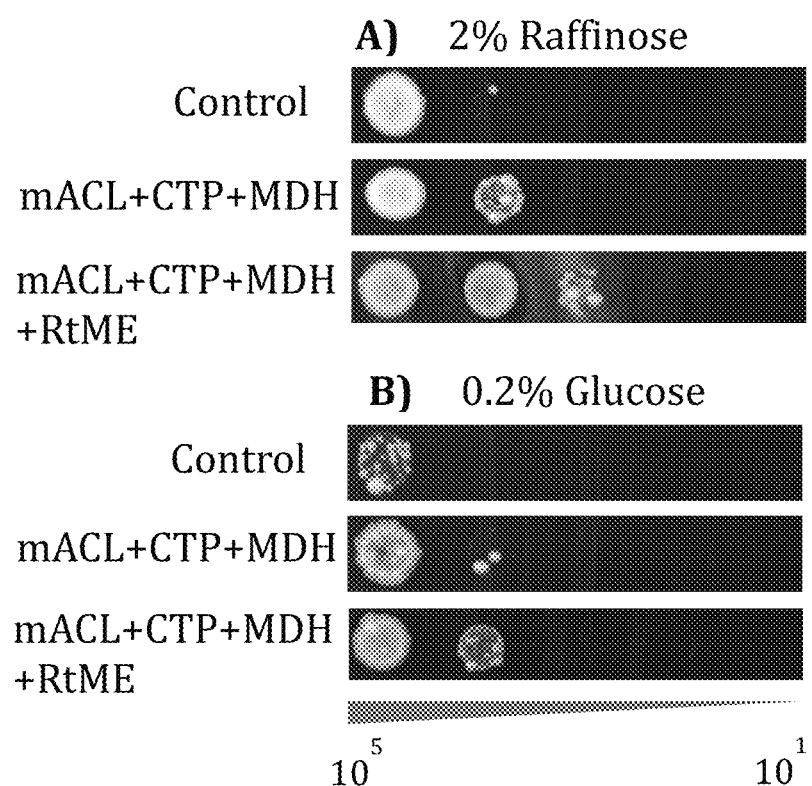
FIG. 6 shows that expression of the ACL pathway leads to production of acetyl-CoA in the cytosol through growth in either 2% raffinose (A) or 0.2% glucose medium (B). mACL is ATP-Citrate Lyase from *Mus musculus*; CTP and MDH are Citrate Transporter and Malate Dehydrogenease, respectively, from *Saccharomyces cerevisiae*; RtME is Malic Enzyme from *Rhodosporidium toruloides*.

Therefore, in some aspects of the invention, a method of producing a microorganism having increased production of cytosolic acetyl-CoA, comprising introducing into a microorganism (e.g., a yeast) (a) a deletion of the endogenous polynucleotides encoding pyruvate decarboxylase (PDC) (e.g., a deletion of PDC1, PDC5 and PDC6); and (b) a polynucleotide encoding a polypeptide having the enzyme activity of ATP-citrate lyase (from, e.g., *Rhodosporidium toruloides*, mouse or human). In a further embodiment, the method further comprises introducing (a) a polynucleotide encoding a polypeptide pyruvate dehydrogenase subunit mutant Pda1 (i.e., mutated phosphorylation site); (b) a polynucleotide encoding a polypeptide having the enzyme activity of one or more pyruvate transporters (e.g., Mpc1, Mpc2); and polynucleotide encoding a polypeptide having the enzyme activity of citrate synthase CIT1. In some embodiments, the pyruvate dehydrogenase subunit mutant polypeptide, the one or more pyruvate transporters and the citrate synthase can be overexpressed. In still further embodiments, the method further comprises introducing (a) malate dehydrogenase Mdh3 (absent its peroxisomal targeting signal) and NADP+-dependent malic enzyme (from, e.g., *Rhodosporidium toruloides*). In addition, the native citrate transporter from yeast (CTP1) might be overexpressed to improve transport of citrate from the mitochondria to the cytosol. FIG. 6 demonstrates functionality of the ACL pathway. PDC-negative strains were transformed with a plasmid encoding ACL from *Mus musculus* (mACL), CTP1 and MDH3 (without peroxisomal targeting signal) from *Saccharomyces cerevisiae* and ME from *Rhodosporidium toruloides* (RtME) and grown on solid media containing either 2% raffinose or 0.2% glucose. The strains containing the former ACL pathway exhibited significantly better growth compared to the control strain.

4) Pyruvate Dehydrogenase (PDH)

Expressing a cytosolic pyruvate dehydrogenase (PDH) complex. In *Escherichia coli*, PDH is an enzyme complex consisting of three enzymes: pyruvate dehydrogenase/decarboxylase (E1), dihydrolipoamide transacetylase (E2), and lipoamide dehydrogenase (E3). The octahedral core of the complex is formed by 24 E2 moieties, which can bind varying amounts of E1 and E3 dimers. As prosthetic groups, thiamine pyrophosphate (TPP) is bound to E1, lipoic acid to E2 and flavin adenine dinucleotide (FAD) to E3. E1 catalyses the binding of pyruvate to the TPP cofactor and $CO_2$ is released. The resulting hydroxyethyl group is transferred to the lipoamide disulfide of E2, thereby being oxidized to an acetyl group, which is finally coupled to coenzyme A. E3 then catalyses the reoxidation of the lipoamide disulfide using $NAD^+$ as electron acceptor. *S. cerevisiae* is not able to produce the cofactor lipoic acid in the cytosol. Besides expressing *E. coli* genes encoding enzymes E1-E3 (aceE, aceF, and lpd), it is therefore necessary to express genes responsible for the attachment and activation of the lipoyl group, which belong to the de novo pathway (lipA and lipB) in *E. coli*. This pathway is initiated with octanoic acid which is available as metabolite in the yeast cytosol. As an alternative, the salvage pathway that involves attachment of externally supplied lipoic acid through lipoateprotein ligase encoded by lplA will be expressed.

Yet another alternative strategy includes targeting the yeast PDH complex to the cytosol by removing the mitochondrial target signals of the different subunits. Genes that need to be modified and expressed include PDA1 (encoding the E1α subunit), PDB1 (encoding E1β), LAT1 (encoding E2), LPD1 (encoding E3) and PDX1 (encoding protein X). This could either be combined with one of the *E. coli* lipoic acid synthesis and attachment pathways or alternatively, the yeast de novo pathway (it does not seem to contain a salvage pathway) can be targeted to the cytosol as well. In this latter case, at least four additional genes are also modified (LIP2, LIP3, LIP5, and GCV3).

The PDH from *Azotobacter vinelandii* is an enzyme complex including three enzymes: pyruvate dehydrogenase/decarboxylase (E1p), dihydrolipoamide transacetylase (E2p), and lipoamide dehydrogenase (E3). This complex is the smallest one among the PDH family with 0.7 MDa, but its catalysis efficiency is as good as the larger one in *E. coli*. The PDH from *Enterococcus faecalis* is an enzyme complex including four enzymes: pyruvate dehydrogenase/decarboxylase alpha subunit (E1α), pyruvate dehydrogenase/decarboxylase (E1β), dihydrolipoamide transacetylase (E2) and lipoamide dehydrogenase (E3). This enzyme is active in aerobic and anaerobic condition. Compared with the PDH from *E. coli* and *A. vinelandii*, this enzyme has lower sensitivity to the $NADH/NAD^+$ ratio. The reaction mechanism is the same as for PDH in *E. coli*. For functional expression of these enzymes, the attachment and activation of the lipoyl group is also necessary. Besides expressing the PDH complex of *A. vinelandii*, the de novo pathway (lipA and lipB) is expressed. Another enzyme (acyl-acyl carrier protein synthetase) that can convert octanoic acid to octanoyl-ACP which is the substrate of de novo pathway is also expressed. There are two types ACP among different species. Most of the species have a type II ACP, but it is type I in yeast. Considering the substrate specificity of enzymes, type II ACP protein from *E. coli* (acpP) is co-expressed.

Accordingly, one aspect of the invention provides a method of producing a microorganism having increased production of cytosolic acetyl-CoA, comprising introducing into a microorganism (e.g., a yeast) (a) a deletion of the endogenous polynucleotides encoding pyruvate decarboxylase (PDC) (e.g., a deletion of PDC1, PDC5 and PDC6); (b) one or more recombinant polynucleotides encoding subunits of a cytosolic pyruvate dehydrogenase (PDH) complex (e.g., *E. coli* E1 (aceE), E2 (aceF), E3 (lpd), or *A. vinelandii* pyruvate dehydrogenase/decarboxylase (E1p), dihydrolipoamide transacetylase (E2p) and lipoamide dehydrogenase (E3), or *E. faecalis* pyruvate dehydrogenase/decarboxylase alpha subunit (E1α), pyruvate dehydrogenase/decarboxylase (E1β), dihydrolipoamide transacetylase (E2) and lipoamide dehydrogenase (E3)), preferably *A. vinelandii* pyruvate dehydrogenase/decarboxylase (E1p), dihydrolipoamide transacetylase (E2p) and lipoamide dehydrogenase (E3); and (c) one or more recombinant polynucleotides encoding polypeptides responsible for synthesis and/or attachment of the lipoyl group (e.g., *E. coli* lipA and lipB or *E. coli* lplA), thereby producing a stably transformed microorganism having increased cytosolic acetyl-CoA production.

A further aspect of the invention provides a method of producing a microorganism having increased production of cytosolic acetyl-CoA, comprising introducing into a microorganism (e.g., a yeast) (a) a deletion of the endogenous polynucleotide sequences encoding pyruvate decarboxylase (PDC) (e.g., a deletion of PDC1, PDC5 and PDC6); (b) one or more recombinant polynucleotides encoding subunits of a yeast pyruvate dehydrogenase (PDH) complex, wherein the yeast pyruvate dehydrogenase complex subunits are modified by removing the mitochondrial targeting sequences (e.g., PDA1 (encoding E1α), PDB1 (encoding E1β), LAT1 (encoding E2), LPD1 (encoding E3) and PDX1 (encoding protein X)); and either (c) one or more recombinant polynucleotide sequences encoding polypeptides responsible for attachment and activation of the lipoyl group derived from a heterologous host (e.g., E. coli lipA and lipB or E. coli lplA) or (d) one or more recombinant polynucleotide sequences encoding yeast polypeptides responsible for attachment and activation of the lipoyl group (LIP2, LIP3, LIP5 and GCV3) modified by removal of the mitochondrial targeting sequence to produce a stably transformed microorganism having increased cytosolic acetyl-CoA production, thereby producing a stably transformed microorganism having increased production of cytosolic acetyl-CoA.

In addition, microorganisms produced by the methods of this invention are provided. Accordingly, some aspects of the invention provide a yeast having reduced pyruvate decarboxylase activity and increased acetyl-CoA production, comprising (a) a deletion of the endogenous polynucleotide sequences encoding pyruvate decarboxylase (PDC) (e.g., a deletion of PDC1, PDC5 and PDC6); (b) one or more recombinant polynucleotides encoding subunits of a cytosolic pyruvate dehydrogenase (PDH) complex (e.g., E. coli E1 (aceE), E2 (aceF), E3 (lpd), or A. vinelandii pyruvate dehydrogenase/decarboxylase (E1p), dihydrolipoamide transacetylase (E2p) and lipoamide dehydrogenase (E3), or E. faecalis pyruvate dehydrogenase/decarboxylase alpha subunit (E1α), pyruvate dehydrogenase/decarboxylase (E1β), dihydrolipoamide transacetylase (E2) and lipoamide dehydrogenase (E3)), preferably A. vinelandii pyruvate dehydrogenase/decarboxylase (E1p), dihydrolipoamide transacetylase (E2p) and lipoamide dehydrogenase (E3); and (c) one or more recombinant polynucleotides encoding proteins responsible for synthesis and/or attachment of the lipoyl group (e.g., E. coli lipA and lipB or E. coli lplA).

Figure 7:
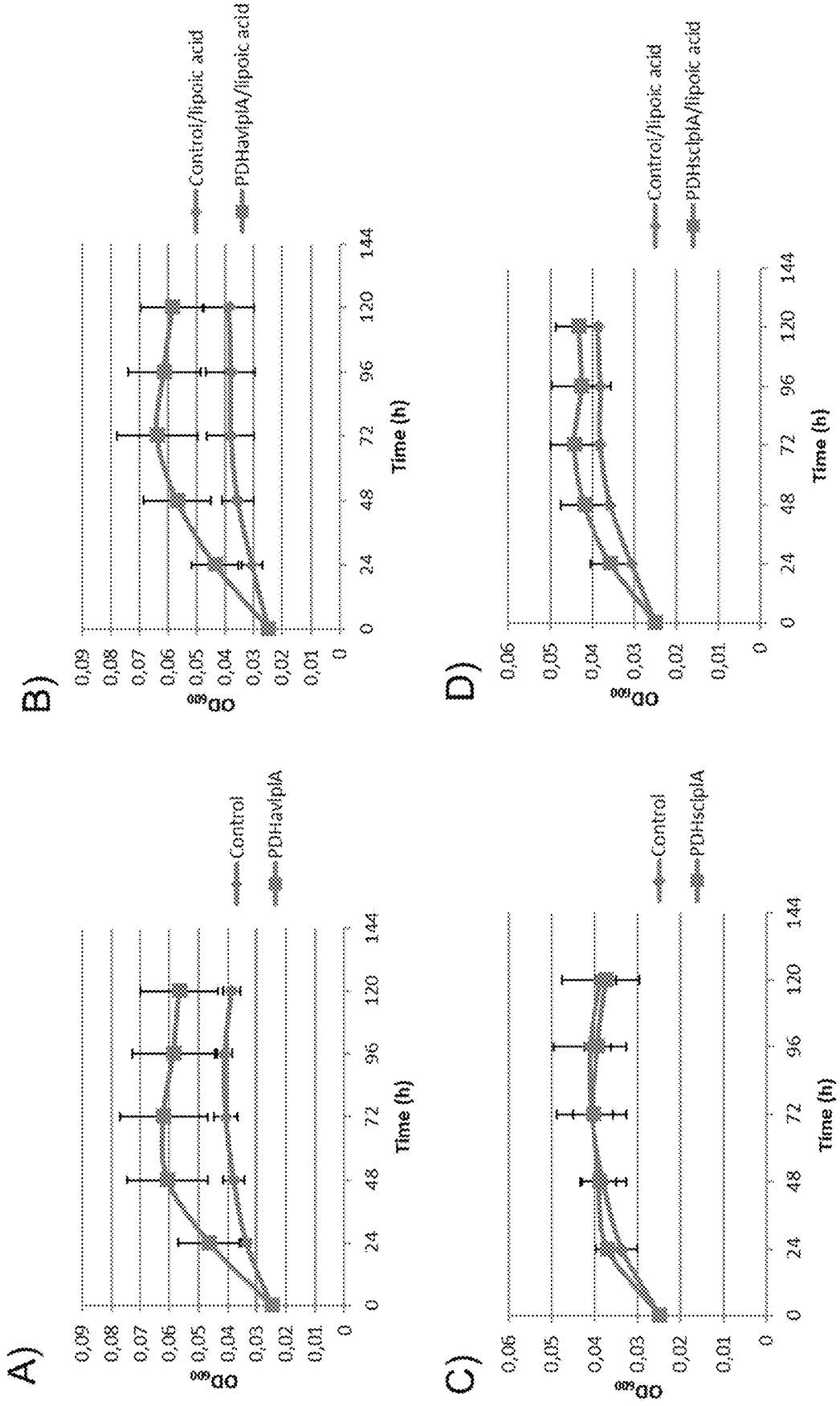
FIG. 7(A)-(D) show that co-expression of the PDH genes from *Azotobacter vinelandii*, but not from *S. cerevisiae*, together with lplA leads to production of acetyl-CoA in the cytosol. The addition of exogenous lipoic acid may further enhance production of acetyl-CoA.

In other embodiments, a yeast having reduced pyruvate decarboxylase activity and increased acetyl-CoA production is provided that comprises (a) a deletion of the endogenous polynucleotide sequences encoding pyruvate decarboxylase (PDC) (e.g., a deletion of PDC1, PDC5 and PDC6); (b) one or more recombinant polynucleotides encoding subunits of a yeast pyruvate dehydrogenase (PDH) complex, wherein the yeast pyruvate dehydrogenase complex subunits are modified by removing the mitochondrial targeting sequences (e.g., PDA1 (encoding E1α), PDB1 (encoding E1β), LAT1 (encoding E2), LPD1 (encoding E3) and PDX1 (encoding protein X)); and either (c) one or more recombinant polynucleotide sequences encoding proteins responsible for attachment and activation of the lipoyl group derived from a heterologous host (e.g., E. coli lipA and lipB or E. coli lplA) or (d) one or more recombinant polynucleotide sequences encoding yeast proteins responsible for attachment and activation of the lipoyl group (LIP2, LIP3, LIP5 and GCV3) modified by removal of the mitochondrial targeting sequence. FIG. 7 demonstrates functionality of the PDH pathway. PDH genes from either A. vinelandii (FIGS. 7A and B) or S. cerevisiae (mitochondrial targeting signal removed; FIGS. 7 C and D), as well as lplA gene (for lipoic acid salvage) were cloned into a plasmid and introduced into a PDC-negative strain. Strains were grown on glucose with (FIGS. 7 B and D) or without (FIGS. 7 A and C) lipoic acid supplement. Strains containing PDH genes from A. vinelandii exhibited improved growth compared to control strains, demonstrating pathway functionality.

An aspect of the embodiments relates to a yeast lacking any endogenous gene encoding pyruvate decarboxylase or comprising disrupted gene or genes encoding pyruvate decarboxylase. The yeast also comprises at least one heterologous pathway for synthesis of cytosolic acetyl-CoA. The at least one heterologous pathway comprises at least one heterologous gene encoding a respective enzyme involved in synthesis of acetyl-CoA, with the proviso that the at least one heterologous gene is not a heterologous gene encoding a pyruvate formate lyase.

In an embodiment, the at least one heterologous gene encodes a respective enzyme involved in the conversion of pyruvate into cytosolic acetyl-CoA.

In an embodiment, the yeast lacks endogenous genes encoding PDC1, PDC5 and/or PDC6 or comprises disrupted genes encoding PDC1, PDC5 and/or PDC6, preferably lacks endogenous genes encoding PDC1, PDC5 and PDC6, or comprises disrupted genes encoding PDC1, PDC5 and PDC6, to block conversion of pyruvate to ethanol.

In an embodiment, the yeast further comprises a heterologous gene encoding a pyruvate oxidase, and a heterologous gene encoding a phosphate acetyltransferase.

In a particular embodiment, the heterologous gene encoding the pyruvate oxidase is selected from the group consisting of a gene encoding a Lactobacillus plantarum pyruvate oxidase, a gene encoding a Streptococcus pneumonia pyruvate oxidase and a gene encoding an Aerococcus viridians pyruvate oxidase, preferably A. viridians pyruvate oxidase. In this particular embodiment, the heterologous gene encoding the phosphate acetyltransferase is selected from the group consisting of a gene encoding an Escherichia coli phosphate acetyltransferase, a gene encoding a Salmonella enterica phosphate acetyltransferase and a gene encoding a Methanosarcina thermophile phosphate acetyltransferase.

In a particular embodiment, the yeast further comprises a gene encoding a catalase, preferably a gene adapted for overexpression of Saccharomyces cerevisiae CTA1.

In an embodiment, the yeast further comprises a heterologous gene encoding a pyruvate ferredoxin oxidoreductase, a heterologous gene encoding a ferredoxin reductase, and a heterologous gene encoding a ferredoxin reductase substrate selected from the group consisting of ferredoxin and flavodoxin.

In a particular embodiment, the heterologous gene encoding the pyruvate ferredoxin oxidoreductase is a gene encoding a Desulfovibrio africanus pyruvate ferredoxin oxidoreductase, preferably D. africanus pfor. In this particular embodiment, the heterologous gene encoding the ferredoxin reductase is a gene encoding an Escherichia coli ferredoxin reductase, preferably E. coli fpr. In this particular embodiment, the heterologous gene encoding the ferredoxin reductase is a heterologous E. coli gene encoding said ferredoxin reductase substrate, preferably E. coli fdx or E. coli fldA, more preferably E. coli fldA.

In an embodiment, the yeast further comprises a heterologous gene encoding an adenosine triphosphate (ATP)-citrate lyase.

In a particular embodiment, the heterologous gene encoding the ATP-citrate lyase selected from the group consisting of a gene encoding a *Rhodosporidium toruloides* ATP-citrate lyase, a gene encoding a *Mus musculus* ATP-citrate lyase and a gene encoding a human ATP-citrate lyase, preferably a gene encoding a *M. musculus* ATP-citrate lyase.

In a particular embodiment, the yeast further comprises a heterologous gene encoding a pyruvate dehydrogenase subunit mutant having a mutated phosphorylation site, a gene encoding a pyruvate transporter, and a gene encoding a citrate synthase.

In a particular embodiment, the heterologous gene encoding said pyruvate dehydrogenase subunit mutant is a gene encoding a *Saccharomyces cerevisiae* pyruvate dehydrogenase subunit mutant having a mutated phosphorylation site, preferably *S. cerevisiae* Pda1 having a mutated phosphorylation site. In this particular embodiment, the gene encoding the pyruvate transporter is a gene encoding a *S. cerevisiae* pyruvate transporter, preferably *S. cerevisiae* Mpc1 or Mpc2. In this particular embodiment, the gene encoding said citrate synthase is a gene encoding a *S. cerevisiae* citrate synthase, preferably *S. cerevisiae* CIT1.

In a particular embodiment, the yeast further comprises a heterologous gene encoding a malate dehydrogenase lacking any peroxisomal targeting signal, and a heterologous gene encoding a nicotinamide adenine dinucleotide phosphate (NADP+)-dependent malic enzyme.

In a particular embodiment, the heterologous gene encoding the malate dehydrogenase lacking any peroxisomal targeting signal is a gene encoding a *Saccharomyces cerevisiae* malate dehydrogenase lacking any peroxisomal targeting signal, preferably *S. cerevisiae* Mdh3 lacking any peroxisomal targeting signal. In this particular embodiment, the heterologous gene encoding said NADP+-dependent malic enzyme is a gene encoding a *Rhodosporidium toruloides* NADP+-dependent malic enzyme.

In a particular embodiment, the yeast further comprises a gene adapted for overexpression of a citrate transporter, preferably a *Saccharomyces cerevisiae* citrate transporter, more preferably *S. cerevisiae* CTP1.

In an embodiment, the yeast comprises heterologous genes encoding a cytosolic pyruvate dehydrogenase complex, and heterologous genes encoding respective enzymes involved in attachment and activation of lipoyl groups to said cytosolic pyruvate dehydrogenase complex.

In an embodiment, the heterologous genes encoding the cytosolic pyruvate dehydrogenase complex are selected from the group consisting of genes encoding an *Escherichia coli* cytosolic pyruvate dehydrogenase complex, preferably *E. coli* aceE, aceF and lpd, genes encoding a *Saccharomyces cerevisiae* pyruvate dehydrogenase complex but lacking mitochondrial target signal (MTS), preferably *S. cerevisiae* PDA1, PDB1, LAT1, LPD1 and PDX1 lacking MTS, genes encoding an *Azotobacter vinelandii* pyruvate dehydrogenase complex, preferably *A. vinelandii* aceE$_{av}$, aceF$_{av}$ and lpdA$_{av}$, and genes encoding an *Enterococcus faecalis* pyruvate dehydrogenase complex, preferably *E. faecalis* pdhA, pdhB, aceF$_{ef}$ and lpdA$_{ef}$, more preferably, the pyruvate dehydrogenase complex are an *A. vinelandii* pyruvate dehydrogenase complex. In this particular embodiment, the heterologous genes encoding respective enzymes involved in attachment and activation of lipoyl groups are selected from the group consisting of genes encoding *Escherichia coli* lipoic acid synthetase and lipoic acid synthetase and/or lipoate-protein ligase, preferably *E. coli* lipA, and lipB and/or lplA, and genes encoding *Saccharomyces cerevisiae* LIP2, LIP3, LIP5 and GCV3 but lacking MTS.

Another aspect of the embodiments relates to a method of producing acetyl-CoA comprising culturing a yeast according to any of the embodiments in culture conditions suitable for production of cytosolic acetyl-CoA from the yeast.

In an embodiment, the method further comprises collecting the acetyl-CoA or a compound generated by the yeast from the acetyl-CoA from a culture medium in which the yeast is cultured and/or from the yeast. The compound is selected from a group consisting of fatty acids, 3-hydroxypropionic acid, isoprenoids, polyhydroxyalkanoates, 1-butanol and polyketides.

A further aspect of the embodiments relates to use of a yeast according to any of the embodiments for the production of cytosolic acetyl-CoA.

Yet another aspect of the embodiments relates to a method of producing a yeast suitable for the production of cytosolic acetyl-CoA. The method comprises deleting or disrupting any endogenous gene encoding pyruvate decarboxylase in the yeast. The method also comprises introducing, into the yeast, at least one heterologous pathway for synthesis of cytosolic acetyl-CoA. The at least one heterologous pathway comprises at least one heterologous gene encoding a respective enzyme involved in synthesis of acetyl-CoA, with the proviso that said at least one heterologous gene is not a heterologous gene encoding a pyruvate formate lyase.

As would be recognized by the skilled person, it is clear that the various modifications of the microorganisms of this invention described herein can be combined in any useful manner to produce a microorganism having increased production of cytosolic acetyl-CoA as well as other useful phenotypic and genetic traits. Thus, a microorganism (e.g., a yeast) having a deletion of the endogenous polynucleotides encoding pyruvate decarboxylase (PDC) can be further modified to comprise any of the polynucleotides described herein or those otherwise known in the art to provide useful traits.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

In the examples below references are made to several primers, these primers are to be found in Table 1.

Example 1

Deletion of the Three Structural Genes Encoding Pyruvate Decarboxylase Activity in Yeast (PDC1, PDC5 and PDC6)

PDC1, PDC5 and PDC6 were deleted using a bipartite strategy (Erdeniz et al., 1997). Two overlapping fragments of the kanMX resistance marker cassette flanked by loxP sites were amplified via PCR from plasmid pUG6 (Guldener et al., 1996) using primers 13-16. Sequences upstream and downstream of the individual genes were amplified using primers 1-12. Due to overlapping ends (introduced through the primer sequences) the PDC-upstream fragments could be fused to the 5' kanMX fragment and the 3' kanMX fragment to the individual PDC-downstream fragments by fusion PCR using the outer primers for amplification. The two overlapping PCR fragments thus generated for each gene deletion were transformed into yeast using the lithium acetate method (Gietz and Woods, 2002). After each gene deletion, the kanMX marker cassette was looped out via Cre recombinase mediated recombination between the two flanking loxP sites using plasmid pUC47 or pUG62 as described previously (Güldener et al., 1996).

PDC1, PDC5, and PDC6 were consecutively deleted in two different background strains: CEN.PK 113-5D (MATa ura3-52) and CEN.PK 110-10C (MATa his3-Δ1). This resulted in construction of strains YMZ-C1 (MATa ura3-52 pdc1Δ pdc5Δ pdc6Δ), and YMZ-A3 (MATα his3-Δ1 pdc6Δ). Strains YMZ-C1 and YMZ-A3 were crossed to generate YMZ-E1 (MATa ura3-52 his3-Δ1 pdc1Δ pdc5Δ pdc6Δ).

Example 2

Expressing Pyruvate Oxidase (PO) and Phosphate Acetyltransferase (PTA) in Cytosol Genes of PTA from *E. coli* (eutD) and from *S. enterica* (PTA$^{R252H}$ and PTA$^{G273D}$) were codon optimized for expression in yeast and synthesized by GenScript (Piscataway, N.J., USA). The gene sequences with introduced restriction sites can be found in Table 2. eutD and pta were digested with BamHI/NheI and cloned into the pSP-GM1 generating plasmid pZJ08 (eutD), pZJ09 (pta$^{R252H}$) and pZJ10 (pta$^{G273D}$). Genes of PO from *L. plantarum, S. pneumoniae, A. viridans* were codon optimized for expression in yeast and synthesized by GenScript (Piscataway, N.J., USA). The gene sequences with introduced restriction sites can be found in Table 2. The catalase gene from yeast itself (CTA1) was amplified from yeast genome, the TPI1 promoter and FBA1 terminator were amplified, three fragments were cloned into pZJ08, pZJ09 and pZJ10 generating plasmids pZJ11, pZJ12 and pZJ13. The PO genes were cut with NotI/PacI and cloned into pZJ11, pZJ12 and pZJ13 generating serial plasmids pZJ14 (eutD-catA1-PO$_{LP}$), pZJ15 (eutD-catA1-PO$_{SP}$), pZJ16 (eutD-catA1-PO$_{AV}$), pZJ17 (pta$^{R252H}$-catA1-PO$_{LP}$), pZJ18 (pta$^{R252H}$-catA1-PO$_{SP}$), pZJ19 (pta$^{R252H}$-catA1-PO$_{AV}$), pZJ20 (pta$^{G273D}$-catA1-PO$_{LP}$), pZJ21 (pta$^{G273D}$-catA1-PO$_{SP}$) and pZJ22 (pta$^{G273D}$-catA1-PO$_{AV}$). These plasmids were transformed into strain YMZ-E1 from example 1 to get strain YMZ-E1-14, YMZ-E1-15, YMZ-E1-16, YMZ-E1-17, YMZ-E1-18, YMZ-E1-19, YMZ-E1-20, YMZ-E1-21 and YMZ-E1-22. After evaluating the cell growth, the best (YMZ-E1-19) one was selected as the template for genomic integration. The expression cassette in pZJ19 was amplified using primers 13-14 and cloned into vector pXI-5 by CPEC cloning. The integration construct was separated from the vector backbone by XbaI restriction and transformed into YMZ-E1 generate YMZ-E1-19.

Example 3

Expressing a Bacterial Pyruvate Ferredoxin Oxidoreductase (PFOR)

Figure 8:
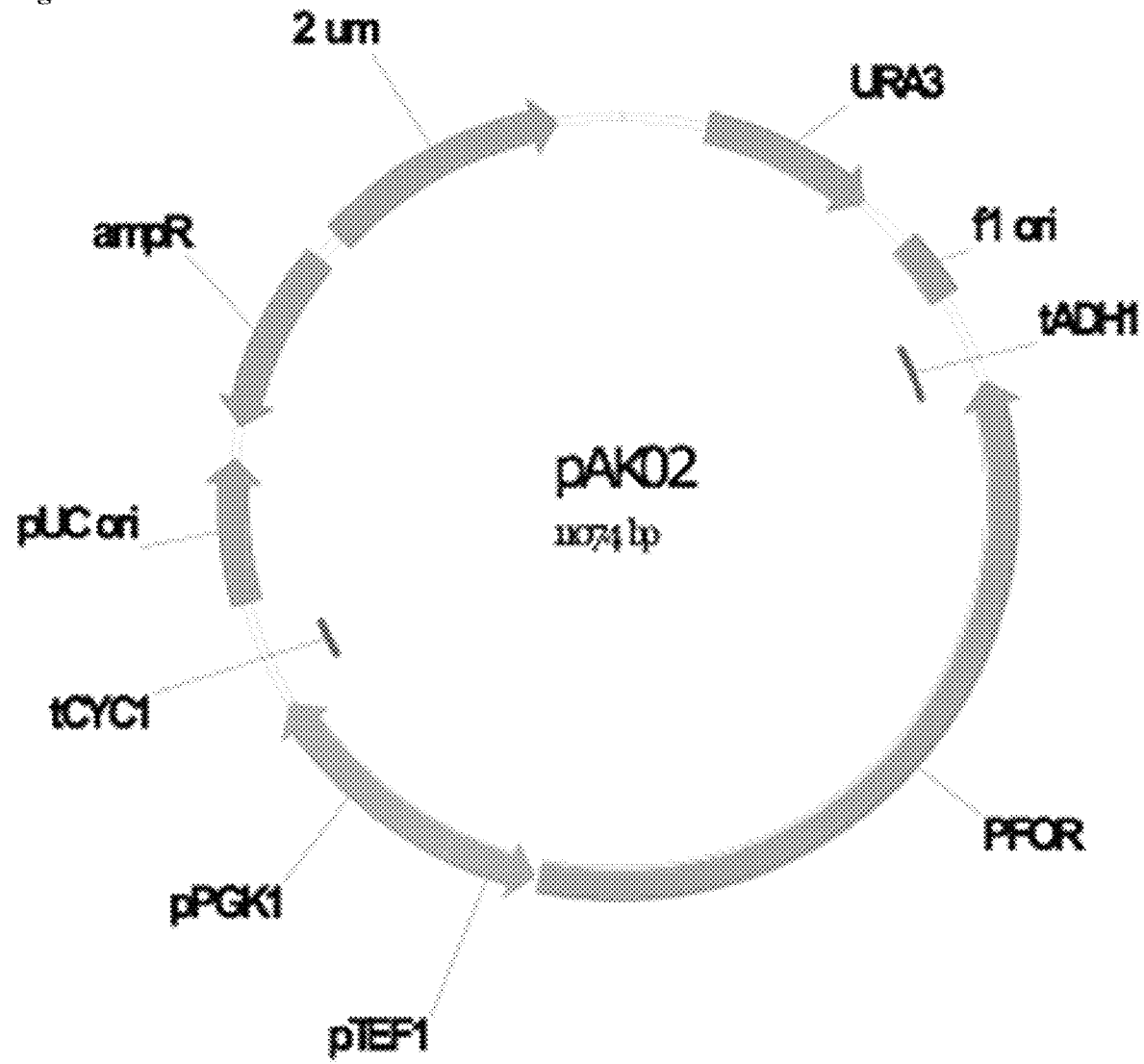
FIG. 8 shows the plasmid pAK02 described in example 3.

The gene pfor from *Desulfovibrio africanus* was codon optimised for expression in yeast and synthesized by GenScript. This gene was flanked by restriction sites for SpeI and SacI. The gene sequence can be found in Table 2. For expression in episomal plasmids, pfor was digested with SpeI/SacI and cloned into pSP-GM1 yielding pAK02 (FIG. 8).

Figure 9:
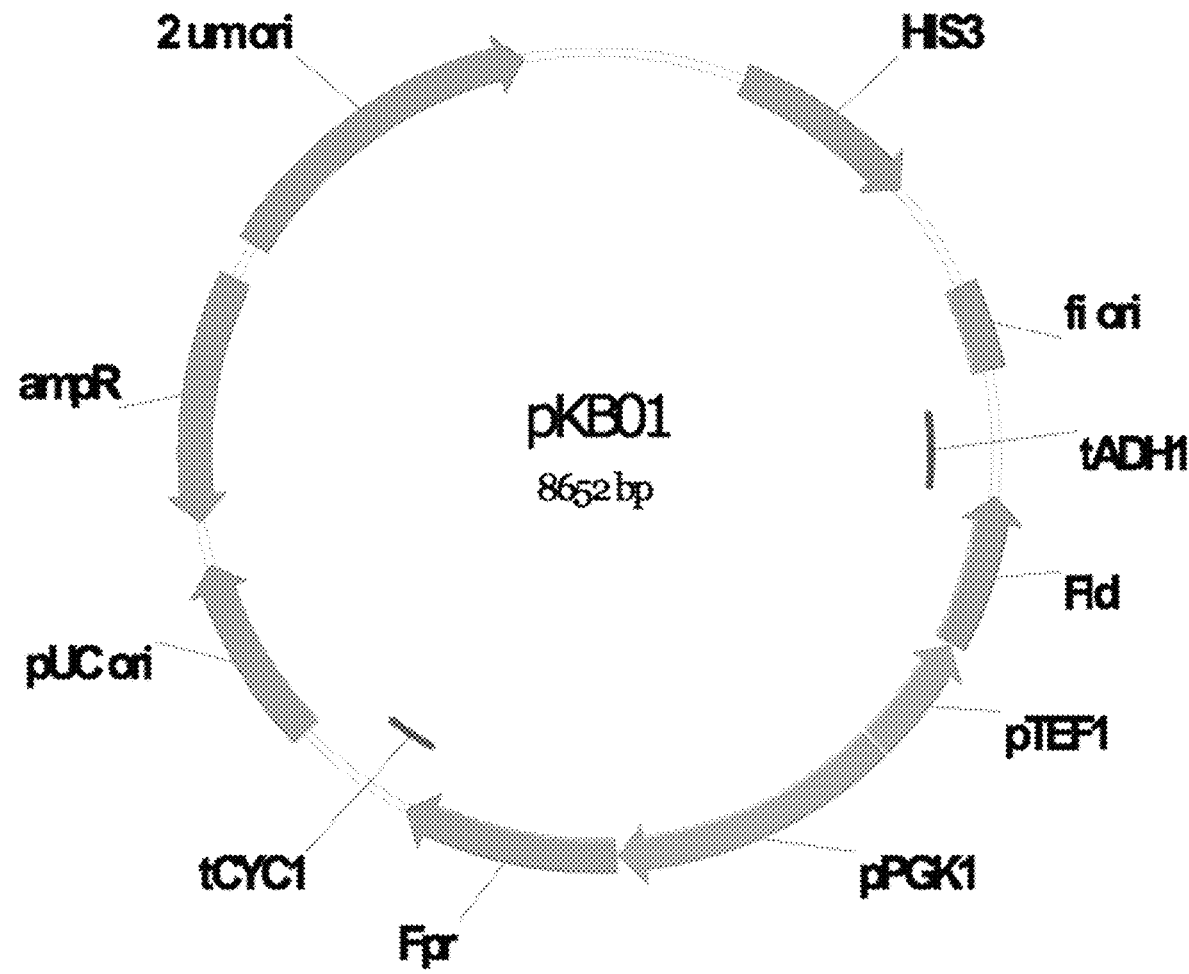
FIG. 9 shows the plasmid pKB01 described in example 3.

The genes fldA and fpr were amplified by PCR using *E. coli* DH5α genomic DNA as a template and primers 17-20. The NotI/SacI restricted fldA fragment and BamHI/XhoI restricted fpr fragment were cloned into pIYC04 generating pKB01 (FIG. 9).

Figure 10:
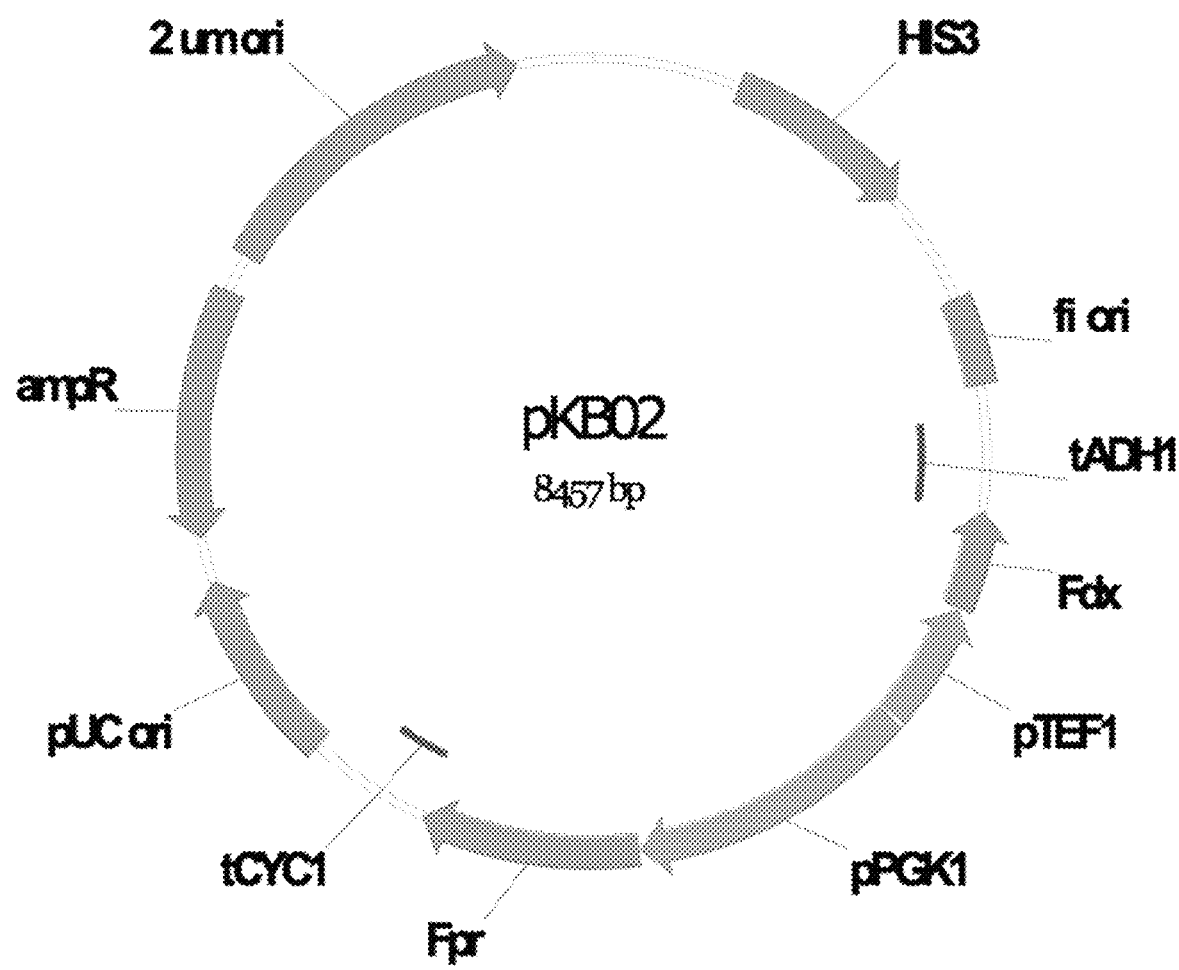
FIG. 10 shows the plasmid pKB02 described in example 3.

The *E. coli* gene coding for fdx was PCR-amplified using *E. coli* DH5α genomic DNA as a template and primers 60/61. This fragment was then restricted with NotI/SacI and cloned into pKB01 restricted with the same enzymes instead of fldA, yielding pKB02 (FIG. 10).

Example 4

Expressing ATP-Citrate Lyase (ACL) in the Cytosol

This example describes the alternative route to acetyl-CoA via the pyruvate dehydrogenase complex in the mitochondria and ATP citrate lyase in the cytosol. Pyruvate dehydrogenase subunit Pda1, mutant Pda1 (S313A) with a mutated phosphorylation site, pyruvate transporters Mpc1 (Seq ID P53157) and Mpc2 (Seq ID P38857) and citrate synthase (CIT1, Seq ID NP_014398) were overexpressed. This resulted in plasmids pPDH-B and pPDH-B' (containing the mutant Pda1) constructed according to Shao et al, 2009 and Zhou et al, 2012.

In order to establish cytosolic acetyl-CoA production, ATP citrate lyase was expressed for converting citrate to acetyl-CoA and oxaloacetate with consumption of one molecule of ATP. In order to recycle oxaloacetate to pyruvate, malate dehydrogenase gene MDH3 from *S. cerevisiae* (Seq ID P32419) (without its peroxisomal targeting signal) and NADP$^+$-dependent malic enzyme (eg. from *Rhodosporidium toruloides*, Seq ID M7WHN9) were cloned into expression vector pYX212 generating pCoA4. Citrate transporter (CTP1) from *S. cerevisiae* was also cloned into the same vector (Seq ID P38152). The ATP citrate lyase gene was selected from different organisms, such as *Rhodosporidium toruloides* (Seq ID M7WHC9), human (Seq ID P53396), mouse (Seq ID Q3V117), etc. The pathways were constructed according to Shao et al, 2009 and Zhou et al, 2012.

The cytosolic alternative acetyl-CoA pathway (pCoA4) and mitochondrial citrate synthesis pathway (pTDHB') were introduced into YMZ-E1. These two pathways increased the growth of *Saccharomyces cerevisiae* YMZ-E1 in raffinose media. Then cytosolic alternative acetyl-CoA pathway (pCoA4) and mitochondrial citrate synthesis pathway (pTDHB') were also introduced into *Saccharomyces cerevisiae* YMZ-E1 evolved for better growth (EXAMPLE 6) and a pdc1 pdc5 pdc6 mth1 strain (Oud et al. 2012). The combined alternative acetyl-CoA pathway improved the growth of both strains.

Example 5

Expressing a Pyruvate Dehydrogenase (PDH) Complex in the Cytosol

Figure 11:
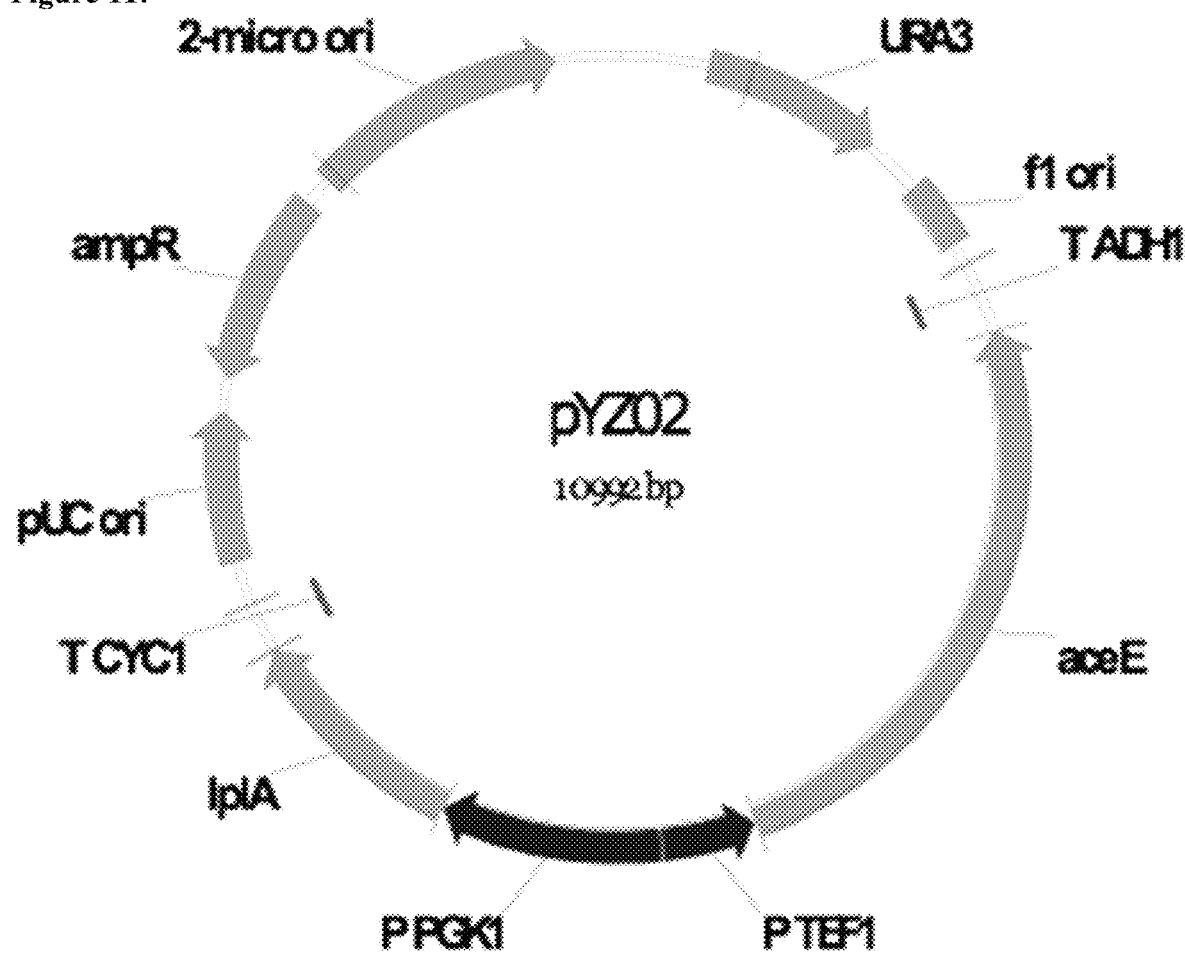
FIG. 11 shows the plasmid pYZ02 described in example 5.
Figure 12:
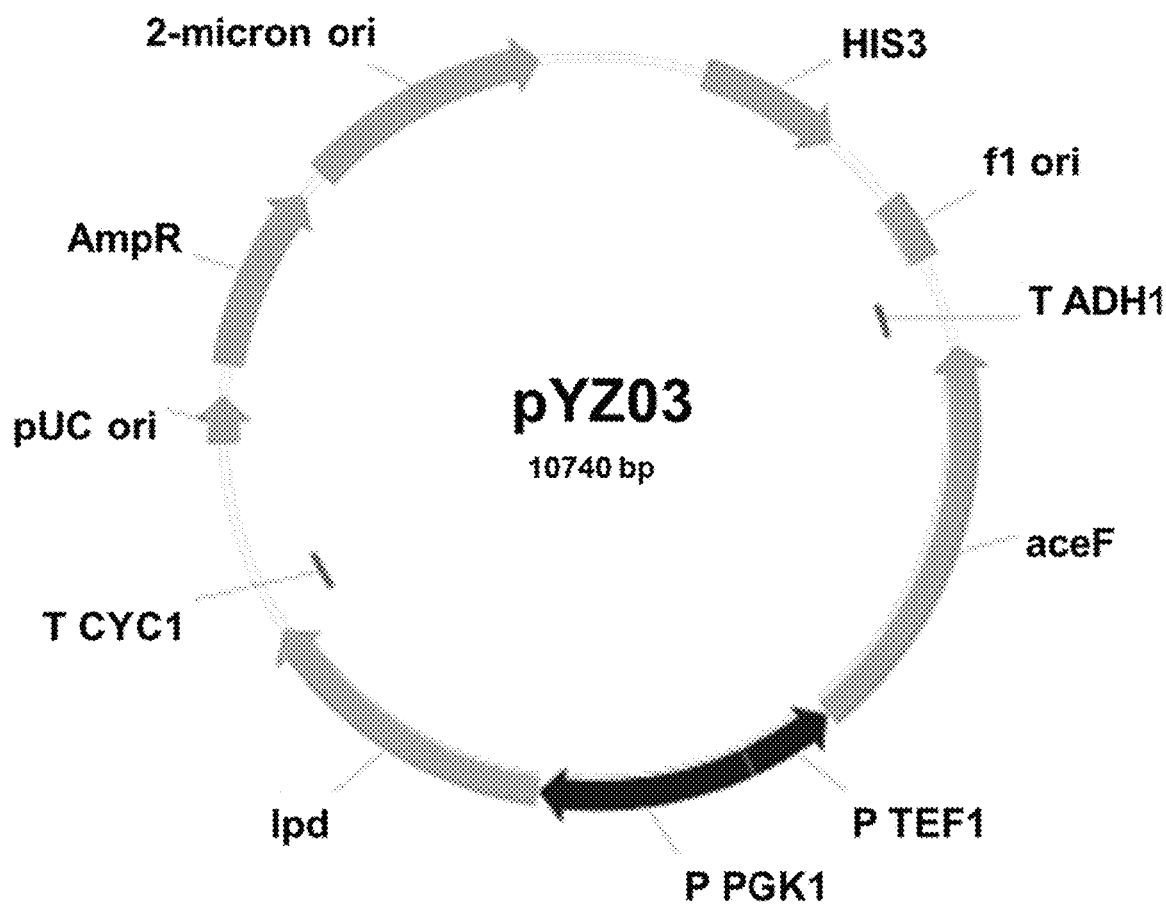
FIG. 12 shows the plasmid pYZ03 described in example 5.

The following genes were codon optimised for expression in yeast and synthesized by GenScript (Piscataway, N.J., USA): aceE, aceF, lpd, and lplA. The gene sequences including introduced restriction sites can be found in Table 2. For expression from episomal plasmids, aceE was restricted with SacI/NotI and cloned into vector pSP-GM1 (Chen et al., 2012a). LplA was cut with BamHI/XhoI and cloned into the same vector generating plasmid pYZ02 (Figure. 11). AceF was restricted with SacI/NotI and cloned into vector pIYCO4 (Chen et al., 2012b). Lpd was cut with BamHI/SalI and cloned into the same vector generating plasmid pYZ03 (FIG. 12). For integration into the genome, the aceE-lplA cassette including the bidirectional $P_{TEF1}$-$P_{PGK1}$ promoter was amplified via PCR from pSP-GM1-aceE-lplA in two fragments using primers 23-26 and cloned into vector pXI-3 (Mikkelsen et al., 2012) by Circular Polymerase Extension Cloning (CPEC) (Quan and Tian, 2011). The aceF-lpd cassette including the bidirectional $P_{TEF1}$-$P_{PGK1}$ promoter was amplified from pSP-GM1-aceE-lplA using primers 27-28 and cloned into vector pXI-5 (Mikkelsen et al., 2012) by CPEC cloning. Both integration constructs were separated from the vector backbone using NotI or XbaI restriction and transformed into strain YMZ-E1 from example 1. After each integration, strains that had lost the Kluyveromyces lactis (Kl) URA3 marker via recombination between its flanking direct repeats were selected on medium containing 5-fluoroorotic acid. This resulted in strain YMZ-E1-ecPDH.

For genomic integration of the E. coli lipoic acid synthesis and attachment pathway lipA and lipB were amplified from E. coli genomic DNA using PCR primers 29-32. The bidirectional $P_{TEF1}$-$P_{PGK1}$ promoter was PCR amplified from pSP-GM1 using primers 33/34. All three fragments were cloned into pXI-2 (Mikkelsen et al., 2012) by USER cloning (Nour-Eldin et al., 2006). The integration construct was separated from the vector backbone by NotI restriction and transformed into YMZ-E1-ecPDH to generate YMZ-E1-ecPDHlip.

To target the yeast PDH complex and the de novo lipoic acid synthesis and attachment pathway into the cytosol the following genes were amplified from yeast genomic DNA using primers 35-52: FDA1, PDB1, LAT1, LPD1, PDX1, LIP2, LIP3, LIP5, and GVC3. Two genes at a time were cloned together with the $P_{TEF1}$-$P_{PGK1}$ promoter (amplified from pSP-GM1 using primers 33/34) into different integration plasmids via Uracil Specific Excision Reagent (USER) cloning: PDA1 and LPD1 into pX-2, PDB1 and PDX1 into pX-3 (Mikkelsen et al., 2012), LIP2 and LIP-3 into pXI-2, and LIP5 and GVC3 into pXI-3. LAT1 was cloned together with the $P_{TEF1}$ promoter (amplified from pSP-GM1 using primers 33/53) into pX-4 (Mikkelsen et al., 2012). The PDA1-LPD1, PDB1-PDX1 and LAT1 integration constructs were separated from the vector by NotI restriction and consecutively integrated into the genome of YMZ-E1 to yield strain YMZ-E1-scPDH. After each integration, strains that had lost the KlURA3 marker via recombination between its flanking direct repeats were selected on medium containing 5-fluoroorotic acid. Likewise, the LIP2-LIP3 and LIP5-GCV3 constructs were integrated into YMZ-E1-scPDH to generate YMZ-E1-scPDHlip. To combine the yeast PDH complex with the E. coli de novo lipoic acid synthesis and attachment pathway, the lipA-lipB integration construct (see above) was integrated into YMZ-E1-scPDH to generate YMZ-E1-scPDHeclip.

Genes of PDH from A. vinelandii were codon optimized for expression in yeast and synthesized by GenScript (Piscataway, N.J., USA): $aceE_{av}$, $aceF_{av}$, and $lpdA_{av}$. The gene sequences with introduced restriction sites can be found in Table 2. For expression from episomal plasmids, $aceF_{av}$ was restricted with PacI/NotI and cloned into vector pSP-GM1 generating plasmid pZJ01. $aceF_{av}$ was restricted with SacI/NotI and cloned into vector pIYC04. $lpdA_{av}$ was cut with BamHI/SalI and cloned into the same vector generating plasmid pZJ02. For integration into the genome, the $aceF_{av}$ cassette with TEF1 promoter and ADH1 terminator was PCR amplified from pSP-GM1-$aceE_{av}$ in two fragments using primers 1-2 and cloned into vector pXI-3 by CPEC cloning. The $aceF_{av}$-$lpdA_{av}$ cassette including the bidirectional $P_{TEF1}$-$P_{PGK1}$ promoter was amplified from pSP-GM1-$aceF_{av}$-$lpdA_{av}$ using primers 3-4 and cloned into vector pXI-5 by CPEC cloning. Both integration constructs were separated from the vector backbone using NotI or XbaI restriction and transformed into strain YMZ-E1 from example 1. After integration, strains that had lost the Kluyveromyces lactis (Kl) URA3 marker via recombination between its flanking direct repeats were selected on medium containing 5-fluoroorotic acid. This resulted in strain YMZ-E1-avPDH.

Genes of PDH from E. faecalis were codon optimized for expression in yeast and synthesized by GenScript (Piscataway, N.J., USA): pdhA, pdhB, $aceF_{ef}$, and $lpdA_{ef}$. The gene sequences with introduced restriction sites can be found in Table 2. For expression from episomal plasmids, pdhA was restricted with SacI/NotI and cloned into vector pSP-GM1. pdhB from E. coli was cut with BamHI/XhoI and cloned into the same vector generating plasmid pZJ03. $aceF_{ef}$ was restricted with SacI/NotI and cloned into vector pIYC04. $lpdA_{ef}$ was cut with BamHI/XhoI and cloned into the same vector generating plasmid pZJ04. For integration into the genome, the pdhA-pdhB cassette including the bidirectional $P_{TEF1}$-$P_{PGK1}$ promoter was PCR amplified from pSP-GM1-pdhA-pdhB in two fragments using primers 5-8 and cloned into vector pXI-3 by CPEC cloning. The $aceF_{ef}$-$lpdA_{ef}$ cassette including the bidirectional $P_{TEF1}$-$P_{PGK1}$ promoter was amplified from pSP-GM1-$aceF_{ef}$-$lpdA_{ef}$ using primers 9-10 and cloned into vector pXI-5 by CPEC cloning. Both integration constructs were separated from the vector backbone using NotI or XbaI restriction and transformed into strain YMZ-E1 from example 1. After integration, strains that had lost the Kluyveromyces lactis (Kl) URA3 marker via recombination between its flanking direct repeats were selected on medium containing 5-fluoroorotic acid. This resulted in strain YMZ-E1-efPDH. For genomic integration of the E. coli lipoic acid synthesis and attachment pathway lipA and lipB were amplified from E. coli genomic DNA using primer numbers 29-32. lipA was digested with NotI/PacI and cloned into the pSP-GM1, lipB was cut with BamHI/XhoI and cloned into the same vector generating plasmid pZJ05. The acyl-acyl carrier protein synthetase from Vibrio harveyi (aasS) and acpP from E. coli was digested with NotI/PacI and BamHI/XhoI respectively and cloned into pSP-GM1 to generate plasmid pZJ06. The directional expression cassette in pZJ06 was amplified and cut with BspEI/SgrAI and cloned into pZJ05 generating plasmid pZJ07. The four gene expression cassette was cloned into pXI-2 by USER cloning. The integration construct was separated from the vector backbone by XbaI restriction and transformed into YMZ-E1-avPDH and YMZ-E1-efPDH to generate YMZ-E1-avPDHlip and YMZ-E1-efPDHlip, respectively.

Example 6

Strain Cultivation and Evolution

PDC deletion strains containing the introduced pyruvate to AcCoA conversion system, according to the examples above, were initially cultivated on yeast extract peptone dextrose (YPD) liquid media in either shake-flasks or tubes and their growth was compared to strains containing the PDC deletion alone to evaluate system function.

Next, strains were evolved to increase growth on glucose as the sole carbon source in minimal media. This involved two phases. In the first phase, strains were cultivated in shake flasks in YP medium (10 g/L yeast extract, 20 g/L peptone) containing 1.4% glucose and 0.6% ethanol. Strains were serially transferred every 48 hours or 24 hours, and the ethanol concentration was gradually decreased until glucose became the sole carbon source in the media. The growth rate of the strains was occasionally determined to evaluate their adaptation level of glucose tolerance.

Once fast-growing, glucose tolerant strains were obtained in YPD media, they were further evolved for growth on minimal media. The strains were cultivated in minimal media (Verduyn et al., 1992) containing 2% glucose and serially transferred every 24 hours. The growth rate of strains was occasionally determined to evaluate their adaptation level.

REFERENCES

Chen, Y., Partow, S., Scalcinati, G., Siewers, V., Nielsen, J., 2012a. Enhancing the copy number of episomal plasmids in Saccharomyces cerevisiae for improved protein production. FEMS Yeast Res. 12, 598-607. Chen, Y., Daviet, L., Schalk, M, Siewers, V, Nielsen, J., 2012b. Establishing a platform cell factory through engineering of yeast Acetyl-CoA metabolism. under revisionErdeniz, N., Mortensen, U. H., Rothstein, R., 1997. Cloning-free PCRbased allele replacement methods. Genome Res. 7, 1174-1183. Gietz, R. D., Woods, R. A., 2002. Transformation of yeast by lithium acetate/single-stranded carrier DNA/polyethylene glycol method. Meth. Enzymol. 350, 87-96. Giildener, U., Heck, S., Fiedler, T., Beinhauer, J., Hegemann, J. H., 1996. A new efficient gene disruption cassette for repeated use in budding yeast. Nucleic Acids Res. 24, 2519-2524. Mikkelsen, M. D, Buron, L. D., Salomonsen, B., Olsen, C. E., Hansen, B. G., Mortensen, U. H., Halkier, B. A., 2012. Microbial production of indolylglucosinolate through engineering of a multi-gene pathway in a versatile yeast expression platform. Metab Eng. 14, 104-11. Nour-Eldin, H., Hansen, B., Norholm, M., Jensen, J., Halkier, B., 2006. Advancing uracil-excision based cloning towards an ideal technique for cloning PCR fragments. Nucleic Acids Res. 34, E122. Oud B., Flores C. L., Gancedo C., Zhang X., Trueheart J., Daran J. M., Pronk J. T., van Maris A. J., 2012. An internal deletion in MTH1 enables growth on glucose of pyruvate-decarboxylase negative, non-fermentative Saccharomyces cerevisiae. Microb Cell Fact. 11, 131. Quan, J., Tian, J., 2011. Circular polymerase extension cloning for high-throughput cloning of complex and combinatorial DNA libraries. Nat Protoc. 6, 242-51. Shao, Z., Zhao, H., Zhao, H., 2009. DNA assembler, an in vivo genetic method for rapid construction of biochemical pathways. Nucleic Acids Res. 37(2), e16. Verduyn, V., Postma, E., Scheffers, W. A., Van Dijken, J. P., 1992. Effect of benzoic acid on metabolic fluxes in yeasts: A continuous-culture study on the regulation of respiration and alcoholic fermentation. Yeast 8, 501-517.

TABLE 1

Primer sequences.

| Primer # | Primer name | Sequence 5'-3' | SEQ ID NO |
|---|---|---|---|
| 1 | pdc1-up-fw | TACTTGCTATCGTTCAACAC | 1 |
| 2 | pdc1-up-rev | CAGCGTACGAAGCTTCAGTGCGTGAGGTTATGAGTAG | 2 |
| 3 | pdc1-dw-fw | GTGATATCAGATCCACTAGTACCAACGCTAAGCAATAAG | 3 |
| 4 | pdc1-dw-rev | CCTTGGTTCCACTAATTCATC | 4 |
| 5 | pdc5-up-fw | TTAGGCATAATCACCGAAGA | 5 |
| 6 | pdc5-up-rev | CAGCGTACGAAGCTTCAGGAGAGGAAAGGACTTACTACA | 6 |
| 7 | pdc5-dw-fw | GTGATATCAGATCCACTAGTTCTGTCCTGTCTTCCAG | 7 |
| 8 | pdc5-dw-rev | GGTGCTCTACTGGTGATT | 8 |
| 9 | pdc6-up-fw | ACATCTTCCAAGCATCTCAT | 9 |
| 10 | pdc6-up-rev | CAGCGTACGAAGCTTCAGGAATCGCACCATATCCCTTA | 10 |
| 11 | pdc6-dw-fw | GTGATATCAGATCCACTAGCGTTATCGCCGTGAATTAC | 11 |
| 12 | pdc6-dw-rev | TTGGTTGTAGATGGTGGTG | 12 |
| 13 | kanMX_1_fw | CTGAAGCTTCGTACGCTG | 13 |
| 14 | kanMX_1_rev | TCACCATGAGTGACGACTGA | 14 |

TABLE 1-continued

Primer sequences.

| Primer # | Primer name | Sequence 5'-3' | SEQ ID NO |
|---|---|---|---|
| 15 | kanMX_2_fw | TTCCAACATGGATGCTGAT | 15 |
| 16 | kanMX_2_rev | CTAGTGGATCTGATATCAC | 16 |
| 17 | fpr-BamHI-fw | GTTGTTGGATCCCAGGAGAAAAACATGGCTGA | 17 |
| 18 | fpr-XhoI-rev | GTTGTTCTCGAG CGTTTATCGATAAGTAACCGCT | 18 |
| 19 | fldA-NotI-fw | GTTGTTGCGGCCGCGAGGTTATTTCACTCATGGCT | 19 |
| 20 | fldA-SacI-rev | GTTGTTGAGCTCCATCACATCAGGCATTGAGA | 20 |
| 23 | aceE-lplA1 | CGCTTATTTAGAAGTGTCAACAACGTATCTACAGCTCTCAGGCTAATCTA | 21 |
| 24 | aceE-lplA2 | GAAAGCATAGCAATCTAATCTAAGTTTTAATTACAACGCAAAACAATGTCAGA | 22 |
| 25 | aceE-lplA3 | GCGTTGTAATTAAAACTTAG | 23 |
| 26 | aceE-lplA4 | TCCTTCCTTTTCGGTTAGAGCGGATCTATCTTACAGCACCAGC | 24 |
| 27 | aceF_lpd_1 | CGCTTATTTAGAAGTGTCAACAACGTATCTACAGAGCTCTTACATGACT | 25 |
| 28 | aceF_lpd_2 | TCCTTCCTTTTCGGTTAGAGCGGATACCTACTTCTTCTTGGCT | 26 |
| 29 | G1-lipA-fw | AGCGATACGUATGAGTAAACCCATTGTGATGGAA | 27 |
| 30 | G1-lipA-rv | CACGCGAUTTACTTAACTTCCATCCCTTTCGC | 28 |
| 31 | G2-lipB-fw | ATCAACGGGUATGTATCAGGATAAAATTCTTGTCCG | 29 |
| 32 | G2-lipB-rv | CGTGCGAU TTAAGCGGTAATATATTCGAAGTCC | 30 |
| 33 | P1-TEF1 | ACGTATCGCUTTGTAATTAAAACTTAGATTAGATTGCTATG | 31 |
| 34 | P2-PGK1 | ACCCGTTGAUTTGTTTTATATTTGTTGTAAAAAGTAGATAATTAC | 32 |
| 35 | G1-PDA1-fw | AGCGATACGUATGGCAACTTTAAAAACAACTGATAAG | 33 |
| 36 | G1-PDA1-rv | CACGCGAUTTAATCCCTAGAGGCAAAACCTTG | 34 |
| 37 | G2-LPD1-fw | ATCAACGGGUATGGTAGTCATCATCGGTGGTGGC | 35 |
| 38 | G2-LPD1-rv | CGTGCGAUTCAACAATGAATAGCTTTATCATAGGC | 36 |
| 39 | G1-PDB1-fw | AGCGATACGUATGTCATCAACAAAGACGATGACCG | 37 |

TABLE 1-continued

Primer sequences.

| Primer # | Primer name | Sequence 5'-3' | SEQ ID NO |
|---|---|---|---|
| 40 | G1-PDB1-rv | CACGCGAUTTATTCAATTGACAAGACTTCTTTGAC | 38 |
| 41 | G2-PDX1-fw | ATCAACGGGUATGTCAGCTAAATTACTTGCTGTAAAGACA | 39 |
| 42 | G2-PDX1-rv | CGTGCGAUTCAAAATGATTCTAACTCCCTTACG | 40 |
| 43 | G1-LAT1-fw | AGCGATACGUATGTACGCATCGTACCCAGAGCA | 41 |
| 44 | G1-LAT1-rv | CACGCGAUTCACAATAGCATTTCCAAAGGATT | 42 |
| 45 | G1-LIP2-fw | AGCGATACGUATGTTCAATGTCTGTAGGCGACAATG | 43 |
| 46 | G1-LIP2-rv | CACGCGAUTCACGGATTCTTTTTCAAAATATTG | 44 |
| 47 | G2-LIP3-fw | ATCAACGGGUATGGTGGGACAGCGAAACCTCATA | 45 |
| 48 | G2-LIP3-rv | CGTGCGAUTTATGTGTAACTGTCAATATTCTCCAAA | 46 |
| 49 | G1-LIP3-fw | AGCGATACGUATGAATGCATTGAATACTGATTCAGATAACG | 47 |
| 50 | G1-LIP5-rv | CACGCGAUTTATTTCATGTTTCTTTTCTTCAAAACG | 48 |
| 51 | G2-GCV3-fw | ATCAACGGGUATGACTTCCCAACATGAGTGGATAGC | 49 |
| 52 | G2-GCV3-rv | CGTGCGAUTCAGTCATCATGAACCAGTGTCTTT | 50 |
| 53 | TEF1-fw | CGTGCGAUGCACACACCATAGCTTCAAAATG | 51 |
| 54 | G1-FDH1-fw | AGCGATACGUATGTCGAAGGGAAAGGTTTTG | 52 |
| 55 | G1-FDH1-rv | CACGCGAUTTATTTCTTCTGTCCATAAGCTCTGG | 53 |
| 56 | G1-Crpfl-fw | AGCGATACGUATGTTAACACCCTTAAGCTATCCTATC | 54 |
| 57 | G1-Crpfl-rv | CACGCGAUTTACATGGTGTCGTGGAAGGTG | 55 |
| 58 | G2-CrpflA-fw | ATCAACGGGUATGTTGAAGGCTGCGTTGC | 56 |
| 59 | G2-CrpflA-rv | CGTGCGAUTCACTCGGCGCAGATGACG | 57 |
| 60 | fdx-Not1-fw | ATCGAAGCGGCCGCAAAACAATGCCAAAGATTGTTATTTTGC | 58 |

TABLE 1-continued

Primer sequences.

| Primer # | Primer name | Sequence 5'-3' | SEQ ID NO |
|---|---|---|---|
| 61 | fdx-SacI-rev | ATCGTCGAGCTCTTAATGCTCACGCGCATG | 59 |
| 62 | fdx-F1 | CAACAACGTATCTACCAACGGAATGCGTGCGATTTAATGCTCACGCGCATGGTTGATAG | 60 |
| 63 | fldA-F1 | CAACAACGTATCTACCAACGGAATGCGTGCGATTCAGGCATTG AGAATTTCGTCGAGATG | 61 |
| 64 | FdR-R1 | CTTTTCGGTTAGAGCGGATGAATGCACGCGTTACCAGTAATGCTCCGCTGTCATA | 62 |

TABLE 2

Codon optimized gene sequences (start and stop codons are underlined)

| | | |
|---|---|---|
| aceE | GAATTCGCATAGCAATCTAATCTAAGTTTTAATTACAAGCGGCCGCAAAACA<br>ATGTCAGAAAGATTCCCAAACGATGTCGATCCAATAGAAACAAGAGACTGGTTACAAGCAATAGAAAGTGTCATAAGAGAAGAAGGTGTTGAAAGAGCACAATATTTGATCGATCAATTGTTAGCCGAAGCTAGAAAAGGTGGTGTCAATGTTGCTGCAGGTACTGGTATCTCTAACTACATCAACACAATACCAGTTGAAGAACAACCAGAATACCCTGGTAATTTGGAATTAGAAAGAAGAATTAGATCAGCAATCAGATGGAACGCCATTATGACCGTTTTGAGAGCTTCCAAAAGGATTTGGAATTAGGTGGTCATATGGCAAGTTTTCAATCTTCAGCCACTATATACGATGTATGTTTCAACCACTTTTTCAGAGCAAGAAACGAACAAGATGGTGGTGACTTAGTATACTTTCAAGGTCATATTTCTCCAGGTGTCTATGCAAGAGCCTTCTTGGAAGGTAGATTAACACAAGAACAATTGGATAACTTCAGACAAGAAGTACATGGTAACGGTTTATCCAGTTATCCACACCCTAAATTGATGCCAGAATTTTGGCAATTCCCTACTGTCTCTATGGGTTTAGGTCCTATAGGTGCAATCTACCAAGCCAAATTCTTGAAGTATTTGGAACATAGAGGTTTGAAGGATACATCTAAGCAAACCGTTTACGCATTTTTGGGTGACGGTGAAATGGACGAACCAGAATCAAAAGGTGCTATAACTATCGCAACAAGAGAAAAGTTGGATAATTTGGTATTCGTCATTAATTGCAACTTGCAAAGATTAGACGGTCCTGTTACTGGTAACGGTAAAATTATAAACGAATTGGAAGGTATCTTTGAAGGTGCTGGTTGGAATGTAATCAAGGTCATGTGGGGTTCTAGATGGGATGAATTGTTAAGAAAAGACACTTCTGGTAAATTGATCCAATTGATGAACGAAACAGTCGATGGTGACTATCAAACCTTTAAATCAAAGGATGGTGCATACGTTAGAGAACATTTCTTTGGTAAATATCCAGAAACCGCCGCTTTAGTAGCTGATTGGACTGACGAACAAATCTGGGCATTGAATAGAGGTGGTCATGATCCAAAGAAAATATATGCAGCCTTTAAAAAGGCTCAAGAAACCAAGGGTAAAGCTACTGTTATATTAGCACACACAATCAAAGGTTACGGTATGGGTGACGCTGCAGAAGGTAAAAATATCGCACATCAAGTCAAAAAGATGAACATGGATGGTGTTAGACACATCAGAGACAGATTCAATGTTCCAGTATCCGATGCTGACATCGAAAAAATTGCCATACATCACATTTCCTGAAGGTAGTGAAGAACATACCTACTTGCACGCACAAAGACAAAAATTGCATGGTTATTTGCCATCTAGACAACCTAACTTTACTGAAAAGTTGGAATTACCATCATTGCAAGATTTCGGTGCTTTGTTGGAAGAACAATCTAAGGAAATCTCAACTACAATTGCCTTTGTAAGAGCTTTGAACGTCATGTTGAAAAATAAGTCCATTAAGGATAGATTGGTTCCTATCATTGCCGACGAAGCTAGAACTTTTGGTATGGAAGGTTTGTTCAGACAAATTGGTATATACAGTCCAAATGGTCAACAATATACACCTCAAGATAGAGAACAAGTTGCCTATTACAAAGAAGACGAAAGGGTCAAATATTGCAAGAAGGTATAAACGAATTAGGTGCAGGTTGTTCCTGGTTGGCCGCTGCAACTTCTTACTCAACAAACAACTTACCAATGATCCCTTTCTCATATCTATTACAGTATGTTCGGTTTCCAAAGAATTGGTGACTTGTGCTGGGCCGCTGGTTGACCAACAAGCTAGAGGTTTCTTGATAGGTGGTACATCTGGTAGAACCACTTTGAATGGTAAGGTTTACAACATGAAGATGGTCATTCCCACATTCAAAGTTTGACCATTCCAAACTGTATATCATATGATCCTGCTTACGCATATGAAGTCGCTGTTATAATGCATGACGGTTTAGAAAGAATGTACGGTGAAAAGCAAGAAACGTTTACTACTACATCACAACCTTGAATGAAAACTATCCACATGCCAGCCATGCCTGAAGGTGCTGAAGAAGGTATCAGAAAAGGTATCTATAAGTTAGAAACAATCGAAGGTTCCAAGGGTAAAGTTCAATTGTTAGGTTCCGGTAGTATTTAAGCATGTTAGAGAAGCAGCCGAAATATTGGCTAAAGATTACGGTGTTGGTTCTGACGTTTATTCCGTAACCAGTTTCACTGAATTAGCAAGAGATGGTCAAGACTGCGAAAGATGGAATATGTTGCACCCATTAGAAAC | 63 |

TABLE 2-continued

Codon optimized gene sequences (start and stop codons are underlined)

|  |  |  |
|---|---|---|
|  | TCCAAGAGTTCCTTACATTGCTCAAGTAATGAACGATGCCCCTG<br>CTGTTGCATCTACTGACTATATGAAATTGTTTGCCGAACAAGTC<br>AGAACATACGTTCCAGCTGATGACTATAGAGTCTTAGGTACCG<br>ATGGTTTCGGTAGATCTGACTCAAGAGAAAATTTGAGACATCA<br>CTTTGAAGTTGATGCATCATATGTTGTAGTCGCTGCATTGGGTG<br>AATTAGCCAAGAGAGGTGAAATTGATAAAAAGGTTGTAGCCGA<br>CGCAATAGCAAAGTTCAACATAGACGCTGACAAGGTAAACCCT<br>AGATTAGCC<u>TGA</u><br>GAGCTCTTAATTAACAATTCTTCGCCAGAGGAATTC |  |
| aceF | GAATTCGCATAGCAATCTAATCTAAGTTTTAATTACAAGCGGCC<br>GCAAACA<br><u>ATG</u>GCAATAGAAATCAAAGTTCCAGACATAGGTGCAGACGAAG<br>TAGAAATAACAGAAATCTTAGTCAAAGTTGGTGACAAGGTAGA<br>AGCTGAACAATCTTTGATTACTGTTGAAGGTGACAAAGCATCCA<br>TGGAAGTTCCAAGTCCTCAAGCTGGTATAGTAAAGGAAATTAA<br>AGTTTCTGTAGGTGACAAGACCCAAACTGGTGCCTTAATCATGA<br>TTTTTGATTCAGCTGACGGTGCTGCAGACGCCGCTCCAGCACAA<br>GCCGAAGAAAGAAAGAAGCAGCCCCAGCTGCAGCCCCTGCTG<br>CAGCCGCTGCAAAAGATGTCAATGTTCCTGATATCGGTTCAGAC<br>GAAGTAGAAGTCACTGAAATTTTGGTTAAAGTAGGTGACAAGG<br>TAGAAGCAGAACAATCTTTAATTACAGTCGAAGGTGACAAAGC<br>ATCTATGGAAGTCCCAGCCCCTTTTGCTGGTACAGTTAAAGAAA<br>TCAAGGTCAATGTTGGTGACAAGGTTTCTACCGGTTCATTGATT<br>ATGGTTTTCGAAGTAGCAGGTGAAGCAGGTGCCGCTGCACCAG<br>CCGCTAAACAAGAAGCTGCCCCTGCTGCAGCCCCAGCTCCTGCT<br>GCAGGTGTTAAGGAAGTAAACGTCCCAGATATTGGTGGTGACG<br>AAGTTGAAGTAACCGAAGTCATGGTCAAGGTAGGTGACAAGGT<br>TGCCGCTGAACAATCCTTAATTACTGTAGAAGGTGACAAAGCT<br>AGTATGGAAGTTCCAGCTCCTTTTGCAGGTGTTGTAAAAGAATT<br>GAAGGTCAACGTTGGTGACAAAGTTAAGACTGGTTCCTTAATA<br>ATGATCTTCGAAGTTGAAGGTGCTGCCCCAGCTGCAGCCCCTGC<br>AAAAACAAGAAGCTGCAGCCCCAGCTCCTGCTGCGAAGGCTGAA<br>GCACCAGCCGCTGCACCTGCCGCTAAAGCTGAGGGTAAATCTG<br>AATTTGCCGAAAATGATGCTTATGTTCATGCAACACCATTGATT<br>AGAAGATTAGCAAGAGAATTTGGTGTTAACTTGGCTAAAGTAA<br>AGGGTACCGGTAGAAAGGGTAGAATTTTAAGAAGATGTCCA<br>AGCATATGTTAAAGAAGCCATAAAGAGAGCTGAAGCTGCCCCA<br>GCTGCTACAGGTGGTGGTATACCTGGCATGTTGCCATGGCCTAA<br>AGTTGACTTTTCTAAGTTCGGTGAAATTGAAGAAGTTGAATTGG<br>GTAGAATACAAAAGATTTCTGGTGCAAATTTGTCAAGAAACTG<br>GGTCATGATACCACATGTTACTCACTTTGATAAAACAGACATCA<br>CCGAATTGGAAGCCTTTAGAAAACAACAAAATGAAGAAGCCGC<br>TAAGAGAAAGTTAGATGTTAAGATCACACCAGTCGTTTTTATTA<br>TGAAGGCAGTTGCAGCCGCTTTGGAACAAATGCCTAGATTCAA<br>CTCTTCATTATCTGAAGACGGTCAAAGATTGACCTTGAAGAAAT<br>ACATCAACATCGGTGTAGCTGTCGATACTCCAAACGGTTTGGTA<br>GTCCCTGTTTTTAAAGACGTCAATAAGAAAGGTATCATCGAATT<br>GTCCAGAGAATTAATGACAATCAGTAAAAAGGCTAGAGATGGT<br>AAAATTAACTGCAGGTGAAATGCAAGGTGGTTGTTTTACAATATC<br>CAGTATCGGTGGTTTGGGTACTACACATTTCGCACCAATAGTAA<br>ATGCACCTGAAGTCGCCATCTTAGGTGTTTCTAAATCAGCTATG<br>GAACCAGTATGGAACGGTAAAGAATTTGTCCCAAGATTGATGT<br>TGCCTATTTCCTTAAGTTTCGATCACAGAGTTATAGATGGTGCT<br>GACGGTGCCAGATTCATCACCATCATCAACAACACTTTATCCGA<br>TATTAGAAGATTAGTCATG<u>TAA</u><br>GAGCTCTTAATTAACAATTCTTCGCCAGAGGAATTC | 64 |
| lpd | GAATTCATTATCTACTTTTTACAACAAATATAAAACAAGGATCC<br>AAAACA<br><u>ATG</u>TCAACAGAAATCAAGACTCAAGTCGTAGTATTAGGTGCCG<br>GTCCAGCAGGTTACTCCGCAGCATTCAGATGTGCAGACTTAGGT<br>TTGGAAACAGTAATAGTCGAAAGATACAACACCTTGGGTGGTG<br>TTTGTTTAAACGTAGGTTGCATCCCATCTAAAGCATTGTTACAT<br>GTTGCCAAGGTAATTGAAGAAGCCAAAGCATTGGCAGAACACG<br>GTATAGTTTTTGGTGAACCTAAGACCGATATCGACAAGATCAG<br>AACTTGGAAGGAAAAGGTTATTAATCAATTGACTGGTGGTTTA<br>GCTGGTATGGCAAAGGGTAGAAAAGTTAAGGTTGTAAACGGTT<br>TGGGTAAATTCACAGGTGCAAATACCTTAGAAGTCGAAGGTGA<br>AAACGGTAAAACAGTTATAAATTTCGATAACGCTATTATAGCTG<br>CAGGTTCCAGACCAATCCAATTGCCATTCATTCCTCATGAAGAT<br>CCTAGAATTTGGGATAGTACAGACGCTTTGGAATTAAAGGAAG<br>TACCAGAAAGATTGTTAGTCATGGGTGGTGGTATCATTGGTTTG<br>GAAATGGGTACCGTTTACCACGCTTTAGGTTCCCAAATTGATGT<br>CGTTGAAATGTTTGACCAAGTTATACCTGCCGCTGATAAAGACA<br>TCGTTAAGGTTTTTACTAAGAGAATAAGTAAAAAGTTCAATTTG<br>ATGTTAGAAACCAAGGTCACTGCCGTTGAAGCTAAAGAAGATG<br>GTATCTATGTTACAATGGAAGGTAAAAAGGCCCCAGCTGAACC | 65 |

TABLE 2-continued

Codon optimized gene sequences (start and stop codons are underlined)

| | | |
|---|---|---|
| | TCAAAGATACGATGCTGTCTTGGTTGCAATCGGTAGAGTTCCAA<br>ATGGTAAAAATTTGGACGCTGGTAAAGCCGGTGTAGAAGTCGA<br>TGACAGAGGTTTTATTAGAGTAGATAAGCAATTGAGAACTAAC<br>GTCCCACATATTTTCGCAATAGGTGACATCGTTGGTCAACCTAT<br>GTTAGCCCACAAAGGTGTACATGAAGGTCACGTCGCAGCCGAA<br>GTTATTGCTGGTAAAAAGCATTACTTCGATCCAAAGGTTATTCC<br>TTCTATAGCTTACACTGAACCAGAAGTAGCATGGGTCGGTTTGA<br>CAGAAAAGAAGCCAAAGAAAGGGTATTTCATATGAAACTGC<br>TACATTTCCTTGGGCTGCATCTGGTAGAGCAATCGCCTCAGATT<br>GTGCTGACGGTATGACCAAGTTAATCTTCGATAAGGAATCTCAT<br>AGAGTTATCGGTGGTGCAATTGTAGGTACTAATGGTGGTGAATT<br>GTTAGGTGAAATAGGTTTGGCTATCGAAATGGGTTGCGATGCC<br>GAAGACATTGCTTTAACTATACATGCACACCCAACATTGCATGA<br>ATCAGTTGGTTTAGCTGCTGAAGTATTTGAAGGTAGTATAACCG<br>ATTTGCCTAACCCTAAAGCCAAGAAGAAG<u>TAG</u><br>GTCGACATGGAACAGAAGTTGATTTCCGAAGGAATTC | |
| lplA | GAATTCATTATCTACTTTTTACAACAAATATAAAACAAGGATCC<br>AAAACA<br><u>ATG</u>TCCACCTTGAGATTATTGATTAGTGACTCCTATGACCCATG<br>GTTCAACTTAGCCGTCGAAGAATGTATCTTCAGACAAATGCCAG<br>CTACCCAAAGAGTTTATTTTTGTGGAGAAATGCAGATACAGTT<br>GTAATTGGTAGAGCCCAAAATCCATGGAAGGAATGTAACACTA<br>GAAGAATGGAAGAAGACAATGTTAGATTGGCTAGAAGATCTTC<br>AGGTGGTGGTGCAGTATTCCATGATTTGGGTAACACTTGCTTTA<br>CATTCATGGCTGGTAAACCTGAATATGACAAGACCATCTCTACT<br>TCAATAGTATTGAACGCCTTGAACGCTTTAGGTGTCTCCGCCGA<br>AGCTAGTGGTAGAAATGATTTGGTCGTTAAGACTGTTGAAGGT<br>GACAGAAAAGTATCCGGTAGTGCATATAGAGAAACCAAGGATA<br>GAGGTTTTCATCACGGTACTTTGTTATTGAATGCCGATTTGTCC<br>AGATTAGCTAACTACTTGAACCCAGACAAAAAGAAATTAGCTG<br>CAAAGGGTATCACATCTGTAAGATCAAGAGTCACAAACTTGAC<br>CGAATTATTGCCTGGTATAACACATGAACAAGTTTGTGAAGCTA<br>TCACCGAAGCATTTTCGCCCACTATGGTGAAAGAGTTGAAGCA<br>GAAATCATCTCCAAATAAGACTCCAGATTTGCCTAACTTTGC<br>TGAAACATTCGCAAGACAATCCAGTTGGGAATGGAATTTTGGT<br>CAAGCACCTGCCTTCTCACATTTGTTGGATGAAAGATTCACTTG<br>GGGTGGTGTCGAATTGCATTTCGACGTTGAAAAAGGTCACATA<br>ACTAGAGCACAAGTTTTTACAGATTCTTTGAACCCAGCCCCTTT<br>GGAAGCATTGGCAGGTAGATTGCAAGGTTGTTTATACAGAGCC<br>GATATGTTACAACAAGAATGCGAAGCATTGTTGGTTGACTTCCC<br>TGAACAAGAAAGGAATTGAGAGAATTGAGTGCCTGGATGGCT<br>GGTGCTGTAAGA<u>TAG</u><br>CTCGAGTAAGCTTGGTACCGCGGCTAGCTAAGAATTC | 66 |
| aceE$_{av}$ | ATAAGAAT*GCGGCCGC*<u>ATG</u>GAACAAGACATGCAAGACATGCAA<br>GACTTGGACCCAATCGAAACTCAAGAATGGTTGGACTCTTTGG<br>AATCTGTTTTGGACCACGAAGGTGAAGAAAGAGCTCACTACTT<br>GTTGACTAGAATGGGTGAATTGGCTACTAGAACTGGTACTCAAT<br>TGCCATACGCTATCACTACTCCATACAGAAACACTATCCCAGTT<br>ACTCACGAAGCTCACATGCCAGGTGACTTGTTCATGGAAAGAA<br>GAATCAGATCTTTGGTTAGATGAACGCTTTGGCTACTGTTATG<br>AGAGCTAACAAGAAGGACCCAGACTTGGGTGGTCACATCTCTA<br>CTTTCGCTTCTTCTGCTACTTTGTACGACATCGGTTTCAACTACT<br>TCTTCCAAGCTCCAACTGCTGAACACGGTGGTGACTTGATCTAC<br>TTCCAAGGTCACGCTGCGCCAGGTGTATACGCAAGAGCTTTCTT<br>GGAAGGTAGAATCTCTGAAGCTCAATTGCAACAATTCAGACAA<br>GAAGTTGACGGTGACGGTTTGTCTTCTTACCCACACCCACACTT<br>GATGCCAGACTTCTGGCAATTCCCAACTGTTTCTATGGGTTTGG<br>GTCCAATCCAAGCTATCTACCAAGCTAGATTCATGAAGTACTTG<br>GAACACAGAGGTTTCATCCCAGCGGGTAAGCAGAAGGTGTGGT<br>GCTTCATGGGCGACGGTGAATGTGACGAACCAGAATCTTTGGG<br>TGCTATCTCTTTGGCTGGTAGAGAAAAGTTGGACAACTTGATCT<br>TCGTTATCAACTGTAACTTGCAAAGATTGGACGGTCCAGTTAGA<br>GGTAACGGTAAGATCATCCAAGAACTCGAGGGTGTGTTCAGAG<br>GGGCTCAATGGAACGTTAACAAGGTTGTTGGGGTAGATTCTG<br>GGACCCATTGTTCGCTAAGGACCACGCTGGTTTGTTGCAACAAA<br>GAATGGACGAAGTTGTTGACGGTGACTACCAAAACTACAAGGC<br>TAAGGACGGTGCTTTCGTTAGAAAGCACTTCTTCGGTGCTAGAC<br>CAGAATTGTTGGAATTGGTTAAGGACATGTCTGACGAAGACAT<br>CTGGAAGTTGAACAGAGGTGGTCACGACCCATACAAGGTTTAC<br>GCTGCTTACCACCAAGCTGTTAACCACCAAGGTCAACCATCTGT<br>TATCTTGGCTAAGACTATCAAGGGTTACGGTACTGGTGCTGGTG<br>AAGCTAAGAACATCGCTCACAACGTTAAGAAGGTTGATGTAGA<br>AAGCTTGAAGTTGTTCCGTGACAAGTTCGACGTTCCATTGAAGG<br>ACGAAGAATTGGAAGACTTGCCATTCTACAGACCAGACGAAAA<br>CTCTCCAGAAATGAAGTACTTGAGATCTAGAAGAGAAGCTTTG<br>GGTGGTTTCGTTCCACAAAGAAGAAGAAAGTCTATCTCTATCCC | 67 |

TABLE 2-continued

Codon optimized gene sequences (start and stop codons are underlined)

|  | | |
|---|---|---|
| | AACTCCACCATTGGACTCTTTGAAGGCTATCTTGGACGGTACTG<br>GTGACAGAGAAATCTCTACTACTATGGCTTTCGTTAGAATCTTG<br>GCTCAATTGGTTAAGGACAAGGAATTGGGTTCTAGAATCGTTCC<br>AATCATCCCAGACGAAGCTAGAACTTTCGGTATGGAAGGTATG<br>TTCAGACAATTGGGTATCTACTCTTCTGTTGGTCAATTGTACGA<br>ACCAGTTGACAAGGACCAAGTTATGTTCTACAGAGAAGACAAG<br>AAGGGTCAAATCTTGGAAGAAGGTATCAACGAAGCTGGTGCTA<br>TGTCTTCTTGGATCTCTGCTGCTACTGCTTACTCTAACCACAACC<br>AACCAATGTTGCCATTCTACGTTTTCTACTCTATGTTCGGTTTCC<br>AAAGAATCGGTGACTTGGCTTGGGCTGCTGGTGACTCGCAAGC<br>GAGAGGCTTCTTGATCGGTGGCACTGCTGGTAGAACTACTTTGA<br>ACGGTGAAGGTTTGCAACACGAAGACGGTCACTCTCACATCTT<br>GGCTTCTACTATCCCAAACTGTAGAACTTACGACCCAACTTACG<br>CTTACGAAATGGCTGTTATCATCAGAGAAGGTATCAGACAAAT<br>GACTGAAGAACAACAAAACGTTTTCTACTACATCACTGCTATGA<br>ACGAAGCTTACACTCAACCAGCTATGCCAGAAGGTGCTGAAGC<br>TGGTATCGTTAAGGGTATGTACTTGTTGGAAGAAGACAAGAGA<br>GACGCTGCTCACCACGTTCAATTGTTGGGTTCTGGTACTATCTT<br>GAGAGAAGTTAGAGAAGCTGCTAAGATCTTGAGAGAAGACTAC<br>AACGTTGCTGCTGACGTTTGGTCTGTTACTTCTTTCAACGAATTG<br>AGAAGAAACGGTTTGGCTGTTAAAGAAGAAACAGATTGCACC<br>CAGAACAAAAGCCAGAACAATCTTACGTTGAACATGTTTGAA<br>CGGTAGAAAGGGTCCAGTTGTTGCTTCTACTGACTACATGAAGT<br>TGTTCGCTGACCAAATCAGACAATGGGTTCCATCTAGAGAATAC<br>AAGGTTTTGGGTACTGACGGTTTCGGTAGATCTGACACTAGAAA<br>GAAGTTGAGACACTTCTTCGAAGTTGACAGATACTGGGTTGTTT<br>TGGCTGCTCTCGAGGCTCTCGCTGACAGAGGCGACATCGAAGC<br>TAAGGTTGTTGCTGAAGCTATCGCTAAGTTCGGTATCGACCCAG<br>ACAAGAGAAACCCATTGGACTGTTAAT<u>TAA</u>*TTAAGG* | |
| aceF$_{av}$ | ATAAGAAT*GCGGCCGC*<u>ATG</u>TCTGAAATCATCAGAGTTCCAGAC<br>ATCGGTGGTGACGGTGAAGTTATCGAATTGTTGGTTAAGACTGG<br>TGACTTGATCGAAGTAGAGCAAGGCTTGGTTGTTTTGGAGTCTG<br>CTAAGGCTTCTATGGAAGTTCCATCTCCAAAGGCTGGTGTTGTT<br>AAGTCTGTTTCTGTTAAGTTGGGTGACAAGTTGAAGGAAGGTG<br>ACGCTATCATCGAATTGGAACCAGCTGCTGGTGCTGCTGCTGCT<br>CCAGCTGAAGCTGCTGCTGTTCCAGCTGCTCCAACTCAAGCTGT<br>TGACGAAGCTGAAGCTCCATCTCCAGGTGCTTCTGCTACTCCAG<br>CTCCAGCTGCTGCTTCTCAAGAAGTTAGAGTTCCAGACATCGGT<br>TCTGCTGGTAAGGCTAGAGTTATCGAAGTTTTGGTTAAGGCTGG<br>TGACCAAGTTCAAGCGGAGCAGTCGTTGATCGTGCTAGAGTCT<br>GACAAGGCTTCTATGGAAATCCCATCTCCAGCTTCTGGTGTTGT<br>TGAATCTGTTGCTATCCAATTGAACGCTGAAGTTGGTACTGGTG<br>ACTTGATCTTGACTTTGAGAACTACTGGTGCTCAAGCTCAACCA<br>ACTGCTCCAGCTGCTGCTGCTGCTGCTTCTCCAGCTCCAGCTCC<br>ATTGGCTCCAGCTGCTGCTGGTCCACAAGAAGTTAAGGTTCCAG<br>ACATCGGTTCTGCTGGTAAGGCTAGAGTTATCGAAGTTTTGGTT<br>AAGGCTGGTGACCAAGTTCAAGCGGAGCAGTCGTTGATCGTGC<br>TAGAGTCTGACAAGGCTTCTATGGAAATCCCATCTCCAGCTGCT<br>GGTGTTGTTGAATCTGTTGCTGTTCAATTGAACGCTGAAGTTGG<br>TACTGGTGACCAAATCTTGACTTTGAGAGTTGCTGGTGCTGCTC<br>CAGCTGCTGCTCCAGCTCCAGCTGCTGCTCCAGCTAAGCCAGCT<br>GCTGCTCCAGCTGCTGCTGCTCCAGCTCCAGCTCCAGTTGGTGC<br>TCCATCTAGAAACGGTGCTAAGGTTCACGCTGGTCCAGCTGTTA<br>GACAATTGGCTAGAGAATTCGGTGTTGAATTGGCTGCTATCAAC<br>TCTACTGGTCCAAGAGGTAGAATCTTGAAGGAAGACGTTCAAG<br>CTTACGTTAAGGCTATGATGCAAAAGGCTAAGGAAGCTCCAGC<br>TGCTGGTGCTGCTTCTGGTGCTGGTATCCCACCAATCCCACCAG<br>TTGACTTCGCTAAGTACGGTGAAATCGAAGAAGTTCCAATGACT<br>AGATTGATGCAAATCGGTGCTACTAACTTGCACAGATCTTGGTT<br>GAACGTTCCACACGTTACTCAATTCGAATCTGCTGACATCACTG<br>AATTGGAAGCTTTCAGAGTTGCTCAAAAGGCTGTTGCTGAAAA<br>GGCTGGTGTTAAGTTGACTGTTTTGCCATTGTTGTTGAAGGCTT<br>GTGCTTACTTGTTGAAGGAATTGCCAGACTTCAACTCTTCTTTG<br>GCTCCATCTGGTCAAGCTTTGATCAGAAAGAAGTACGTTCACAT<br>CGGTTTCGCTGTTGACACTCCAGACGGTTTGTTGGTTCCAGTTA<br>TCAGAAACGTTGACCAAAAGTCTTTGTTGCAATTGGCTGCTGAA<br>GCTGCTGAATTGGCTGAAAAGGCTAGATCTAAGAAGTTGGGTG<br>CTGACGCTATGCAAGGCGCGTGCTTCACCATCTCTTCTTTGGGT<br>CACATCGGCGGCACTGCGTTCACTCCAATCGTTAACGCTCCAGA<br>AGTTGCTATCTTGGGTGTTTCTAAGGCTTCTATGCAACCAGTTT<br>GGGACGGTAAGGCTTTCCAACCAAGATTGATGTTGCCATTGTCT<br>TTGTCTTACGACCACACAGAGTTATCAACGGTGCTGCTGCTGTAG<br>ATTCACTAAGAGATTGGGTGACTTGTTGGCTGACATCAGAGCTA<br>TCTTGTTG<u>TAA</u>*GAGCTCG* | 68 |
| lpdA$_{av}$ | CG*GGATCC*<u>ATG</u>TCTCAAAAGTTCGACGTTATCGTTATCGGTGCT<br>GGTCCAGGTGGTTACGTTGCTGCTATCAAGTCTGCTCAATTGGG | 69 |

TABLE 2-continued

Codon optimized gene sequences (start and stop codons are underlined)

| | | |
|---|---|---|
| | TTTGAAGACTGCTTTGATCGAAAAGTACAAGGGTAAGGAAGGT<br>AAGACTGCTTTGGGTGGTACTTGTTTGAACGTTGGTTGTATCCC<br>ATCTAAGGCTTTGTTGGACTCTTCTTACAAGTTCCACGAAGCTC<br>ACGAATCTTTCAAGTTGCACGGTATCTCTACTGGTGAAGTTGCT<br>ATCGACGTTCCAACTATGATCGCTAGAAAGGACCAAATCGTTA<br>GAAACTTGACTGGTGGTGTTGCTTCTTTGATCAAGGCTAACGGT<br>GTTACTTTGTTCGAAGGTCACGGTAAGTTGTTGGCTGGTAAGAA<br>GGTTGAAGTTACTGCTGCTGACGGTTCTTCTCAAGTTTTGGACA<br>CTGAAAACGTTATCTTGGCTTCTGGTTCTAAGCCAGTTGAAATC<br>CCACCAGCTCCAGTTGACCAAGACGTTATCGTTGACTCTACTGG<br>TGCTTTGGACTTCCAAAACGTTCCAGGTAAGTTGGGTGTTATCG<br>GTGCTGGTGTTATCGGTTTGGAATTGGGTTCTGTTTGGGCTAGA<br>TTGGGTGCTGAAGTTACTGTTTTGGAAGCTATGGACAAGTTCTT<br>GCCAGCTGTTGACGAACAAGTTGCTAAGGAAGCTCAAAAGATC<br>CTCACTAAGCAAGGTCTCAAGATCTTGCTCGGTGCTAGAGTTAC<br>TGGTACTGAAGTTAAGAACAAGCAAGTTACTGTTAAGTTCGTTG<br>ACGCTGAAGGTGAAAAGTCTCAAGTTTCGACAAGTTGATCGTT<br>GCTGTTGGTAGAAGACCAGTTACTACTGACTTGTTGGCTGCTGA<br>CTCTGGTGTTACTTTGGACGAAAGAGGTTTCATCTACGTTGACG<br>ACTACTGTGCTACTTCTGTTCCAGGTGTTTACGCTATCGGTGAC<br>GTTGTTAGAGGTGCTATGTTGGCTCACAAGGCTTCTGAAGAAGG<br>TGTTGTTGTTGCTGAAAGAATCGCTGGTCACAAGGCTCAAATGA<br>ACTACGACTTGATCCCAGCTGTTATCTACACTCACCCAGAAATC<br>GCTGGTGTTGGTAAGACTGAACAAGCTTTGAAGGCTGAAGGTG<br>TTGCTATCAACGTTGGTGTTTTCCCATTCGCTGCTTCTGGTAGAG<br>CTATGGCTGCTAACGACACTGCTGGTTTCGTTAAGGTTATCGCT<br>GACGCTAAGACTGACAGAGTTTTGGGTGTTCACGTTATCGGTCC<br>ATCTGCTGCTGAATTGGTTCAACAAGGTGCTATCGCTATGGAAT<br>CGGTACTTCTGCTGAAGACTTGGGTATGATGGTTTTCGCTCAC<br>CCAGCTTTGTCGGAGGCTCTCCATGAGGCTGCGCTCGCTGTTTC<br>TGGCCACGCTATCCACGTTGCTAACAGAAAGAAG<u>TAA</u>GTCGAC<br>GTCGG | |
| pdhA | CG<i>GAGCTC</i><u>ATG</u>GCTAAGGCTAAGAAGCAAAAGCCAATCGACTTC<br>AAGGAATTGATGGCTAAGGTTGACGCTGACTTCCCAACTTTCCA<br>AATCTTGGACCAAGACGGTAAGATCGTTAACGAAGACTTGGTT<br>CCAGACTTGTCTGACGAAGAATTGGTTGAATTGATGACTAGAAT<br>GGTTTGGTCTAGAGTTTTGGACCAAAGATCTACTGCTTTGAACA<br>GACAAGGTAGATTGGGTTTCTTCGCTCCAACTGCTGGTCAAGAA<br>GCTTCTCAATTGGCTTCTCAATTCGCTATGGAAAAGGAAGACTA<br>CTTGTTGCCAGGTTACAGAGACGTTCCACAATTGGTTCAACACG<br>GTTTGCCATTGAGAGAAGCTTTCTTGTGGTCTAGAGGTCACGTT<br>GCTGGTAACTACTACGCTGAAGACTTGAACGCTTTGCCACCACA<br>AATCATCATCGGTGCTCAATACATCCAAGCTGCTGGTGTTGCTT<br>TGGGTTTGAAGAAGAGAGGTAAGGAAAACGTTGTTTTCACTTA<br>CACTGGTGACGGTGGTTCTTCTCAAGGTGACTTCTACGAAGCTA<br>TCAACTTCGCTGGTGCTTACCAAGCTAACGGTGTTTTCATCATC<br>CAAAACAACGGTTTCGCTATCTCTACTCCAAGAGAAAAGCAAA<br>CTGCTGCTAAGACTTTGGCTCAAAAGGCTGTTGCTGCTGGTATC<br>CCAGGTATCCAAGTTGACGGTATGGACCCATTGGCTGTTTACGC<br>TATCGCTAAGGAAGCTAGAGACTGGTCTGCTGCTGGTAACGGT<br>CCAGTTCTCATAGAAACTCTCACTTACAGATACGGTCCACACAC<br>TTTGTCTGGTGACGACCCAACTAGATACAGATCTAAGGAAATG<br>GACGACGAATGGGTTCAAAAGGACCCATTGACTAGATTCAGAA<br>AGTACCTCACTGACAAGGGCTTGTGGTCTGAAGCGAAGGAAGA<br>AGAAATCATCGAAAAGACTAAGGAAGAAATCAAGGTTGCTATC<br>GCTGAAGCTGACAAGGCTCCAAAGCAAAAGGTTTCTGACTTCTT<br>GAAGAACATGTTCGAAGTTCAACCACAAACTATCAAGGAACAA<br>ATCGCTTTCTACGAAGCTAAGGAATCTAAG<u>TAA</u>GCGGCCGCTA<br>AACTAT | 70 |
| pdhB | CG<i>GGATCC</i><u>ATG</u>GCTCAAAAGACTATGATCCAAGCTATCACTGAC<br>GCTTTGGCTTTGGAATTGGAAAAGGACGAAAACGTTTTGATCTT<br>CGGTGAAGACGTTGGTAACAACGGTGGTGTTTTCAGAGCTACT<br>GAAGGTTTGCAAGAAAAGTTCGGTGAAGACAGAGTTTTCGACA<br>CTCCATTGGCTGAATCTGGTATCGGTGGTTTGGCTTTCGGTTTG<br>GCTTTGCAAGGTTACAGACCAGTTCCAGAAATCCAGTTCTTTGG<br>TTTCGTCTTCGAAGTGTTCGACGAAATCGTTGGTCAAATGGCTA<br>GAACTAGATACAGAATGGGTGGTACTAGAAACATGCCAATCAC<br>TGTTAGAGCTCCATTCGGTGGTGGTGTTCACACTCCAGAATTGC<br>ACTCTGACAACTTGGAAGGTTTGATCGCTCAATCTCCAGGTGTT<br>AGAGTTGTTATCCCATCTAACCCATACGACGCTAAGGGTTTGTT<br>GATCTCTTCTATCAGATCTAACGATCCAGTTGTATACCTGGAAC<br>ACATGAAGTTGTACAGATCTTTCAGAGAAGAAGTTCCAGACGA<br>AGCTTACGAAGTTCCATTGGACAAGGCTGCTGTTACTAGAGAA<br>GGTACTGACGTTTCTATCATCACTTACGGTGCTATGGTTAGAGA<br>AGCTATCAAGGCTGCTGACTCTTTGGCTAAGGACAACATCTCTG<br>CTGAAAATCATCGACTTGAGAACTGTTGCTCCATTGGACGTTGAA | 71 |

TABLE 2-continued

Codon optimized gene sequences (start and stop codons are underlined)

|   |   |   |
|---|---|---|
|   | ACTATCATCAACTCTGTTGAAAAGACTGGTAGAGTTGTTGTTGT<br>TCAAGAAGCTCAAAAGCAAGCTGGTGTTGGTGCTATGGTTGTTT<br>CTGAAATCTCTGAGCGTGCTGTGCTATCTTTGGAAGCTCCAATC<br>GGTAGAGTTTCTGCTCCAGACACTATCTTCCCATTCGGTCAAGC<br>TGAAAACATCTGGTTGCCAAACGCTAAGGACATCGAAGCTAAG<br>GCTAGAGAAATCGTTGAATTC<u>TAA</u>CTCGAGCGG |   |
| aceF<sub>ef</sub> | CG<i>GAGCTC</i><u>ATG</u>GCTTACCAATTCAAGTTGCCAGACATCGGTGAAG<br>GTATCGCTGAAGGTGAAATCGTTAAGTGGTTCGTTAAGCCAGGT<br>GACACTATCAACGAAGACGACACTTTGTTGGAAGTTCAAAACG<br>ACAAGTCTGTTGAAGAAATCCCATCTCCAGTTACTGGTACTGTT<br>AAGAACATCGTTGTTCCAGAAGGTACTGTTGCTAACGTAGGCG<br>ACGTGCTAATCGAAATCGACGCTCCAGGTCACGAAGACAACGA<br>CGCTGCTCCAGCTGCTCCAGCTCAAGAACAAACTCCAGCTCAAC<br>CAGCTGCTGTTCCAACTACTGAAGCTGCTGGTGGTTTCTTCCAA<br>TTCAAGTTGCCAGACATCGGTGAAGGTATCGCTGAAGGTGAAA<br>TCGTTAAGTGGTTCGTTAAGGCTGGTGACACTATCAACGAAGAC<br>GACTCTTTGTTGGAAGTTCAAAACGACAAGTCTGTTGAAGAAAT<br>CCCATCTCCAGTTACTGGTACTGTTAAGAACATCGTTGTTCCAG<br>AAGGTACTGTTGCTAACGTAGGCGACGTCCTCGTTGAAATCGAC<br>GCTCCAGGTCACAACTCTGCTGCTCCATCTGTTGCTGCTCCAGC<br>TACTGACGCTCCAAAGGCTGAAGCTTCTGCTCCAGCTGCTTCTA<br>CTGGTGTTGTTGCTGCTGACCCAAACAAGAGAGTTTTGGCT<br>ATGCCATCTGTTAGACAATACGCTAGAGAAAAGGACGTTGACA<br>TCACTCAAGTTACTGCTACTGGTAAGGGTGGTAGAGTTATCAAG<br>GCTGACATCGACGCTTTCGTTTCTGGTGGTTCTCAAGCTGCTCC<br>AGCTACTGAAGCTGCTGCTACTGAAGCTGCTCCAAAGGCTGAA<br>GCTGCTGCTCCAAAGGCTGCTCCAAAGGCTTTCACTTCTGACTT<br>GGGTGAAATGGAAACTAGAGAAAAGATGACTCCAACTAGAAA<br>GGCTATCGCTAAGGCTATGGTTAACTCTAAGCACACTGCTCCAC<br>ACGTTACTTTGCACGATGAAGTTGAAGTAAGCAAGTTGTGGGA<br>CCACAGAAAGAAGTTCAAGGACGTTGCTGCTGCTAACGGTACT<br>AAGTTGACTTTCTTGCCATACGTTGTTAAGGCTTTGACTTCTACT<br>GTTCAAAAGTTCCCAATCTTGAACGCTTCTATCGACGACGCTGC<br>TCAAGAAATCGTTTACAAGAACTACTTCAACATCGGTATCGCTA<br>CTGACACTGACCACGGTTTGTACGTTCCAAACGTTAAGAACGCT<br>AACACTAAGTCTATGTTCGCTATCGCTGACGAAATCAACGAAA<br>AGGCTGCTTTGGCTATCGAAGGTAAGTTGACTGCTCAAGACATG<br>AGAGACGGTACTATCACTATCTCTAACATCGGTTCTGTTGGTGG<br>TGGTTGGTTCACTCCAGTTATCAACTACCCAGAAGTTGCTATCT<br>TGGGTGTTGGTACTATCGCTCAAGAACCAGTTGTTAACGCTGAC<br>GGTGAAATCGTTGTTGGTAGAATGATGAAGTTGTCGCTCAGCTT<br>CGACCACAGAATAGTTGACGGTGCTACTGCTCAAAAGGCTATG<br>AACAACATCAAGAGATTGTTGGCTGACCCAGAATTGTTGTTGAT<br>GGAAGGT<u>TAA</u>GCGGCCGCTAAACTAT | 72 |
| lpdA<sub>ef</sub> | CG<i>GGATCC</i><u>ATG</u>GTTGTTGGTGACTTCGCTATCGAATTGGACACT<br>GTTGTTATCGGTGCTGGTCCAGGTGGTTACGTTGCTGCTATCAG<br>AGCTGCTGAAATGGGTCAAAAGGTTGCTATCATCGAAAGAGAA<br>TACATCGGCGGCGTTTGCCTCAACGTTGGTTGTATCCCATCTAA<br>GGCTTTGATCGCTGCTGGTCACCACTACCAAGAAGCTCAAGACT<br>CTTCTACTTTCGGTGTTACTGCTAAGGGTGTTGAATTGGACTTC<br>GCTAAGACTCAAGACTGGAAGGACAACACTGTTGTTAAGTCTTT<br>GACTGGTGGTGTTGGTATGTTGTTGAAGAAGCACAAGGTTGAA<br>ATCATCGAGGGCGAAGCGTTCTTCGTTGACGAGAACACTTTGA<br>GAGTTATCCACCCAGACTCTGCTCAAACTTACTCTTTCAACAAC<br>GCTATCGTTGCTACTGGTTCTAGACCAATCGAAATCCCCAGGTTT<br>CAAGTTCGGTGGTAGAGTTTTGGACTCGACTGGTGGTCTCAACT<br>TGAAGGAGGTTCCAAAGAAGTTCGTTATCATCGGTGGTGGTGTT<br>ATCGGTGCTGAATTGGGTGGTGCTTACGCTAACTTGGGTTCTGA<br>AGTTACTATCTTGGAAGGTTCTCCATCTATCTTGCCAACTTACG<br>AAAAGGACATGTTAAGGTTGTTACTGACCACTTCAAGAAGAA<br>GAACGTTACTATCGTTACTTCTGCTATGGCTAAGGAAGCTGTTG<br>ACAACGGTGACTCTGTTACTGTTAAGTACGAAGTTAACGGTAA<br>GGAAGAATCTGTTGAAGCTGACTACGTTATGGTTACTGTTGGTA<br>GAAGACCAAACACTGACGACTTGGGTTTGGAACAAGCTGGTGT<br>TGAAATCGGTGAAAGAGGTTTGATCCCAGTTGACAACCAAGGT<br>AGAACTAACGTTAAGAACATCTTCGCTATCGGTGACATCGTTCC<br>AGGTGCTGCTTTGGCTCACAAGGCTTCTTACGAAGCTAAGATCG<br>CTGCTGAAGCTATCTCTGGTAAGAAGGTTGCTGTTGACTACAAG<br>GCTATGCCAGCTGTTGCTTTCACTGACCCAGAATTGGCTTCTGT<br>TGGTATGACTGTTGCTGAAGCTAAGGAAGCTGGTATCGAAGCTC<br>AAGGGTTACAAGTTCCCATTCGCTGGTAACGGTAGAGCTATCTC<br>TTTGGACAAGACTGAAGGTTTCATGAGATTGGTTACTACTGTTG<br>AAGACAACGTTATCATCGGTGCTCAAATCGCTGGTGTTGGTGCT<br>TCTGACATGATCTCTGAATTGGCTTTGGCTATCGAATCTGGTAT<br>GAACGCGGAAGACATCGCTCTCACTATCCACCCACACCCATCTT | 73 |

TABLE 2-continued

Codon optimized gene sequences (start and stop codons are underlined)

|  |  |  |
|---|---|---|
|  | TGGGTGAAATCACTATGGACACTGCTGAATTGGCTTTGGGTTTG<br>CCAATCCACATC<u>TAA</u>GTCGACGTCGG |  |
| acpP | CG<i>GGATCC</i><u>ATG</u>AGCACTATCGAAGAACGCGTTAAGAAAATTAT<br>CGGCGAACAGCTGGGCGTTAAGCAGGAAGAAGTTACCAACAAT<br>GCTTCTTTCGTTGAAGACCTGGGCGCGGATTCTCTTGACACCGT<br>TGAGCTGGTAATGGCTCTGGAAGAAGAGTTTGATACTGAGATT<br>CCGGACGAAGAAGCTGAGAAAATCACCACCGTTCAGGCTGCCA<br>TTGATTACATCAACGGCCACCAGGCG<u>TAA</u>CTCGAGCGG | 74 |
| aasS | ATAAGAAT<i>GCGGCCGC</i><u>ATG</u>AACCAGTATGTAAATGATCCATCC<br>AATTATCAGTTACTAATTAAAAACTTGCTGTTTTCCCCAGTTGCT<br>TTCAACCCAGAGCAAGAAATCGTCTACGCTAACCACCGCCGTC<br>ATAGCTACAAAACGTTTCATGATCGTGTAAGACAGTTTGCCAAC<br>GCGCTTACCAAAATGGGCGTGAAAAAGGCGATACGGTTGCTG<br>TGATGGATTACGACTCCCACCGTTACCTTGAGTGTTACTTTGCT<br>ATCCCAATGATTGGTGCCAAGCTGCACATGATTAACGTTCGTTT<br>GTCTCCAGAACAGATCCTTTACACCATTGATCATGCCGAAGATG<br>ACATCATTCTTATTCATGAAGAGTTTCTACCAATCTTAGACCAG<br>ATCAAAGGACGCATTGATACGGTCACTCGCTACGTTGTGTTACG<br>TGATGATGAAGAGTGTGAGTATGAACGCCTTCTTGAACAGGAA<br>AGCACGGAATACAATTTCCCAGATTTCGATGAAAACACGGTGG<br>CGACAACTTTCTACACCACGGGTACTACAGGATTTCCAAAAGG<br>CGTTTTCTTCACGCATCGTCAACTTGTTCTTCATACTATGGGTAT<br>ATTAAGCACAATCGGTACCAACGCTTCACAAGGTCGATTGCATC<br>AAGGTGACATCTACATGCCGATTACGCCGATGTTTCATGTCCAT<br>GCTTGGGGGCTTCCATATATGGCAACCATGCTTGGTGTTAAGCA<br>AGTCTACCCGGGTAAGTATGTTCCAGATGTTTTGCTTAACCTGA<br>TTGAGCAAGAGAAGGTGACGTTCTCACACTGTGTGCCGACTATT<br>TTGCATCTACTTCTGAGCTCTCCAAAGTCGAAGGCGATGGACTT<br>TTCTGGGTGGAAAGTCGTCATTGGTGGTGCTGCGCTACCAAAAG<br>CATTATGTAAATCAGCTCTAGAACGTGATATCGACGTATTTGCT<br>GGTTACGGCATGAGTGAGACTGGACCTATTCTTTCTATCGTCCA<br>ATTGACGCCTGAGCAATTAGAGTTAGATGTCGACCAACAAGCG<br>GAATATCGCTCGAAGACAGGTAAGAAAGTTGCGCTTGTAGAAG<br>CGTATATTGTGGATGAGGATATGAACAAACTGCCTCATGATGG<br>CGAAACCGCTGGTGAAATTGTTGTTCGTGCACCTTGGTTAACAC<br>CTAACTACTACAAAGACAACAAAAACTCTAAAGCACTATGGCG<br>TGGCGGTTACCTGCACACAGGTGATGTGGCGCATATTGATGAC<br>GAAGGCTTTATCAAGATCACTGACCGCGTAAAAGATATGATTA<br>AGATATCTGGTGAGTGGGTAAGCTCTTTAGAGCTTGAAGACATT<br>CTCCACCAGCATCAGAGTGTTTCCGAAGTTGCGGTGATTGGTAT<br>GCCGCACAACAAGTGGGGTGAAGTGCCGTTAGCTTTGGTGACA<br>TTGAAAGAAGACGCTCAAGTCACAGAAAAGGAACTGTTAGGTT<br>TTGCGAAAGACTTCATCAATAAAGGGATTCTTGCTAGAGAAGC<br>ATTACTACTTAAAGTGAAGATAGTGGACGAGATTGCTAAGACC<br>AGCGTTGGTAAAGTGGATAAGAAAGAACTGCGTAAACTTCATC<br>TG<u>TAA</u>TTAATTAAGG | 75 |
| Pfor | GTCGCTTATGCTATGTCTGAAGTCGCCGCTATCTATCCTATTACC<br>CCATCTTCAACTATGGGTGAAGAAGCAGATGACTGGGCTGCAC<br>AAGGTAGAAAGAATATTTTTGGTCAAACCTTGACTATAAGAGA<br>AATGCAATCAGAAGCTGGTGCCGCTGGTGCTGTTCATGGTGCAT<br>TAGCAGCCGGTGCTTTGACTACAACCTTCACTGCATCCCAAGGT<br>TTGTTGTTGATGATCCCAAACATGTACAAAATTAGTGGTGAATT<br>ATTGCCTGGTGTATTTCACGTTACCGCTAGAGCAATCGCTGCAC<br>ATGCATTGTCTATTTTCGGTGACCACCAAGACATATATGCCGCT<br>AGACAAACAGGTTTTGCAATGTTAGCCTCCAGTTCTGTACAAGA<br>AGCTCATGATATGGCTTTAGTTGCACACTTGGCAGCCATTGAAT<br>CTAACGTTCCTTTTATGCATTTCTTTGATGGTTTCAGAACATCAC<br>ACGAAATACAAAAGATTGAAGTCTTAGATTACGCCGACATGGC<br>TTCCTTAGTAAATCAAAAAGCCTTGGCTGAGTTTAGAGCAAAG<br>AGTATGAATCCAGAACATCCTCACGTTAGAGGTACTGCTCAAA<br>ACCCAGATATATACTTTCAAGGTAGAGAAGCTGCAAATCCTTAT<br>TACTTGAAAGTACCAGGTATCGTTGCCGAATACATGCAAAAGG<br>TAGCTTCTTTAACAGGTAGATCATACAAGTTGTTTGATTATGTT<br>GGTGCACCTGACGCCGAAAGAGTAATTGTTTCAATGGGTTCATC<br>CTGTGAAACTATCGAAGAAGTTATTAATCATTTGGCCGCTAAGG<br>GTGAAAAGATCGGTTTAATTAAAGTAAGATTGTACAGACCATT<br>CGTTTCTGAAGCATTTTTCGCAGCCTTGCCTGCATCAGCCAAAG<br>TCATTACTGTATTAGATAGAACAAAGGAACCAGGTGCTCCAGG<br>TGACCCATTATATTTGGACGTATGCTCTGCTTTTGTTGAAAGAG<br>GTGAAGCAATGCCAAAAATTTGGCCGGTAGATACGGTTTGGG<br>TTCTAAAGAATTTTCTCCTGCAATGGTTAAGTCTGTCTATGATA<br>ATATGTCAGGTGCTAAAAAGAACCATTTTACAGTTGGTATAGA<br>AGATGACGTCACAGGTACTTCTTTGCCAGTTGATAATGCTTTCG<br>CAGACACTACACCTAAAGGTACTATTCAATGTCAATTTTGGGGT<br>TTAGGTGCAGATGGTACAGTTGGTGCCAATAAGCAAGCTATAA | 76 |

TABLE 2-continued

Codon optimized gene sequences (start and stop codons are underlined)

|  |  |  |
|---|---|---|
|  | AGATTATAGGTGACAACACTGACTTGTTTGCTCAAGGTTACTTC<br>TCTTATGATTCCAAAAAGAGTGGTGGTATCACCATTTCTCATTT<br>GAGATTCGGTGAAAAGCCAATCCAATCAACTTACTTAGTAAAC<br>AGAGCAGATTACGTTGCCTGTCACAACCCTGCTTACGTCGGTAT<br>CTATGATATTTTGGAAGGTATCAAGGACGGTGGTACATTCGTTT<br>TAAATTCTCCTTGGTCTTCTTTGGAAGATATGGACAAACATTTG<br>CCTTCAGGTATAAAGAGAACCATCGCTAATAAGAAATTGAAGT<br>CTACAACATCGATGCTGTCAAGATCGCAACAGACGTAGGTTTA<br>GGTGGTAGAATTAACATGATCATGCAAACCGCATTTTTCAAATT<br>GGCCGGTGTCTTGCCATTCGAAAAGGCAGTTGATTTGTTGAAAA<br>AGTCTATACACAAAGCCTACGGTAAAAGGGTGAAAAGATTGT<br>TAAGATGAATACCGATGCCGTTGATCAAGCTGTAACTTCCTTAC<br>AAGAGTTTAAATATCCTGATAGTTGGAAGGACGCCCCAGCTGA<br>AACCAAGGCTGAACCTATGACTAATGAATTTTTCAAGAACGTTG<br>TCAAGCCAATATTGACTCAACAAGGTGACAAATTGCCTGTTTCT<br>GCTTTTGAAGCAGACGGTAGATTCCCATTGGGTACATCACAATT<br>CGAAAAGAGAGGTGTTGCAATCAACGTCCCTCAATGGGTTCCA<br>GAAAATTGTATTCAATGCAACCAATGTGCTTTTGTTTGTCCTCA<br>TTCTGCTATTTTACCAGTTTTGGCAAAAGAAGAAGAATTAGTCG<br>GTGCACCAGCCAATTTCACAGCCTTGGAAGCTAAGGGTAAAGA<br>ATTAAAGGGTTACAAGTTTAGAATACAAATCAATACCTTGGATT<br>GCATGGGTTGTGGTAACTGCGCTGACATTTGCCCACCTAAAGAA<br>AAGGCATTAGTAATGCAACCATTGGATACTCAAAGAGACGCTC<br>AAGTTCCTAATTTGGAATACGCTGCAAGAATACCAGTTAAATCT<br>GAAGTCTTACCTAGAGATTCCTTGAAGGGTAGTCAATTCCAAGA<br>ACCATTGATGGAATTTTCTGGTGCTTGTTCAGGTTGCGGTGAAA<br>CTCCTTATGTCAGAGTAATTACACAATTGTTCGGTGAAAGAATG<br>TTCATCGCTAATGCAACTGGTTGTTCATCCATTTGGGGTGCCTCT<br>GCTCCTTCAATGCCATACAAAACAAATAGATTGGGTCAAGGTC<br>CAGCTTGGGGTAACTCCTTATTTGAAGATGCCGCTGAATATGGT<br>TTTGGTATGAACATGTCTATGTTCGCCAGAAGAACACATTTGGC<br>TGATTTGGCAGCCAAGGCTTTGGAATCCGATGCAAGTGGTGAC<br>GTTAAAGAAGCATTACAAGGTTGGTTGGCCGGTAAAAATGATC<br>CAATCAAATCTAAGGAATACGGTGACAAATTGAAAAAGTTATT<br>GGCTGGTCAAAAGGATGGTTTATTGGGTCAAATTGCTGCAATGT<br>CTGATTTGTACACTAAAAAGTCAGTTTGGATCTTCGGTGGTGAC<br>GGTTGGGCATACGACATCGGTTATGGTGGTTTAGATCATGTTTT<br>GGCTTCTGGTGAAGATGTTAATGTCTTCGTAATGGACACTGAAG<br>TTTATTCAAACACCGGTGGTCAAAGTTCTAAAGCTACTCCAACA<br>GGTGCAGTTGCCAAATTTGCTGCTGCTGGTAAAAGAACAGGTA<br>AAAAGGATTTGGCAAGAATGGTTATGACTTATGGTTACGTTTAT<br>GTCGCTACTGTTTCTATGGGTTACAGTAAGCAACAATTCTTGAA<br>GGTTTTGAAGGAAGCTGAATCTTTCCCAGGTCCATCTTTGGTTA<br>TTGCTTATGCAACCTGTATCAACCAAGGTTTAAGAAAGGGTATG<br>GGTAAATCCCAAGATGTCATGAATACTGCTGTAAAAAGTGGTT<br>ACTGGCCTTTGTTCAGATATGATCCAAGATTAGCCGCTCAAGGT<br>AAAAACCCATTTCAATTAGATTCCAAGGCACCTGACGGTAGTGT<br>CGAAGAATTTTTGATGGCCCAAAATAGATTCGCTGTATTAGATA<br>GATCATTTCCAGAAGACGCTAAAAGATTGAGAGCACAAGTTGC<br>CCATGAATTGGATGTCAGATTCAAAGAATTAGAACACATGGCA<br>GCCACTAATATTTTTGAATCCTTCGCCCCTGCTGGTGGTAAAGC<br>CGATGGTAGTGTTGACTTTGGTGAAGGTGCTGAATTTTGTACAA<br>GAGATGACACCCCTATGATGGCAAGACCAGATTCAGGTGAAGC<br>CTGCGACCAAACAGAGCAGGTACATCAGAACAACAAGGTGAC<br>TTATCCAAGAGAACCAAGAAATGA |  |
| eutD<br>pta<sup>R252H</sup> | CG*GGGATCC*<u>ATG</u>TCTAGAATAATAATGTTGATCCCTACTGGTACT<br>TCCGTCGGTTTGACCTCCGTATCCTTGGGTGTAATAAGAGCAAT<br>GGAAAGAAAGGGTGTTAGATTATCAGTCTTTAAACCAATCGCT<br>CAACCTAGAGCAGGTGGTGACGCCCCAGACCAAACTACAACCA<br>TTGTTAGAGCTAATTCTACATTACCAGCTGCAGAACCTTTGAAG<br>ATGTCTCATGTTGAATCATTGTTGTCTTCAAACCAAAAGGATGT<br>TTTGATGGAAGAAATCATCGCTAACTACCATGCAAACACTAAA<br>GACGCTGAAGTTGTCTTAGTAGAAGGTTTGGTTCCTACAAGAAA<br>GCACCAATTCGCACAATCTTTGAACTACGAAATAGCAAAACC<br>TTGAACGCCGAAATAGTATTCGTTATGTCACAAGGTACAGATAC<br>CCCAGAACAATTGAACGAAAGAATCGAATTGACTAGATCCAGT<br>TTCGGTGGTGCAAAGAATACTAACATAACAGGTGTTATTATTAA<br>TAAGTTGAACGCTCCAGTTGATGAACAAGGTAGAACTAGACCT<br>GACTTGTCTGAAATATTCGATGACTCTTCAAAGGCTCAAGTTAT<br>TAAGATCGATCCAGCAAAGTTACAAGAATCCAGTCCATTACCT<br>GTCTTGGGTGCTGTACCTTGGTCTTTCGATTTGATTGCCACAAG<br>AGCTATAGACATGGCTAGACATTTGAATGCAACCATAATCAAC<br>GAAGGTGACATAAAGACAAGACACGTCAAATCCGTAACCTTTT<br>GTGCTAGAAGTATCCCACATATGTTGGAACACTTCAGAGCCGGT<br>TCTTTGTTAGTTACATCAGCTGATAGACCTGACGTCTTAGTAGC<br>CGCTTGTTGGCAGCCATGAATGGTGTTGAAATTGGTGCATTGT<br>TATTGACTGGTGGTTATGAAATGGATGCCAGAATATCTAAGTTA</u> | 77 |

TABLE 2-continued

Codon optimized gene sequences (start and stop codons are underlined)

|  |  |  |
|---|---|---|
|  | TGCGAAAGAGCATTTGCCACCGGTTTGCCAGTTTTCATGGTTAA<br>TACTAACACATGGCAAACTTCTTTGTCATTGCAATCTTTAATTT<br>GGAAGTTCCTGTCGATGACCATGAAAGAATCGAAAAGGTTCAA<br>GAATACGTCGCCAATTACGTAAACGCTGAATGGATTGAATCCTT<br>AACCGCAACTTCTGAAAGATCAAGAAGATTGAGTCCACCTGCT<br>TTCAGATACCAATTGACAGAATTGGCAAGAAAGGCCGGTAAAA<br>GAGTAGTTTTACCAGAAGGTGACGAACCTAGAACAGTTAAAGC<br>TGCAGCCATCTGTGCAGAAAGAGGTATTGCCACCTGCGTTTTGT<br>TGGGTAACCCAGATGAAATTAACAGAGTTGCTGCATCACAAGG<br>TGTCGAATTGGGTGCAGGTATCGAAATTGTTGATCCTGAAGTCG<br>TAAGAGAATCTTACGTTGCTAGATTAGTCGAATTGAGAAAATC<br>AAAGGGTATGACTGAACCAGTTGCAAGAGAACAATTGGAAGAT<br>AACGTTGTCTTGGGTACATTAATGTTGGAACAAGATGAAGTAG<br>ACGGTTTAGTTTCTGGTGCTGTCCACACTACAGCAAACACCATA<br>AGACCACCTTTACAATTGATCAAAACTGCTCCAGGTTCTTCATT<br>GGTATCCAGTGTTTTCTTTATGTTGTTGCCTGAACAAGTATACGT<br>TTACGGTGACTGCGCAATTAATCCAGACCCTACAGCCGAACAA<br>TTGGCTGAAATAGCAATCCAATCCGCTGATAGTGCTATCGCATT<br>TGGTATTGAACCAAGAGTTGCAATGTTATCCTATAGTACAGGTA<br>CCTCCGGTGCTGGTAGTGATGTCGAAAAAGTTAGAGAAGCCAC<br>TAGATTGGCTCAAGAAAAGAGACCAGATTTGATGATTGACGGT<br>CCTTTTGCAATACGATGCCGCTGTAATGGCCGACGTTGCTAAATC<br>CAAGGCTCCAAATAGTCCTGTAGCAGGTAGAGCCACTGTTTTTA<br>TTTTCCCAGATTTGAACACTGGTAACACCACTTATAAGGCCGTT<br>CAAAGATCTGCTGACTTAATTTCAATAGGTCCAATGTTGCAGGG<br>TATGAGAAAACCTGTTAACGATTTGTCCAGAGGTGCTTTGGTCG<br>ATGACATAGTATACACCATCGCTTTGACTGCAATTCAAGCCTCT<br>CAACAACAACAAT<u>AAG</u>CTAGCTAG |  |
| pta<sup>G273D</sup> | CG<u>GGATCC</u>A<u>TG</u>TCTAGAATAATAATGTTGATCCCTACTGGTACT<br>TCCGTCGGTTTGACCTCCGTATCCTTGGGTGTAATAAGAGCAAT<br>GGAAAGAAAGGGTGTTAGATTATCAGTCTTTAAACCAATCGCT<br>CAACCTAGAGCAGGTGGTGACGCCCCAGACCAAACTACAACCA<br>TTGTTAGAGCTAATTCTACATTACCAGCTGCAGAACCTTTGAAG<br>ATGTCTCATGTTGAATCATTGTTGTCTTCAAACCAAAAGGATGT<br>TTTGATGGAAGAAATCATCGCTAACTACCATGCAAACACTAAG<br>GACGCTGAAGTTGTCTTAGTAGAAGGTTTGGTTCCTACAAGAAA<br>GCACCAATTCGCACAATCTTTGAACTACGAAATAGCAAAAACC<br>TTGAACGCCGAAATAGTATTCGTTATGTCACAAGGTACAGATAC<br>CCCAGAACAATTGAACGAAAGAATCGAATTGACTAGATCCAGT<br>TTCGGTGGTGCAAAGAATACTAACATAACAGGTGTTATTATTAA<br>TAAGTTGAACGCTCCAGTTGATGAACAAGGTAGAACTAGACCT<br>GACTTGTCTGAAATATTCGATGACTCTTCAAAGGCTCAAGTTAT<br>TAAGATCGATCCAGCAAAGTTACAAGAATCCAGTCCATTACCT<br>GTCTTGGGTGCTGTACCTTGGTCTTTCGATTTGATTGCCACAAG<br>AGCTATAGACATGGCTAGACATTTGAATGCAACCATAATCAAC<br>GAAGGTGACATAAAGACAAGACACGTCAAATCCGTAACCTTTT<br>GTGCTAGAAGTATCCCACATATGTTGGAACACTTCAGAGCCGG<br>ATCTTTGTTAGTTACATCAGCTGATAGACCTGACGTCTTAGTAG<br>CCGCTTGTTTGGCAGCCATGAATGGTGTTGAAATTGGTGCATTG<br>TTATTGACTGGTGGTTATGAAATGGATGCCAGAATATCTAAGTT<br>ATGCGAAAGAGCATTTGCCACCGGTTTGCCAGTTTTCATGGTCA<br>ATACTAACACATGGCAAACTTCTTTGTCATTGCAATCTTTTAATT<br>TGGAAGTTCCTGTCGATGACCATGAAAGAATCGAAAAGGTTCA<br>AGAATACGTCGCCAATTACGTAAACGCTGAATGGATTGAATCC<br>TTAACCGCAACTTCTGAAAGATCAAGAAGATTGAGTCCACCTG<br>CTTTCAGATACCAATTGACAGAATTGGCAAGAAAGGCCGGTAA<br>AAGAGTAGTTTTACCAGAAGGTGACGAACCTAGAACAGTTAAA<br>GCTGCAGCCATCTGTGCAGAAAGAGGTATTGCCACCTGCGTTTT<br>GTTGGGTAACCCAGATGAAATTAACAGAGTTGCTGCATCACAA<br>GGTGTCGAATTGGGTGCAGGTATCGAAATTGTTGATCCTGAAGT<br>CGTAAGAGAATCTTACGTTGCTAGATTAGTCGAATTGAGAAAA<br>TCAAAGGGTATGACTGAACCAGTTGCAAGAGAACAATTGGAAG<br>ATAACGTTGTCTTGGGTACATTAATGTTGGAACAAGATGAAGTA<br>GACGGTTTAGTTTCTGGTGCTGTCCACACTACAGCAAACACCAT<br>AAGACCACCTTTACAATTGATCAAAACTGCTCCAGGTTCTTCAT<br>TGGTATCCAGTGTTTTCTTTATGTTGTTGCCTGAACAAGTATACG<br>TTTACGGTGACTGCGCAATTAATCCAGACCCTACAGCCGAACA<br>ATTGGCTGAAATAGCAATCCAATCCGCTGATAGTGCTATCGCAT<br>TTGGTATTGAACCAAGAGTTGCAATGTTATCCTATAGTACAGGT<br>ACCTCCGGTGCTGGTAGTGATGTCGAAAAAGTTAGAGAAGCCA<br>CTAGATTGGCTCAAGAAAAGAGACCAGATTTGATGATTGACGG<br>TCCTTTTGCAATACGATGCCGCTGTAATGGCCGACGTTGCTAAAT<br>CCAAGGCTCCAAATAGTCCTGTAGCAGGTAGAGCCACTGTTTTT<br>ATTTTCCCAGATTTGAACACTGGTAACACCACTTATAAGGCCGT<br>TCAAAGATCTGCTGACTTAATTTCAATAGGTCCAATGTTGCAGG<br>GTATGAGAAAACCTGTTAACGATTTGTCCAGAGGTGCTTTGGTC | 78 |

TABLE 2-continued

Codon optimized gene sequences (start and stop codons are underlined)

|  |  |  |
|---|---|---|
|  | GATGACATAGTATACACCATCGCTTTGACTGCAATTCAAGCCTC<br>TCAACAACAACAA<u>TAA</u>GCTAGCTAG |  |
| PO<sub>AV</sub> | ATAAGAAT*GCGGCCGC*<u>ATG</u>TCCGACAACAAGATCAACATTGGT<br>TTGGCAGTTATGAAAATATTGGAATCCTGGGGTGCTGACACTAT<br>CTACGGTATCCCTTCAGGTACTTTGTCTTCATTAATGGATGCTAT<br>GGGTGAAGAAGAAAACAACGTAAAGTTCTTGCAAGTTAAGCAT<br>GAAGAAGTCGGTGCAATGGCTGCAGTTATGCAATCCAAATTCG<br>GTGGTAATTTGGGTGTAACAGTTGGTTCCGGTGGTCCAGGTGCT<br>AGTCACTTGATTAACGGTTTATACGATGCCGCTATGGACAATAT<br>TCCAGTTGTCGCTATATTGGGTTCAAGACCTCAAAGAGAATTGA<br>ACATGGATGCATTCCAAGAATTGAACCAAAACCCAATGTACGA<br>TCATATTGCCGTATACAATAGAAGAGTTGCCTATGCTGAACAAT<br>TGCCTAAATTAGTTGATGAAGCAGCCAGAATGGCAATCGCCAA<br>GAGAGGTGTCGCCGTATTAGAAGTCCCTGGTGACTTCGCTAAG<br>GTAGAAATTGATAACGACCAATGGTACTCCAGTGCTAATTCCTT<br>GAGAAAATATGCACCAATAGCCCCTGCTGCACAAGATATCGAC<br>GCCGCTGTAGAATTGTTGAACAACAGTAAGAGACCTGTTATCTA<br>CGCAGGTATTGGTACTATGGGTCACGGTCCAGCCGTCCAAGAA<br>TTAGCTAGAAAAATCAAGGCACCTGTAATTACTACAGGTAAAA<br>ATTTCGAAACATTCGAATGGGATTTTGAAGCATTGACAGGTTCA<br>ACCTATAGAGTTGGTTGGAAACCAGCCAACGAAACTATTTTGG<br>AAGCAGATACAGTCTTATTCGCCGGTTCTAATTTTCCTTTCTCAG<br>AAGTTGAAGGTACTTTTAGAAACGTCGATAACTTCATCCAAATA<br>GATATAGACCCAGCTATGTTAGGTAAAAGACATCACGCTGATG<br>TTGCAATTTTGGGTGACGCCGGTTTGGCTATCGATGAAATCTTG<br>AATAAGGTTGATGCTGTCGAAGAATCTGCATGGTGGACAGCCA<br>ATTTGAAGAACATTGCAAACTGGAGAGAATACATCAACATGTT<br>GGAAACCAAGGAAGAGGGTGACTTGCAATTCTACCAAGTTTAC<br>AACGCTATAAATAACCATGCTGATGAAGACGCAATCTATTCTAT<br>AGATGTTGGTAACTCTACCCAAACTTCAATTAGACATTTGCACA<br>TGACCCCAAAGAATATGTGGAGAACCTCACCTTTATTTGCCACT<br>ATGGGTATCGCTATTCCAGGTGGTTTGGGTGCTAAAAACACTTA<br>TCCTGACAGACAAGTTTGGAATATTATAGGTGACGGTGCATTCT<br>CTATGACATACCCAGACGTAGTTACCAACGTTAGATATAATATG<br>CCTGTTATCAACGTCGTATTTTCAAACACAGAATACGCTTTCAT<br>TAAAAATAAGTATGAAGATACCAATAAGAACTTGTTTGGTGTC<br>GACTTCACTGATGTAGACTACGCTAAAATAGCTGAAGCACAAG<br>GTGCAAAGGGTTTTACCGTTTCTAGAATCGAAGATATGGACAG<br>AGTTATGGCCGAAGCTGTCGCAGCCAATAAGGCTGGTCATACT<br>GTTGTCATAGACTGTAAGATCACACAAGATAGACCAATTCCTGT<br>TGAAACATTGAAGTTGGACTCCAAGTTGTACAGTGAAGATGAA<br>ATTAAAGCTTACAAGGAAAGATACGAAGCTGCAAATTTGGTTC<br>CTTTTAGAGAATACTTGGAAGCAGAAGGTTTAGAATCTAAATAT<br>ATTAAG<u>TAA</u>TTAATTAAGG | 79 |
| PO<sub>SP</sub> | ATAAGAAT*GCGGCCGC*<u>ATG</u>ACACAAGGTAAAATCACTGCCTCC<br>GCCGCAATGTTGAATGTATTAAAGACCTGGGGTGTTGACACAA<br>TCTACGGTATTCCAAGTGGTACATTGTCTTCATTAATGGATGCA<br>TTGGCCGAAGATAAGGACATAAGATTTTTACAAGTAAGACATG<br>AAGAAACCGGTGCCTTGGCTGCAGTTATGCAGGCTAAGTTCGG<br>TGGTAGTATTGGTGTAGCAGTTGGTTCTGGTGGTCCAGGTGCCA<br>CTCATTTGATTAATGGTGTATATGATGCCGCTATGGACAATACA<br>CCATTTTTGGCTATATTGGGTTCAAGACCTGTTAACGAATTGAA<br>CATGGATGCATTCCAAGAATTGAACCAAAACCCAATGTACAAC<br>GGTATAGCTGTATACAACAAGAGAGTTGCTTATGCAGAACAAT<br>TGCCTAAAGTCATCGATGAAGCTTGTAGAGCAGCCATTTCCAAA<br>AAGGGTCCAGCAGTTGTCGAAATACCTGTTAACTTTGGTTTCCA<br>AGAAATCGATGAAAACTCATACTACGGTTCCGGTAGTTACGAA<br>AGATCCTTTATCGCCCCAGCTTTGAATGAAGTTGAAATCGACAA<br>GGCAGTCGAAATTTTAAATAACGCCGAAAGACCAGTTATATAT<br>GCTGGTTTCGGTGGTGTCAAAGCAGGTGAAGTAATTACAGAAT<br>TGTCTAGAAAGATTAAAGCCCCAATAATCACTACAGGTAAAA<br>TTTTCGAAGCTTTCGAATGGAACTACGAAGGTTTAACCGGTTCAG<br>CTTATAGAGTTGGTTGGAAACCTGCCAATGAAGTAGTTTTTGAA<br>GCTGATACTGTCTTGTTCTTAGGTTCCAACTTTGCATTCGCCGAA<br>GTATACGAAGCTTTTAAGAACACAGAAAAATTCATACAAGTTG<br>ATATCGACCCATATAAATTGGGTAAAAGACATGCATTGGATGC<br>CAGTATATTAGGTGACGCTGGTCAAGCTGCAAAGGCAATCTTA<br>GATAAAGTTAATCCAGTCGAATCTACACCTTGGTGGAGAGCTA<br>ACGTTAAAATAACCAAAACTGGAGAGACTACATGAATAAGTT<br>GGAAGGTAAAACTGAGGGTGAATTGCAATTGTACCAAGTTTAC<br>AACGCTATTAACAAACACGCCGATCAAGACGCTATCTATTCTTT<br>GGATGTCGGTTCAACCACTCAAACATCCACCAGACATTTGCACA<br>TGACACCTAAAAATATGTGGAGAACTTCACCTTTGTTTGCAACA<br>ATGGGTATAGCCTTACCAGGTGGTATCGCCGCTAAAAAGGATA<br>CCCCTGACAGACAAGTTTGGAACATTATGGGTGACGGTGCTTTT<br>AATATGTGCTACCCAGATGTAATCACTAACGTTCAATACGACTT | 80 |

TABLE 2-continued

Codon optimized gene sequences (start and stop codons are underlined)

|  |  |  |
|---|---|---|
|  | GCCAGTTATTAATTTGGTATTTTCTAACGCTGAATACGGTTTTAT<br>TAAAAATAAGTACGAAGATACAAATAAGCATTTGTTCGGTGTT<br>GATTTCACCAACGCAGACTACGGTAAAATTGCTGAAGCACAAG<br>GTGCCGTTGGTTTTACTGTCGATAGAATCGAAGATATTGACGCA<br>GTCGTAGCCGAAGCTGTTAAGTTGAATAAGGGTGGTAAAACCG<br>TTGTCATTGATGCTAGAATAACTCAACATAGACCATTGCCTGTC<br>GAAGTATTGGAATTAGACCCAAAGTTACACAGTGAAGAAGCTA<br>TTAAAGCTTTTAAAGAAAAGTACGAAGCAGAAGAATTGGTTCC<br>TTTTAGATTGTTCTTAGAAGAAGAAGGTTTACAATCTAGAGCTA<br>TTAAA<u>TAA</u>*TAATTAAGG* |  |
| PO<sub>LP</sub> | ATAAGAAT*GCGGCCGC*<u>ATG</u>GTAATGAAACAAACAAAGCAAAC<br>AAACATCTTAGCAGGTGCCGCCGTTATCAAGGTATTGGAAGCA<br>TGGGGTGTAGACCACTTATATGGTATTCCAGGTGGTTCCATCAA<br>TAGTATTATGGATGCCTTGTCCGCTGAAAGAGACAGAATACATT<br>ACATCCAAGTCAGACACGAAGAAGTAGGTGCAATGGCTGCAGC<br>CGCTGATGCCAAGTTGACTGGTAAAATAGGTGTTTGTTTCGGTT<br>CAGCTGGTCCAGGTGGTACACATTTGATGAATGGTTTATATGAT<br>GCAAGAGAAGACCACGTTCCTGTCTTGGCTTTAATTGGTCAATT<br>CGGTACTACTGGTATGAACATGGATACTTTCCAAGAAATGAAC<br>GAAAACCCAATCTATGCAGATGTTGCCGACTACAATGTAACAG<br>CTGTTAACGCAGCCACCTTGCCTCATGTCATCGATGAAGCAATT<br>AGAAGAGCCTACGCTCACCAAGGTGTCGCTGTTGTCCAAATTCC<br>AGTAGATTTGCCTTGGCAACAAATACCAGCAGAAGACTGGTAT<br>GCATCTGCCAATTCATACCAAACCCCTTTGTTACCAGAACCTGA<br>TGTCCAAGCTGTAACTAGATTGACCCAAACTTTGTTAGCTGCAG<br>AAAGACCATTAATCTATTACGGTATCGGTGCTAGAAAAGCTGG<br>TAAAGAATTGGAACAATTGTCCAAGACATTGAAGATCCCATTG<br>ATGAGTACCTATCCTGTTAAGGGTATTGTCGCCGATAGATATCC<br>AGCTTACTTGGGTTCTGCTAATAGAGTTGCACAAAAACCTGCCA<br>ACGAAGCTTTGGCACAAGCCGATGTAGTTTTGTTCGTTGGTAAC<br>AACTACCCATTCGCAGAAGTTTCAAAGGCCTTCAAGAACACTA<br>GATACTTTTTGCAAATAGATATCGACCCTGCAAAGTTGGGTAAA<br>AGACATAAGACTGATATAGCTGTCTTGGCTGACGCACAAAAGA<br>CATTGGCCGCTATATTGCTCAAGTATCCGAAAGAGAAAGTAC<br>ACCATGGTGGCAAGCCAACTTAGCTAATGTTAAGAACTGGAGA<br>GCATATTTGGCCTCCTTAGAAGATAAACAAGAAGGTCCATTGC<br>AAGCCTACCAAGTATTGAGAGCTGTTAATAAGATCGCTGAACC<br>TGATGCAATCTATAGTATAGATGTTGGTGACATCAATTTGAACG<br>CTAACAGACATTTGAAGTTGACACCATCTAACAGACACATCACT<br>TCAAACTTATTCGCAACAATGGGTGTTGGTATTCCAGGTGCTAT<br>AGCAGCCAAGTTGAACTACCCTGAAAGACAAGTTTTTAACTTA<br>GCTGGTGACGGTGGTGCATCTATGACCATGCAAGACTTGGCTAC<br>TCAAGTACAATACCATTTGCCTGTTATAAATGTCGTATTCACAA<br>ACTGCCAATACGGTTTTATCAAGGATGAACAAGAAGACACCAA<br>CCAAAACGATTTCATAGGTGTTGAATTCAATGATATCGACTTCT<br>CTAAGATCGCTGACGGTGTTCATATGCAAGCATTCAGAGTCAAC<br>AAGATCGAACAATTGCCAGATGTTTTTGAACAAGCCAAAGCTA<br>TTGCACAACACGAACCTGTTTTGATCGATGCTGTCATTACCGGT<br>GACAGACCATTACCTGCAGAAAAATTGAGATTAGATTCTGCCA<br>TGTCTTCAGCTGCAGACATTGAAGCCTTTAAGCAAAGATATGAA<br>GCTCAAGATTTGCAACCATTGTCAACATACTTAAAGCAATTCGG<br>TTTGGATGACTTACAACATCAAATTGGTCAAGGTGGTTTTT<u>TAA</u>T<br>*TAATTAAGG* | 81 |
| hACL-<br>opt<br>from<br>human | <u>ATG</u>TCCGCAAAAGCCATTTCCGAACAAACTGGTAAAGAATTAT<br>TATACAAGTTCATCTGCACAACCTCAGCCATACAAAACAGATTC<br>AAGTATGCAAGAGTTACTCCAGATACGACTGGGCCAGATTGT<br>TACAAGATCATCCTTGGTTGTTATCACAAAACTTGGTTGTCAAG<br>CCTGACCAATTGATTAAAAGACGTGGTAAATTGGGTTTAGTAG<br>GTGTTAATTTGACATTAGATGGTGTTAAGTCCTGGTTGAAGCCA<br>AGATTAGGTCAAGAAGCAACCGTCGGTAAAGCCACTGGTTTCT<br>TGAAAAATTTCTTGATCGAACCATTCGTACCTCATTCTCAAGCT<br>GAAGAATTTTACGTTTGTATATACGCAACTAGAGAAGGTGACT<br>ATGTCTTGTTTCATCACGAAGGTGGTGTTGATGTAGGTGACGTA<br>GACGCCAAAGCTCAAAAGTTGTTAGTTGGTGTCGATGAAAAAT<br>TGAACCCAGAAGACATTAAAAAGCATTTGTTGGTTCACGCCCCT<br>GAAGATAAAAGGAAATATTGGCTTCTTTTATCTCAGGTTTGTT<br>TAATTTCTACGAAGATTTGTACTTCACTTACTTGGAAATTAACC<br>CATTGGTAGTTACAAAGGATGGTGTATACGTTTTGGACTTAGCT<br>GCAAAGGTCGATGCAACAGCCGACTACATTTGTAAAGTAAAGT<br>GGGGTGACATAGAATTTCCACCTCCATTCGGTAGAAGCATA<br>TCCAGAAGAAGCCTACATTGCTGATTTGGACGCCAATCCGGT<br>GCTAGTTTGAAGTTAACCTTGTTGAACCCTAAAGGTAGAATCTG<br>GACTATGGTTGCAGGTGGTGGTGCCTCAGTCGTATATTCCGATA<br>CTATTTGCGACTTGGGTGGTGTTAACGAATTAGCTAACTACGGT<br>GAATACAGTGGTGCACCATCTGAACAACAAACCTATGATTACG<br>CTAAGACTATCTTGAGTTTAATGACAAGAGAAAAGCATCCTGA | 82 |

TABLE 2-continued

Codon optimized gene sequences (start and stop codons are underlined)

|  |  |  |
|---|---|---|
|  | TGGTAAAATTTTGATCATCGGTGGTTCTATCGCTAACTTCACAA<br>ACGTCGCCGCTACCTTCAAAGGTATAGTAAGAGCAATCAGAGA<br>TTACCAAGGTCCATTGAAGGAACACGAAGTAACCATTTTGTTA<br>GAAGAGGTGGTCCTAACTACCAAGAAGGTTTAAGAGTCATGGG<br>TGAAGTAGGTAAAACTACAGGTATCCCAATTCATGTATTTGGTA<br>CTGAAACTCACATGACTGCTATTGTTGGTATGGCATTAGGTCAT<br>AGACCAATACCTAATCAACCTCCAACTGCTGCTCACACAGCTAA<br>TTTCTTGTTAAACGCATCTGGTTCAACATCCACCCCAGCCCCAT<br>CAAGAACAGCTAGTTTCTCTGAATCAAGAGCTGATGAAGTTGCT<br>CCAGCTAAGAAAGCAAAACCAGCCATGCCTCAAGACTCTGTTC<br>CATCACCTAGATCCTTGCAAGGTAAAAGTACCACTTTGTTTTCA<br>AGACATACAAAGGCAATTGTTTGGGGTATGCAAACCAGAGCCG<br>TCCAAGGCATGTTGGATTTCGACTATGTTTGTTCAAGAGATGAA<br>CCATCCGTTGCTGCAATGGTCTATCCTTTTACTGGTGACCATAA<br>ACAAAAGTTCTACTGGGGTCACAAGGAAATATTAATCCCAGTTT<br>TTAAAAACATGGCCGATGCTATGAGAAAGCATCCTGAAGTTGA<br>TGTATTGATTAACTTCGCAAGTTTAAGATCAGCCTATGATTCAA<br>CTATGGAAACTATGAACTACGCTCAAATCAGAACTATTGCTATC<br>ATTGCAGAAGGTATCCCAGAAGCATTGACAAGAAAATTAATTA<br>AAAAGGCAGATCAAAAGGGTGTAACCATAATCGGTCCAGCAAC<br>TGTTGGTGGTATCAAACCTGGTTGTTTTAAGATTGGTAATACAG<br>GTGGCATGTTGGATAACATATTGGCTTCAAAATTGTATAGACCA<br>GGTTCCGTCGCATACGTATCCAGAAGTGGTGGTATGAGTAACG<br>AATTAAACAACATAATTTCAAGAACAACCGATGGTGTATATGA<br>AGGTGTTGCTATTGGTGGTGACAGATACCCAGGTTCTACTTTTA<br>TGGATCATGTTTTGAGATATCAAGACACCCCTGGTGTCAAATG<br>ATCGTTGTCTTAGGTGAAATAGGTGGTACAGAAGAATACAAAA<br>TTTGTAGAGGTATTAAGGAAGGTAGATTGACCAAACCAATTGTT<br>TGTTGGTGCATAGGTACATGTGCTACCATGTTTTCTTCAGAAGT<br>TCAATTCGGTCACGCAGGTGCCTGCGCTAATCAAGCATCTGAAA<br>CAGCAGTTGCCAAAAACCAAGCATTGAAGGAAGCAGGTGTTTT<br>TGTCCCTAGATCATTCGATGAATTGGGTGAAATCATTCAATCCG<br>TCTATGAAGACTTAGTAGCCAATGGTGTAATTGTTCCAGCTCAA<br>GAAGTTCCTCCACCTACTGTCCCTATGGATTACTCTTGGGCTAG<br>AGAATTGGGTTTAATCAGAAAACCAGCTTCTTTTATGACTTCCA<br>TTTGTGATGAAAGAGGTCAAGAATTGATCTATGCTGGTATGCCT<br>ATCACAGAAGTTTTCAAGGAAGAAATGGGTATAGGTGGTGTCT<br>TGGGTTTGTTGTGGTTCCAAAAGAGATTGCCAAAGTACTCATGT<br>CAATTCATTGAAATGTGCTTAATGGTCACCGCTGATCATGGTCC<br>TGCCGTATCCGGTGCTCACAACACTATAATCTGCGCTAGAGCAG<br>GTAAAGATTTGGTTTCTTCTTTGACTTCAGGTTTGTTAACAATTG<br>GTGACAGATTTGGTGGTGCTTTGGACGCCGCTGCAAAGATGTTT<br>AGTAAGGCATTCGATTCTGGTATAATCCCAATGGAATTTGTTAA<br>TAAGATGAAAAAGGAGGGTAAATTAATCATGGGTATCGGTCAT<br>CGTGTTAAGTCTATAAATAACCCTGATATGAGAGTACAAATCTT<br>GAAGGACTATGTTAGACAACACTTTCCAGCAACACCTTTGTTAG<br>ATTACGCCTTAGAAGTTGAAAAGATTACTACATCTAAGAAACC<br>AAATTTGATCTTGAACGTTGATGGTTTGATCGGTGTTGCTTTTGT<br>TGATATGTTAAGAAACTGTGGTAGTTTCACTAGAGAAGAAGCC<br>GATGAATATATTGACATCGGTGCTTTGAACGGTATCTTCGTTTT<br>GGGTAGATCAATGGGTTTTATTGGTCATTACTTGGATCAAAGA<br>GATTAAAGCAAGGTTTGTATAGACACCCTTGGGATGATATTTCC<br>TACGTTTTGCCTGAACACATGAGTATG<u>TAA</u> |  |
| mACL-<br>Opt<br>from<br>mouse | <u>ATG</u>TCCGCTAAAGCTATTTCCGAACAAACTGGTAAAGAATTATT<br>ATACAAGTACATTTGCACCACCTCAGCCATACAAAACAGATTC<br>AAGTATGCAAGAGTTACACCAGATACCGACTGGGCCCATTTGTT<br>ACAAGATCACCCTTGGTTGTTATCTCAATCATTGGTTGTCAAAC<br>CTGACCAATTGATTAAAAGACGTGGTAAATTGGGTTTAGTCGGT<br>GTAAACTTGAGTTTAGATGGTGTTAAGTCTTGGTTGAAGCCAAG<br>ATTAGGTCATGAAGCTACAGTTGGTAAAGCAAAGGGTTTCTTG<br>AAAAATTTCTTGATCGAACCATTCGTACCTCACTCACAAGCTGA<br>AGAATTTTACGTTTGTATCTATGCAACTAGAGAAGGTGACTATG<br>TCTTGTTTCATCACGAAGGTGGTGTTGACGTCGGTGACGTTGAC<br>GCCAAAGCTCAAAAGTTGTTAGTAGGTGTTGATGAAAAGTTAA<br>ACACAGAAGACATCAAGAGACATTTGTTGGTACACGCCCCAGA<br>AGATAAAAAGGAAGTTTTGGCTTCCTTTATAAGTGGTTTGTTTA<br>ATTTCTACGAAGATTTGTACTTCACCTACTTGGAAATTAACCCT<br>TTAGTAGTTACTAAGGATGGTGTCTATATATTGGACTTAGCTGC<br>AAAAGTAGATGCAACTGCCGACTACATCTGTAAGGTTAAGTGG<br>GGTGACATTGAATTTCCACCTTCCATTCGGTAGAGAAGCATATCC<br>AGAAGAAGCCTACATTGCTGATTTGGACGCAAAATCTGGTGCC<br>TCATTGAAGTTAACATTGTTGAACCCTAAGGGTAGAATATGGAC<br>TATGGTTGCTGGTGGTGGTGCAAGTGTCGTATATTCTGATACAA<br>TCTGCGACTTGGGTGGTGTTAACGAATTAGCTAACTACGGTGAA<br>TACTCAGGTGCACCATCCGAACAACAAACTTATGATTACGCTAA<br>GACCCATCTTGAGTTTAATGACTAGAGAAAAGCATCCTGAAGGT<br>AAAATTTTGATCATCGGTGGTTCTATAGCAAACTTCACTAACGT | 83 |

TABLE 2-continued

Codon optimized gene sequences (start and stop codons are underlined)

```
TGCCGCTACATTCAAGGGTATAGTCAGAGCTATCAGAGATTATC
AAGGTCCATTGAAGGAACACGAAGTTACAATATTCGTCAGAAG
AGGTGGTCCTAACTACCAAGAAGGTTTAAGAGTAATGGGTGAA
GTTGGTAAAACTACAGGTATCCCAATTCATGTATTTGGTACTGA
AACACACATGACTGCCATCGTTGGTATGGCTTTAGGTCATAGAC
CAATTCCTAATCAACCTCCAACAGCAGCCCACACCGCCAATTTC
TTGTTAAACGCTTCCGGTAGTACCTCTACTCCAGCACCATCAAG
AACTGCCTCATTCTCCGAAAGTAGAGCTGATGAAGTTGCTCCAG
CTAAGAAAGCAAAACCAGCCATGCCTCAAGACTCCGTTCCAAG
TCCTAGATCATTGCAAGGTAAATCAGCAACATTATTTTCCAGAC
ATACCAAAGCCATTGTATGGGGTATGCAAACAAGAGCTGTTCA
AGGCATGTTGGATTTCGACTATGTTGTAGTAGAGATGAACCAT
CTGTCGCTGCAATGGTATATCCTTTTACCGGTGACCATAAACAA
AAGTTCTACTGGGGTCACAAGGAAATATTAATCCCAGTTTTTAA
AAACATGGCCGATGCTATGAAAAAGCATCCTGAAGTTGATGTA
TTGATTAACTTCGCTTCATTAAGATCCGCTTATGATTCTACTATG
GAAACAATGAACTACGCACAAATTAGAACCATAGCTATCATTG
CAGAAGGTATACCAGAAGCATTGACTAGAAAGTTAATCAAAAA
GGCCGATCAAAAAGGTGTCACTATAATCGGTCCAGCTACAGTA
GGTGGTATAAAACCTGGTTGTTTTAAGATCGGTAATACTGGTGG
CATGTTGGATAACATATTGGCATCAAAATTGTATAGACCAGGTT
CCGTAGCTTACGTTTCAAGAAGCGGTGGTATGAGTAACGAATT
GAACAACATAATTTCAAGAACCACTGATGGTGTTTATGAAGGT
GTCGCTATTGGTGGTGACAGATACCCAGGTTCTACTTTTATGGA
TCATGTTTTGAGATATCAAGACACACCTGGTGTCAAAATGATCG
TTGTCTTAGGTGAAATAGGTGGTACTGAAGAATACAAAATTTGC
AGAGGTATAAAGGAAGGTAGATTGACAAAACCAGTAGTTTGTT
GGTGCATTGGTACTTGTGCAACTATGTTTTCTTCAGAAGTTCAA
TTCGGTCATGCAGGTGCCTGCGCTAATCAAGCATCTGAAACAGC
AGTTGCCAAAACCAAGCCTTAAAGGAAGCTGGTGTTTTTGTCC
CTAGATCATTCGATGAATTGGGTGAAATCATTCAATCCGTATAT
GAAGACTTAGTTGCCAAGGGTGCTATTGTCCCAGCTCAAGAAG
TACCTCCACCTACTGTTCCTATGGATTACTCATGGGCAAGAGAA
TTGGGTTTGATCAGAAAGCCAGCTAGTTTTATGACCTCTATCTG
TGATGAAAGAGGTCAAGAATTGATCTATGCTGGTATGCCTATCA
CTGAAGTCTTCAAGGAAGAAATGGGTATCGGTGGTGTATTGGG
TTTGTTGTGGTTCCAAAGAAGATTACCAAAGTACTCATGTCAAT
TCATAGAAATGTGCTTAATGGTTACAGCTGATCATGGTCCAGCT
GTTTCTGGTGCCCACAACACCATAATCTGCGCTAGAGCAGGTAA
AGATTTGGTTTCTTCTTTGACCTCTGGTTTGTTAACTATTGGTGA
CAGATTTGGTGGTGCATTGGACGCCGCTGCAAAAATGTTTTCAA
AGGCTTTCGATTCCGGTATAATCCCAATGGAATTTGTTAATAAG
ATGAAAAAGGAGGGTAAATTAATCATGGGTATCGGTCATCGTG
TTAAGTCAATTAATAACCCTGATATGAGAGTCCAAATATTGAAG
GACTTCGTAAAGCAACACTTCCCAGCAACACCTTTGTTAGATTA
CGCCTTAGAAGTTGAAAAGATTACAACCTCTAAAAAGCCAAAT
TTGATCTTGAACGTTGATGGTTTTATAGGTGTCGCTTTCGTAGA
CATGTTAAGAAACTGTGGTTCTTTTACTAGAGAAGAAGCCGATG
AATATGTTGACATTGGTGCTTTGAATGGTATATTTGTCTTAGGT
AGATCAATGGGTTTTATTGGTCATTACTTGGATCAAAAGAGATT
AAAGCAAGGTTTGTATAGACACCCTTGGGACGATATTTCCTACG
TTTTGCCTGAACACATGAGTATGTAA
```

The invention claimed is:

1. A yeast comprising at least one heterologous pathway for synthesis of cytosolic acetyl-Coenzyme A (CoA), the at least one heterologous pathway comprising heterologous genes encoding a respective enzyme involved in synthesis of acetyl-CoA, with the proviso that the heterologous genes are not a heterologous gene encoding a pyruvate formate lyase, wherein the heterologous genes comprise:
   at least one heterologous gene encoding a cytosolic pyruvate dehydrogenase complex selected from the group consisting of genes encoding an *Escherichia coli* cytosolic pyruvate dehydrogenase complex, genes encoding a *Saccharomyces cerevisiae* pyruvate dehydrogenase complex but lacking mitochondrial target signal (MTS), genes encoding an *Azotobacter vinelandii* pyruvate dehydrogenase complex, and genes encoding an *Enterococcus faecalis* pyruvate dehydrogenase complex; and
   at least one heterologous gene encoding respective enzymes involved in attachment and activation of lipoyl groups to said cytosolic pyruvate dehydrogenase complex selected from the group consisting of genes encoding *Escherichia coli* lipoic acid synthetase and/or lipoate-protein ligase, and genes encoding *Saccharomyces cerevisiae* LIP2, LIP3, LIP5 and GCV3, each of which is lacking MTS.

2. The yeast according to claim 1, wherein the genes encoding an *Escherichia coli* cytosolic pyruvate dehydrogenase complex are aceE, aceF, and/or lpd, the genes encoding a *Saccharomyces cerevisiae* pyruvate dehydrogenase complex but lacking mitochondrial target signal (MTS) are PDA1, PDB1, LAT1, LPD1, and/or PDX1, each of which lack MTS, the genes encoding an *Azotobacter vinelandii* pyruvate dehydrogenase complex are aceE, aceF, and/or lpdA, the genes encoding an *Enterococcus faecalis* pyruvate dehydrogenase complex are pdhA, pdhB, aceF and/or lpdA, and the genes encoding *Escherichia coli* lipoic acid synthetase and/or lipoate-protein ligase are lipA, lipB, and/or lplA.

3. The yeast according to claim 1, wherein the yeast lacks any endogenous gene encoding pyruvate decarboxylase or comprises a disrupted gene or genes encoding pyruvate decarboxylase.

4. The yeast according to claim 3, wherein said yeast lacks endogenous genes encoding PDC1, PDC5 and/or PDC6 or comprises disrupted genes encoding PDC1, PDC5 and/or PDC6 to block conversion of pyruvate to ethanol.

5. A method of producing acetyl-Coenzyme A (CoA) comprising culturing a yeast according to claim 1 in culture conditions suitable for production of cytosolic acetyl-CoA from said yeast.

6. The method according to claim 5, further comprising collecting said acetyl-CoA or a compound generated by said yeast from said acetyl-CoA from a culture medium in which said yeast is cultured and/or from said yeast, wherein said compound is selected from a group consisting of fatty acids, 3-hydroxypropionic acid, isoprenoids, polyhydroxyalkanoates, 1-butanol and polyketides.

7. A method of producing acetyl-Coenzyme A (CoA) comprising culturing a yeast according to claim 3 culture conditions suitable for production of cytosolic acetyl-CoA from said yeast.

8. A method of producing a yeast suitable for the production of cytosolic acetyl-Coenzyme A (CoA) comprising:
   introducing, into said yeast, at least one heterologous pathway for synthesis of cytosolic acetyl-CoA, said at least one heterologous pathway comprising heterologous genes encoding a respective enzyme involved in synthesis of acetyl-CoA, with the proviso that said heterologous genes are not a heterologous gene encoding a pyruvate formate lyase,
   wherein the heterologous genes comprise:
   at least one heterologous gene encoding a cytosolic pyruvate dehydrogenase complex selected from the group consisting of genes encoding an *Escherichia coli* cytosolic pyruvate dehydrogenase complex, genes encoding a *Saccharomyces cerevisiae* pyruvate dehydrogenase complex but lacking mitochondrial target signal (MTS), genes encoding an *Azotobacter vinelandii* pyruvate dehydrogenase complex, and genes encoding an *Enterococcus faecalis* pyruvate dehydrogenase complex; and
   at least one heterologous gene encoding respective enzymes involved in attachment and activation of lipoyl groups to said cytosolic pyruvate dehydrogenase complex selected from the group consisting of genes encoding *Escherichia coli* lipoic acid synthetase and/or lipoate-protein ligase, and genes encoding *Saccharomyces cerevisiae* LIP2, LIP3, LIP5 and GCV3, each of which is lacking MTS.

9. The method of claim 8, further comprising deleting or disrupting any endogenous gene encoding pyruvate decarboxylase in said yeast.

\* \* \* \* \*

UNITED STATES PATENT AND TRADEMARK OFFICE
CERTIFICATE OF CORRECTION

PATENT NO. : 10,704,050 B2
APPLICATION NO. : 15/030132
DATED : July 7, 2020
INVENTOR(S) : Nielsen et al.

It is certified that error appears in the above-identified patent and that said Letters Patent is hereby corrected as shown below:

On the Title Page

Item (56) References Cited, FOREIGN PATENT DOCUMENTS, Column 2, Line 25: Please correct "WO 2011/159863" to read -- WO 2011/159853 --

In the Specification

Column 16, Line 59: Please correct "Guldener" to read -- Güldener --

Column 22, Line 2: Please correct "Giildener" to read -- Güldener --

In the Claims

Column 108, Line 31, Claim 7: Please correct "claim 3 culture" to read -- claim 3 in culture --

Signed and Sealed this
Seventeenth Day of November, 2020

Andrei Iancu
*Director of the United States Patent and Trademark Office*